(12) United States Patent
Bolt et al.

(10) Patent No.: US 9,125,890 B2
(45) Date of Patent: Sep. 8, 2015

(54) COMPOUNDS SUITABLE FOR TREATMENT OF HAEMOPHILIA

(71) Applicant: Novo Nordisk A/S, Bagsvaerd (DK)

(72) Inventors: Gert Bolt, Vaerloese (DK); Ditte Maria Karpf, Veskoe Sjaelland (DK); Frederik Rode, Hedehusene (DK); Jesper Haaning, Birkeroed (DK); Kirstine Roepstorff, Bagsvaerd (DK); Lars Thim, Gentofte (DK); Maj Petersen, Bagsvaerd (DK); Marianne Kjalke, Frederikssund (DK); Ole Hvilsted Olsen, Broenshoej (DK); Jens Jacob Hansen, Jyllinge (DK); Christian Rischel, Copenhagen S (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/916,262

(22) Filed: Jun. 12, 2013

(65) Prior Publication Data
US 2014/0018297 A1    Jan. 16, 2014

Related U.S. Application Data

(63) Continuation-in-part of application No. PCT/EP2013/055106, filed on Mar. 13, 2013.

(60) Provisional application No. 61/641,434, filed on May 2, 2012, provisional application No. 61/752,612, filed on Jan. 15, 2013.

(30) Foreign Application Priority Data

Apr. 24, 2012  (EP) .................................... 12165301
Jan. 9, 2013   (EP) .................................... 13150576

(51) Int. Cl.
*C07K 14/755* (2006.01)
*A61K 38/37* (2006.01)
*A61K 9/00* (2006.01)

(52) U.S. Cl.
CPC .............. *A61K 38/37* (2013.01); *A61K 9/0019* (2013.01); *C07K 14/755* (2013.01)

(58) Field of Classification Search
CPC ..... A61K 38/37; A61K 9/0019; C07K 14/755
See application file for complete search history.

(56) References Cited

U.S. PATENT DOCUMENTS

| | | |
|---|---|---|
| 5,679,776 A | 10/1997 | Burnouf-Radosevich et al. |
| 5,925,739 A | 7/1999 | Spira et al. |
| 6,005,077 A | 12/1999 | Schwarz et al. |
| 6,048,720 A | 4/2000 | Dalborg et al. |
| 6,307,032 B1 | 10/2001 | Schonhofer et al. |
| 7,033,994 B2 | 4/2006 | Araki et al. |
| 7,985,846 B2 | 7/2011 | Josic et al. |

| | | |
|---|---|---|
| 2004/0132654 A1 | 7/2004 | Kumpe et al. |
| 2005/0074866 A1 | 4/2005 | Grancha et al. |
| 2007/0275880 A1 | 11/2007 | Chtourou et al. |
| 2009/0176709 A1 | 7/2009 | Jorquera Nieto et al. |
| 2010/0093607 A1 | 4/2010 | Dickneite |
| 2010/0183556 A1 | 7/2010 | Choi et al. |

FOREIGN PATENT DOCUMENTS

| | | |
|---|---|---|
| WO | 97/41220 A1 | 11/1997 |
| WO | 2005/012354 A1 | 2/2005 |
| WO | 2008/082669 A2 | 7/2008 |
| WO | 2008/151817 A1 | 12/2008 |
| WO | 2009/062100 A1 | 5/2009 |
| WO | 2009/108806 A1 | 9/2009 |
| WO | 2009/156137 A1 | 12/2009 |
| WO | 2010/003687 A1 | 1/2010 |
| WO | 2010/062768 A1 | 6/2010 |
| WO | 2011/060242 A2 | 5/2011 |
| WO | 2011/101284 A1 | 8/2011 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
UniProt Protein Database, Coagulation factor VIII, protein Accession P00451, pp. 1-3, accessed on Oct. 2, 2014.*
UniProt Protein Database, Von Willebrand Factor, protein Accession P04275, pp. 9-10, accessed on Oct. 2, 2014.*
Castaman G, Blood Transfusion, "Treatment of Von Willebrand Disease With FVIII/VWF Concentrates;", 2011, vol. 9, No. 2, pp. s9-s13.
Denis C V et al., Hématologie, "Von Willebrand Factor's Clearance", 2006, vol. 12, No. 1, pp. 34-43.
Denis C V et al., Thrombosis and Haemostasis, "Clearance of Von Willebrand Factor", 2008, vol. 99, No. 2, pp. 271-278.
Lethagen S et al., Journal of Thrombosis and Haemostasis, "Von Willebrand Factor/Factor VIII Concentrate (Haemate¬ R P) Dosing Based on Pharmacokinetics: A Prospective Multicenter Trial in Elective Surgery", 2007, vol. 5, No. 7, pp. 1420-1430.

(Continued)

*Primary Examiner* — James H Alstrum Acevedo
*Assistant Examiner* — Erinne Dabkowski
(74) *Attorney, Agent, or Firm* — Nonna G. Akopyan

(57) ABSTRACT

The present invention relates to Von Willebrand (VWF) compounds as well as compositions suitable for treatment of blood clotting diseases. The present invention also relates to pharmaceutical compositions, freeze-dried or liquid, comprising (i) a Factor VIII molecule and (ii) a VWF compound.

20 Claims, 12 Drawing Sheets

(56) References Cited

OTHER PUBLICATIONS

Lenting P J et al., The Journal of Biological Chemistry, "An Experimental Model to Study the In Vivo Survival of Von Willebrand Factor : Basic Aspects and Application to the R1205H Mutation", 2003, vol. 279, No. 13, pp. 12102-12109.

Lethagen S.et al., Annals of Hematology, "Pharmacokinetics and Hemostatic Effect of Different Factor VLLL/Von Willebrand Factor Concentrates in Von Willebrand's Disease Type III", 1992, vol. 65, No. 6, pp. 253-259.

Pipe S W et al., Journal of Thrombosis and Haemostasis, "Functional Factor VIII Made With Von Willebrand Factor at High; Levels in Transgenic Milk", 2011, vol. 9, No. 11, pp. 2235-2242.

Purvis A R et al., Proceedings of the National Academy of Sciences of the USA, "Two CYS Residues Essential for Von Willebrand; Factor Multimer Assembly in the Golgi", 2007, vol. 104, No. 40, pp. 15647-15652.

Schooten C J et al,., Journal of Thrombosis and Haemostasis, "Cysteine-Mutations in Von Willebrand Factor Associated With; Increased Clearance", 2005, vol. 3, No. 10, pp. 2228-2237.

Shi.Q et al., Haemophilia, "Intravascular Recovery of VWF and FVIII Following; Intraperitoneal Injection and Differences From Intravenous and Subcutaneous Injection in Mice", 2012, vol. 18, No. 4, pp. 639-646.

Terraube V et al., Haemophilia, "Factor VIII and Von Willebrand Factor Interaction: Biological,; Clinical and Therapeutic Importance", 2010, vol. 16, No. 1, pp. 3-13.

Thim et al., Haemophilia, "Purification and Characterization of a New Recombinant; Factor VIII (N8)", 2010, vol. 16, No. 2, pp. 349-359.

Zhou Y et al., Blood, "Sequence and Structure Relationships Within Von Willebrand Factor", 2012, vol. 120, No. 2, pp. 449-458.

Øvlisen K et al., Journal of Thrombosis and Haemostasis, "Hemostatic Effect of Recombinant Factor VIIA, NN1731 and Recombinant Factor VIII on Needle-Induced Joint Bleeding in Hemophilia A Mice", 2008, vol. 6, pp. 969-975.

Fatouros A et al., Journal of Pharmacy and Pharmacology, "Recombinant Factor VIII SQ—Stability of VIII : C in Homogenates From Porcine, Momkey and Human Subcutaneous Tissue", 2000, vol. 52, No. 7, pp. 797-805.

\* cited by examiner

COMPOUNDS SUITABLE FOR TREATMENT OF HAEMOPHILIA

CROSS-REFERENCE TO RELATED APPLICATIONS

This application is a continuation-in-part of International Application Serial No. PCT/EP2013/055106, filed Mar. 13, 2013, which claimed priority of European Patent Application 12165301.8, filed Apr. 24, 2012 and European Patent Application 13150576.0, filed Jan. 9, 2013; this application also claims priority under 35 U.S.C. §119(e) of U.S. Provisional application 61/641,434, filed May 2, 2012 and U.S. Provisional application 61/752,612, filed Jan. 15, 2013; the contents of all above-named applications are incorporated herein by reference.

TECHNICAL FIELD

The present invention relates to treatment and/or prophylaxis of haemophilia.

BACKGROUND

Protein replacement therapy by intravenous administration of coagulation factors is currently used for treating patients suffering from haemophilia. For patient convenience and compliance, extravascular (e.g. subcutaneous (s.c.) or intradermal) administration would be preferable to the existing intravenous (i.v.) injections. There are furthermore potential safety advantages associated with extravascular administration, since many patients could avoid intravenous port surgery as well as the risk of infection and clots associated with insertion of such catheters.

S.c. administration of FVIII in FVIII deficient mice is disclosed in Shi et al, Haemophilia, 2012, DOI: 10.1111/j.1365-2516.2011.02735.x. The bioavailability of FVIII is herein reported to be low (about 1%).

S.c. administration of FVIII and VWF is furthermore disclosed in WO08151817 but no dose response relationship between the FVIII dose and the achieved circulating FVIII concentration is disclosed. In WO815817, the (Unit) ratio of VWF over FVIII was larger than 5:1, corresponding to a 150-250 fold molar excess of the concentration of VWF protein as compared to that of FVIII. From a practical and economical pint of view, this type of ratios are, however, not desirable. In WO08151817, it is furthermore shown that the immunogenicity in mice of s.c. administered FVIII is significantly reduced when FVIII is co-formulated with VWF.

In WO10062768, it is disclosed that PEGylation of FVIII can improve the bioavailability of FVIII in connection with subcutaneous injection into mice, whereas co-formulation with VWF does not improve the bioavailability of FVIII.

There is a need in the art for compounds and/or pharmaceutical compositions suitable for extravascular administration in treatment and/or prophylaxis of patients suffering from blood clotting diseases such as haemophilia A with or without inhibitors, and/or von Willebrand disease, as such administration forms would alleviate the burden of i.v. treatment both related to the infusion as such and also the risk of infections due to implanted portable catheters. Such compounds and compositions are preferably safe (i.e. have a low risk of immunogenicity) and/or have a high bioavailability and/or are preferably easy to handle in connection with production and formulation processes.

SUMMARY

The present invention relates to a recombinant VWF fragment comprising 1200 amino acids or less, such as e.g. the TIL' domain or the TIL'/E' domain (Zhou et al. Blood 2012; 120(2): 449-458). The present invention furthermore relates to a pharmaceutical composition comprising: (i) a VWF fragment according to the invention and (ii) FVIII molecule (full-length/truncated B domain/conjugated). The present invention furthermore relates to use thereof for treatment of haemophilia, e.g. by extravascular administration. Such compounds and compositions will preferably result in a relatively high FVIII bioavailability and/or a relatively low risk of FVIII immunogenicity in connection with extravascular co-administration of FVIII.

DESCRIPTION

In one aspect of the invention, VWF fragments according to the invention co-administered with FVIII molecules having a prolonged in vivo circulatory half-life have a surprisingly high bioavailability in connection with extravascular (e.g. s.c.) administration thereof.

The inventors of the present invention have furthermore made the surprising observation that bioavailability of FVIII molecules may be significantly improved upon extravascular co-administration with similar molar amounts of VWF fragments according to the invention. Alternatively, high bioavailability may be achieved through extravascular co-administration of a pool of FVIII molecules, wherein the majority of said FVIII molecules are bound to VWF fragments according to the invention. Interestingly, full length VWF does not have a positive impact on the bioavailability of FVIII. Preferably, VWF should be in the form of a VWF fragment that comprise the TIL' or the TIL'/E' domains. Compounds and compositions according to the present invention are thus useful for treatment and prophylaxis of haemophilia patients (in particular haemophilia A patients) with and without inhibitors, as well as for immune tolerance induction (ITI) of haemophilia patients with inhibitors.

DEFINITIONS

Figure 1:
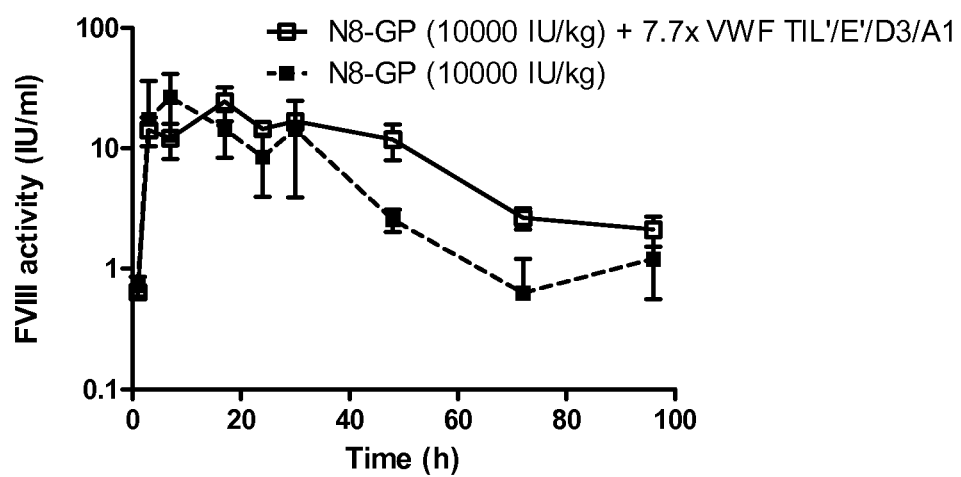
FIG. 1: FVIII activity in plasma after subcutaneous administration of 10000 U/kg "N8-GP" with or without co-administration of 7.7 times the molar dose of VWF TIL'/E'/D3/A1 relatively to N8-GP. Data are mean and standard deviation of measurements from n=2 FVIII KO mice per time point. "N8-GP" is a glyco-PEGylated FVIII molecule produced as described in Examples 1+2 in WO2009108806.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to treating a disease in said human or other vertebrate. The timing and purpose of said treatment may vary from one individual to another, according to the subject's health. Thus, said treatment may be prophylactic, palliative, symptomatic and/or curative.

Mode of Administration: Compounds and pharmaceutical compositions according to the invention may be administered parenterally, such as e.g. intravenously or extravascularly (such as e.g. intradermally, intramuscularly, subcutaneously, etc). Compounds and pharmaceutical compositions according to the invention may be administered prophylactically and/or therapeutically and/or on demand. According to the present invention, several advantages are associated with extravascular administration of compounds/pharmaceutical compositions according to the present invention. Extravascular administration is easier, simpler, and associated with less pain, inconvenience, and complications (and thus potentially resulting in better compliance) which is of potential benefit to all patients but of particular benefit for children and small infants.

Combination Treatments/Co-Administration: Combined administration of two or more active compounds (e.g. FVIII and VWF/VWF fragments according to the invention having the ability to bind to FVIII) may be achieved in a number of different ways. In one embodiment, the two active compounds may be administered together in a single composition. In another embodiment, the two active compounds may be administered in separate compositions as part of a combined therapy. For example, the first compound may be administered before, after, or concurrently with the second compound. In case FVIII and VWF fragment are administered extravascularly (e.g. subcutaneously) as two separate pharmaceutical compositions, they are preferably administered in close proximity in order to benefit from the improved bioavailability that can be obtained when administering these two types of compounds together (i.e. the injection sites should be separated by no more than 5 cm, preferably no more than 4 cm, preferably no more than 3 cm, preferably no more than 2 cm, and most preferably no more than 1 cm). The two compounds should preferably also be injected within about an hour, preferably within about 30 minutes, preferably within about 15 minutes, and most preferably within about 5 minutes.

Factor VIII: Factor VIII (FVIII) is a large, complex glycoprotein that is primarily produced by hepatocytes. Human FVIII comprises 2351 amino acids, including a signal peptide, and contains several distinct domains as defined by homology. There are three A-domains, a unique B-domain, and two C-domains. The domain order can be listed as NH2-A1-A2-B-A3-C1-C2-COOH. The chains are connected by bivalent metal ion-bindings. The A1-A2-B chain is termed the heavy chain (HC) while the A3-C1-C2 is termed the light chain (LC). Small acidic regions C-terminal of the A1 (the a1 region) and A2 (the a2 region) and N-terminal of the A3 domain (the a3 region) play important roles in its interaction with other coagulation proteins, including thrombin and von Willebrand factor (VWF), the carrier protein for FVIII.

Endogenous FVIII molecules circulate in vivo as a pool of molecules with B domains of various sizes, the shortest having C-terminal at position 740, i.e. at the C-terminal of A2-a2, and thus contains no B domain. These FVIII molecules with B-domains of different length all have full procoagulant activity. Upon activation with thrombin, FVIII is cleaved C-terminal of A1-a1 at position 372, C-terminal of A2-a2 at position 740, and between a3 and A3 at position 1689, the latter cleavage releasing the a3 region with concomitant loss of affinity for VWF. The activated FVIII molecule is termed FVIIIa. The activation allows interaction of FVIIIa with phospholipid surfaces like activated platelets and activated factor IX (FIXa), i.e. the tenase complex is formed, allowing efficient activation of factor X (FX).

The terms "Factor VIII(a)" and "FVIII(a)" include both FVIII and FVIIIa. Similarly, the term "Factor VIII" and "FVIII" may include both FVIII and FVIIIa. "Factor VIII" or "FVIII" as used herein refers to a human plasma glycoprotein that is a member of the intrinsic coagulation pathway and is essential to blood coagulation. "Wildtype(wt)/native FVIII" is the human FVIII molecule derived from the full length sequence as shown in SEQ ID NO: 1 (amino acid 1-2332). "FVIII(a)" includes natural allelic variants of FVIII(a) that may exist and occur from one individual to another. FVIII(a)

may be plasma-derived or recombinantly produced, using well known methods of production and purification. The degree and location of glycosylation, tyrosine sulfation and other post-translation modifications may vary, depending on the chosen host cell and its growth conditions.

Pharmaceutical compositions according to the present invention may comprise native or B domain-truncated FVIII molecules wherein the remaining domains correspond closely to the sequences as set forth in amino acid numbers 1-740 and 1649-2332 of SEQ ID NO: 3. In such molecules, as well as in FVIII comprising the full-length B domain amino acid sequence, mutations may be introduced. Amino acid modifications, such as substitutions, insertions, and deletions, may be introduced into the molecule in order to modify the binding capacity of FVIII with various other components such as low-density lipoprotein receptor-related protein (LRP) and related receptors, various other receptors, other coagulation factors, cell surfaces, introduction and/or abolishment of glycosylation sites, etc. Other mutations that do not abolish FVIII activity may also be accommodated in the FVIII molecules herein.

FVIII molecules herein (molecules/variants/derivatives/analogues/conjugates) are capable of functioning in the coagulation cascade in a manner that is functionally similar, or equivalent, to wt/endogenous FVIII, inducing the formation of FXa via interaction with FIXa on an activated platelet and supporting the formation of a blood clot. FVIII activity can be assessed in vitro using techniques well known in the art. Clot analyses, FX activation assays (often termed chromogenic assays), thrombin generation assays and whole blood thrombo-elastography are examples of such in vitro techniques. FVIII molecules according to the present invention have FVIII activity that is at least about 10%, at least about 20%, at least about 30%, at least about 40%, at least about 50%, at least about 60%, at least about 70%, at least about 80%, at least about 90%, 100% or even more than 100% of that of native human FVIII.

Endogenous full length FVIII is synthesized as a single-chain precursor molecule. Prior to secretion, the precursor is cleaved into the heavy chain and the light chain. Recombinant B domain-deleted or truncated FVIII can be produced by means of two different strategies. Either the heavy chain without the B-domain and the light chain are synthesized individually as two different polypeptide chains (two-chain strategy) or the B domain-deleted or truncated FVIII is synthesized as a single precursor polypeptide chain (single-chain strategy) that is cleaved into the heavy and light chains in the same way as the full-length FVIII precursor.

In a B domain-deleted or truncated FVIII precursor polypeptide, produced by the single-chain strategy, the heavy and light chain moieties are often separated by a linker. To minimize the risk of introducing immunogenic epitopes in the B domain-deleted FVIII, the sequence of the linker is preferably derived from the FVIII B-domain. In the B domain of full length FVIII, amino acid 1644-1648 constitutes this recognition site. The thrombin cleavage site leading to removal of the linker on activation of B domain-deleted FVIII is located in the heavy chain. Thus, the size and amino acid sequence of the linker is unlikely to influence its removal from the remaining FVIII molecule by thrombin activation. Deletion/truncation of the B domain is an advantage for production of FVIII. Nevertheless, parts of the B domain can be included in the linker without reducing the productivity. The negative effect of the B domain on productivity has not been attributed to any specific size or sequence of the B domain.

```
SEQ ID NO: 1: wt human FVIII (Ser750 residue shown in
bold and underline)
ATRRYYLGAVELSWDYMQSDLGELPVDARFPPRVPKSFPFNTSVVYKKTLFVEFT

DHLFNIAKPRPPWMGLLGPTIQAEVYDTVVITLKNMASHPVSLHAVGVSYWKASEGAEYDD

QTSQREKEDDKVFPGGSHTYVWQVLKENGPMASDPLCLTYSYLSHVDLVKDLNSGLIGALL

VCREGSLAKEKTQTLHKFILLFAVFDEGKSWHSETKNSLMQDRDAASARAWPKMHTVNGY

VNRSLPGLIGCHRKSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDLTDSEMDVVRF

DDDNSPSFIQIRSVAKKHPKTWVHYIAAEEEDWDYAPLVLAPDDRSYKSQYLNNGPQRIGR

KYKKVRFMAYTDETFKTREAIQHESGILGPLLYGEVGDTLLIIFKNQASRPYNIYPHGITDVRP

LYSRRLPKGVKHLKDFPILPGEIFKYKWTVTVEDGPTKSDPRCLTRYYSSFVNMERDLASGLI

GPLLICYKESVDQRGNQIMSDKRNVILFSVFDENRSWYLTENIQRFLPNPAGVQLEDPEFQA

SNIMHSINGYVFDSLQLSVCLHEVAYWYILSIGAQTDFLSVFFSGYTFKHKMVYEDTLTLFPF

SGETVFMSMENPGLWILGCHNSDFRNRGMTALLKVSSCDKNTGDYYEDSYEDISAYLLSKN

NAIEPRSFSQNSRHPSTRQKQFNATTIPENDIEKTDPWFAHRTPMPKIQNVSSSDLLMLLRQ

SPTPHGLSLSDLQEAKYETFSDDPSPGAIDSNNSLSEMTHFRPQLHHSGDMVFTPESGLQL

RLNEKLGTTAATELKKLDFKVSSTSNNLISTIPSDNLAAGTDNTSSLGPPSMPVHYDSQLDTT

LFGKKSSPLTESGGPLSLSEENNDSKLLESGLMNSQESSWGKNVSSTESGRLFKGKRAHG

PALLTKDNALFKVSISLLKTNKTSNNSATNRKTHIDGPSLLIENSPSVWQNILESDTEFKKVTP

LIHDRMLMDKNATALRLNHMSNKTTSSKNMEMVQQKKEGPIPPDAQNPDMSFFKMLFLPES

ARWIQRTHGKNSLNSGQGPSPKQLVSLGPEKSVEGQNFLSEKNKVVVGKGEFTKDVGLKE
```

-continued

```
MVFPSSRNLFLTNLDNLHENNTHNQEKKIQEEIEKKETLIQENVVLPQIHTVTGTKNFMKNLF

LLSTRQNVEGSYDGAYAPVLQDFRSLNDSTNRTKKHTAHFSKKGEEENLEGLGNQTKQIVE

KYACTTRISPNTSQQNFVTQRSKRALKQFRLPLEETELEKRIIVDDTSTQWSKNMKHLTPSTL

TQIDYNEKEKGAITQSPLSDCLTRSHSIPQANRSPLPIAKVSSFPSIRPIYLTRVLFQDNSSHL

PAASYRKKDSGVQESSHFLQGAKKNNLSLAILTLEMTGDQREVGSLGTSATNSVTYKKVEN

TVLPKPDLPKTSGKVELLPKVHIYQKDLFPTETSNGSPGHLDLVEGSLLQGTEGAIKWNEAN

RPGKVPFLRVATESSAKTPSKLLDPLAWDNHYGTQIPKEEWKSQEKSPEKTAFKKKDTILSL

NACESNHAIAAINEGQNKPEIEVTWAKQGRTERLCSQNPPVLKRHQREITRTTLQSDQEEID

YDDTISVEMKKEDFDIYDEDENQSPRSFQKKTRHYFIAAVERLWDYGMSSSPHVLRNRAQS

GSVPQFKKVVFQEFTDGSFTQPLYRGELNEHLGLLGPYIRAEVEDNIMVTFRNQASRPYSFY

SSLISYEEDQRQGAEPRKNFVKPNETKTYFWKVQHHMAPTKDEFDCKAWAYFSDVDLEKD

VHSGLIGPLLVCHTNTLNPAHGRQVTVQEFALFFTIFDETKSWYFTENMERNCRAPCNIQME

DPTFKENYRFHAINGYIMDTLPGLVMAQDQRIRWYLLSMGSNENIHSIHFSGHVFTVRKKEE

YKMALYNLYPGVFETVEMLPSKAGIWRVECLIGEHLHAGMSTLFLVYSNKCQTPLGMASGHI

RDFQITASGQYGQWAPKLARLHYSGSINAWSTKEPFSWIKVDLLAPMIIHGIKTQGARQKFS

SLYISQFIIMYSLDGKKWQTYRGNSTGTLMVFFGNVDSSGIKHNIFNPPIIARYIRLHPTHYSIR

STLRMELMGCDLNSCSMPLGMESKAISDAQITASSYFTNMFATWSPSKARLHLQGRSNAW

RPQVNNPKEWLQVDFQKTMKVTGVTTQGVKSLLTSMYVKEFLISSSQDGHQWTLFFQNGK

VKVFQGNQDSFTPVVNSLDPPLLTRYLRIHPQSWVHQIALRMEVLGCEAQDLY
```

The B domain in FVIII spans amino acids 741-1648 of SEQ ID NO: 1. The B domain is cleaved at several different sites, generating large heterogeneity in circulating plasma FVIII molecules. The exact function of the heavily glycosylated B domain is unknown. What is known is that the B domain is dispensable for FVIII activity in the coagulation cascade. Recombinant FVIII is thus frequently produced in the form of B domain-deleted/truncated variants. In a preferred embodiment, the FVIII molecule is produced by an expression vector encoding a FVIII molecule comprising a 21 amino acid residue L (linker) sequence with the following sequence: SEQ ID NO 2: SFSQNSRHPSQNPPVLKRHQR (the O-glycan is attached to the underlined S). Alternative preferred B domain linker sequences may lack one or more of the amino acid residues set forth in SEQ ID NO 2, e.g. the C-terminal R in SEQ ID NO 2. Preferred FVIII molecules are B domain deleted/truncated variants comprising an O-glycan attached to the Ser 750 residue shown in SEQ ID NO 1—optionally being conjugated to a polymeric (half-life extending) moiety via this O-glycan.

The inventors of the present invention have made the surprising observation that B domain deleted FVIII molecules according to the invention having a B domain of a size from about 100 to about 400 amino acids ((preferably 150-650, more preferably 150-600, more preferably 150-550, more preferably 150-500, more preferably 150-450, more preferably 150-400, more preferably 150-350, more preferably 200-700, more preferably 200-600, more preferably 200-500, more preferably 200-400, more preferably 200-300, and most preferably about 200 to 250) have a surprisingly high bioavailability in connection with extravascular (e.g. s.c.) administration compared to e.g. FVIII molecules having the entire B domain intact as well FVIII molecules having no or only a few amino acids (e.g. 15-30 amino acids) intact. Such molecules may or may not comprise the Ser750 residue according to SEQ ID NO 1. A simple and safe way of producing FVIII having improved bioavailability upon subcutaneous/intradermal administration is thus provided. It is plausible that the in vivo circulatory half-life of FVIII having B domains of 100 to about 400 amino acids may be prolonged by conjugating/fusing such variants with a half-life extending moiety. An example of a FVIII molecule comprising a 226 amino acid B domain is shown in SEQ ID NO 3:

```
SEQ ID NO 3: (226 amino acid B domain variant):
ATRRYYLGAVELSWDYMQSDLGELPVDARFPPRVPKSFPFNTSVVYKKTLFVEFT

DHLFNIAKPRPPWMGLLGPTIQAEVYDTVVITLKNMASHPVSLHAVGVSYWKASEGAEYDD

QTSQREKEDDKVFPGGSHTYVWQVLK

-continued
```
DDDNSPSFIQIRSVAKKHPKTWVHYIAAEEEDWDYAPLVLAPDDRSYKSQYLNNGPQRIGR

KYKKVRFMAYTDETFKTREAIQHESGILGPLLYGEVGDTLLIIFKNQASRPYNIYPHGITDVRP

LYSRRLPKGVKHLKDFPILPGEIFKYKWTVTVEDGPTKSDPRCLTRYYSSFVNMERDLASGLI

GPLLICYKESVDQRGNQIMSDKRNVILFSVFDENRSWYLTENIQRFLPNPAGVQLEDPEFQA

SNIMHSINGYVFDSLQLSVCLHEVAYWYILSIGAQTDFLSVFFSGYTFKHKMVYEDTLTLFPF

SGETVFMSMENPGLWILGCHNSDFRNRGMTALLKVSSCDKNTGDYYEDSYEDISAYLLSKN

NAIEPRSFSQNSRHPSTRQKQFNATTIPENDIEKTDPWFAHRTPMPKIQNVSSSDLLMLLRQ

SPTPHGLSLSDLQEAKYETFSDDPSPGAIDSNNSLSEMTHFRPQLHHSGDMVFTPESGLQL

RLNEKLGTTAATELKKLDFKVSSTSNNLISTIPSDNLAAGTDNTSSLGPPSMPVHYDSQLDTT

LFGKKSSPLTESGGPLSLSEENNDSKLLESGLMNSQESSWGKNVSHHHHHHSQNPPVLKR

HQREITRTTLQSDQEEIDYDDTISVEMKKEDFDIYDEDENQSPRSFQKKTRHYFIAAVERLW

DYGMSSSPHVLRNRAQSGSVPQFKKVVFQEFTDGSFTQPLYRGELNEHLGLLGPYIRAEVE

DNIMVTFRNQASRPYSFYSSLISYEEDQRQGAEPRKNFVKPNETKTYFWKVQHHMAPTKDE

FDCKAWAYFSDVDLEKDVHSGLIGPLLVCHTNTLNPAHGRQVTVQEFALFFTIFDETKSWYF

TENMERNCRAPCNIQMEDPTFKENYRFHAINGYIMDTLPGLVMAQDQRIRWYLLSMGSNEN

IHSIHFSGHVFTVRKKEEYKMALYNLYPGVFETVEMLPSKAGIWRVECLIGEHLHAGMSTLFL

VYSNKCQTPLGMASGHIRDFQITASGQYGQWAPKLARLHYSGSINAWSTKEPFSWIKVDLL

APMIIHGIKTQGARQKFSSLYISQFIIMYSLDGKKWQTYRGNSTGTLMVFFGNVDSSGIKHNIF

NPPIIARYIRLHPTHYSIRSTLRMELMGCDLNSCSMPLGMESKAISDAQITASSYFTNMFATW

SPSKARLHLQGRSNAWRPQVNNPKEWLQVDFQKTMKVTGVTTQGVKSLLTSMYVKEFLIS

SSQDGHQWTLFFQNGKVKVFQGNQDSFTPVVNSLDPPLLTRYLRIHPQSWVHQIALRMEVL

GCEAQDLY
```

Von Willebrand Factor (VWF) is a blood glycoprotein involved in hemostasis. It is deficient or defective in von Willebrand disease which is the most common hereditary bleeding disorder. VWF is a large multimeric glycoprotein present in blood plasma and produced constitutively in endothelium, megakaryocytes, and subendothelial connective tissue. The basic VWF monomer is a 2050 amino acid protein. Each monomer contains a number of specific domains with a specific function, including the TIL' or TIL'/E' domain (Zhou et al. Blood 2012; 120(2): 449-458) which binds to FVIII. FVIII is bound to VWF while inactive in circulation and is released from VWF by the action of thrombin. FVIII(a) not bound to VWF is rapidly cleared and/or degraded. It is shown herein, that full-length VWF does not have the ability to significantly increase bioavailability of extra-vascularly co-administered FVIII despite of its inherent FVIII protective effects.

The full length VWF molecule is thus a very complex protein. The prepro VWF consists of 2813 amino acid residues (SEQ ID NO 22). During secretion, the signal peptide from amino acid residue 1 to 22 and the propeptide from amino acid residue 23 to 763 are cleaved off, leaving a mature VWF of 2050 amino acid residues. The amino acid numbering is thus often based on the prepro VWF and amino acid S764 is thus the first amino acid in the mature molecule. The mature molecule is believed to contain 12 Asn-linked and 10 Thr/Ser linked oligosaccharide side chains. Furthermore this molecule can form dimers, trimers etc. with multimer molecule weight of up to several million Daltons. Different allelic VWF variants are found in human beings and it is thus understood that VWF fragments according to the present invention can be derived from any one of these naturally occurring variants.

The glycosylation heterogeneity, together with the multimer forming properties, of the full length molecule makes it quite challenging to construct an expression system and a downstream purification procedure for a pharmaceutical composition of VWF.

The understanding of the organization and the boundaries of domains in VWF is not yet complete. Only the so-called A domains are well characterized and their crystal structures determined. The chemical assignments of di-sulfides within VWF are limited. However, recent studies on homologies of domains in VWF to domains in and other proteins suggest that several disulfide bonds may be formed. The domain definition of VWF described in Zhou et al. Blood 2012; 120, 449-458 is used herein.

The present invention relates to VWF fragments that are preferably easier to produce than the full length molecule. VWF fragments according to the invention furthermore preferably have the ability to increase bioavailability of s.c. co-administered FVIII. VWF fragments according to the present invention comprise the at least the 15 N-terminal amino acids of the TIL' domain/subdomain (spanning amino acids 764-778 of SEQ ID NO 22) or the TIL' domain/subdomain (spanning amino acids 764-828 of SEQ ID NO 22 or amino acids 764-829 of SEQ ID NO 22) or the TIL'/E' domain/sub-domains (spanning amino acids 764-865 of SEQ ID NO 22) and have a size of less than 1500 amino acids, preferably less than 1400 amino acids, preferably less than 1300 amino acids, preferably less than 1200 amino acids, preferably less than 1100 amino acids, preferably less than 1000 amino acids, preferably less than 900 amino acids, preferably less than 800 amino acids, preferably less than 700 amino acids, preferably less than 600 amino acids, preferably less than 500 amino acids, preferably less than 400 amino acids, preferably less than 300 amino acids, preferably less than 275 amino acids, preferably less than 250 amino acids, preferably less than 225 amino acids preferably less than 200 amino acids, preferably less than 175 amino acids, preferably less than 150 amino acids, preferably less than 125 amino acids, preferably less than 100 amino acids, preferably less than 95 amino acids, preferably less than 90 amino acids, preferably less than 85 amino acids, or preferably less than 80 amino acids, or preferably less than 75 amino acids, or preferably less than 70 amino acids, or preferably less than 65 amino acids, or preferably less than 60 amino acids, or preferably less than 55 amino acids, or preferably less than 50 amino acids, or preferably less than 45 amino acids, or preferably less than 40 amino acids, or preferably less than 35 amino acids, or preferably less than 30 amino acids, or preferably less than 25 amino acids, or preferably less than 20 amino acids, or preferably less than 15 amino acids. VWF fragments according to the invention preferably comprise the TIL'/E'/D3 domains (where D3 is divided into subdomains VWD3-C8-3-TIL-3-E3) spanning amino acids 764-1250 or amino acids 764-1261 or amino acids 764-1268 of SEQ ID NO 22. VWF fragments according to the invention preferably comprise at least the 15 N-terminal amino acids of TIL', TIL' or TIL'/E' domains (amino acids 764-778, 764-828 or amino acids 764-865 of SEQ ID NO 22). VWF fragments according to the invention may comprise amino acids 764-1242 (SEQ ID NO 57) or amino acids 764-1482 (SEQ ID NO 58). VWF fragments according to the invention may furthermore contain fewer potentially antigenic regions. The molecular weight of VWF fragment dimers according to the present invention may—naturally—be about twice as high as for the monomeric fragments (Dimers according to the present invention may thus comprise up to about 2400 amino acids if the monomer size is 1200 amino acids).

Preferably, the VWF fragments according to the present invention comprise at least amino acids 764-828 (SEQ ID NO 4), or at least amino acids 764-865 (SEQ ID NO 5), or at least amino acids 764-1035 (SEQ ID NO 6), or at least amino acids 764-1041 (SEQ ID NO 7), or at least amino acids 764-1045 (SEQ ID NO 8), or at least amino acids 764-1128 (SEQ ID NO 9), or at least amino acids 764-1198 (SEQ ID no 10), or at least amino acids 764-1250 (SEQ ID NO 11), or at least amino acids 764-1261 (SEQ ID NO 14), or at least amino acids 764-1268 (SEQ ID NO 22), or at least amino acids 764-1242 (SEQ ID NO 57) or at least amino acid 764-1482 (SEQ ID NO 58).

VWF fragments comprising amino acids 764-1242 (SEQ ID NO 57) or amino acid 764-1482 (SEQ ID NO 58) may advantageously have a lower immunogenicity.

In an embodiment, the C1099 and/or the C1142 cysteines may be mutated in the VWF fragments according to the present invention. These cysteine residues are believed to be responsible for the oligomerization/dimerization of the VWF protein. VWF fragments with both cysteines intact may form dimers and homo-oligomers. Modifying both of these cysteines may lead to a product composed of monomer VWF fragments, whereas deletion of one or the other may lead to dimer VWF fragments or potentially to oligomer VWF fragments. Both of the above scenarios may lead to a simpler product purification procedure as compared to the full-length protein.

In another embodiment, both of the C1099 and C1142 cysteines are kept intact which may lead to a preferentially dimeric VWF fragment. There may be a safety advantage associated with the native sequences incl. the C1099 and the C1142 cysteines.

Surprisingly, co-formulation of FVIII and VWF fragments according to the invention demonstrate improved bioavailability compared to co-formulation of FVIII with a full length VWF molecule. The co-formulations according to the invention show increased bioavailability of Factor VIII when injected subcutaneously. VWF fragments according to the present invention comprise the D' domain (spanning amino acids 764-865/866 of SEQ ID NO: 22) which is thought to be the primary FVIII binding site where FVIII may dock onto D' by electrostatic dipole-dipole like interactions. VWF fragments according to the invention preferably comprise the D' domain and/or the D3-domain (the D3 domain spans amino acids 865/866-1250/1261/1268 of SEQ ID NO: 15). Based on the findings herein, it is possible that both the D' and the D'D3 domains have the ability to bind to FVIII. VWF fragments according to the invention do not to any significant degree (i.e. preferably less than 5%, more preferably less than 4%, preferably less than 3%, preferably less than 2%, more preferably less than 1%) form multimers (i.e., having more than two units, such as e.g. oligomers) because the cysteines (C1099 and C1142) essential for multimer assembly are not present or have been mutated/substituted. Some VWF fragments according to the present invention do furthermore not form dimers to any significant degree—in particular those wherein the C1099 and/or C1142 cysteines are not present.

In some cases, VWF fragments forming dimers may, however, also be useful in connection with the present invention—the TIL'/E'/D3/A1 dimer has e.g. been shown to have a higher FVIII affinity than the monomer. VWF fragment dimers may furthermore be a relatively homogenous product that can be produced relatively easily.

One advantage of the VWF fragments according to the invention is that it is easier to produce such compounds on an industrial scale as a relatively homogenous product due to the low degree of multimerization and due to the fact that the compounds are smaller compounds with fewer posttranslational modifications compared to full length VWF. This means that a high expression level is easier to obtain and/or purification will be less complex due to a less complex molecule. Also, production of recombinant peptides and proteins in simple organisms such as e.g. yeast is a faster and more inexpensive production method compared to production in mammalian cell lines—some VWF fragments according to the present invention can be produced in yeast.

VWF fragments according to the present invention can be in the form of one single VWF fragment (such as e.g. the entire TIL'/E'/D3/A1 region spanning amino acids 764-1459 in SEQ ID NO 22) or alternatively in the form of multiple groups of sequential amino acids from VWF fused together and thus deleting intermediary fragments (such as e.g. a "fusion" of the TIL' and the TIL'/E' domain spanning amino acids 764-828+764-865 in SEQ ID NO 22). Another example could be amino acids 764-828+1127-1197 in SEQ ID NO 22. VWF fragments according to the invention may alternatively be in the form of the repetitive elements. Homologous or heterologous "spacer" sequences may be introduced between the fused VWF fragments/elements (such as e.g. a multiple fusion of TIL'/E' domains such as e.g. TIL'/E'TIL'/E'TIL'/E'). VWF fragments according to the invention may also comprise one or more amino acid alternations (e.g. substitutions, deletions, additions) in the VWF derived sequence(s).

Bioavailability of FVIII in connection with extravascular co-administration of FVIII and VWF fragments according to the invention may be further improved by conjugating FVIII with at least one half-life extending moiety. It thus follows, that extra-vascular co-administration of VWF fragments comprising the TIL' and/or the TIL'/E' domains with a FVIII molecule conjugated with at least one half-life extending moiety is associated with a relatively high FVIII bioavailability.

Examples of VWF fragments according to the present invention (using the domain annotation from Zhou et al.) are shown below in SEQ ID NOs 4-21 and 57-58. TIL'/E'/VWD3 I, TIL'/E'/VWD3 II and TIL'/E'/VWD3 III denote three versions (different lengths) of TIL'/E'/VWD3.

```
SEQ ID NO 4: amino acids 764-828 (TIL'):
SLSCRPPMVKLVCPADNLRAEGLECTKTCQNYDLECMSMGCVSGCLCPPGMVRHENRCV

ALERCP

SEQ ID NO 5: amino acids 764-865 (TIL'/E'):
SLSCRPPMVKLVCPADNLRAEGLECTKTCQNYDLECMSMGCVSGCLCPPGMVRHENRCV

ALERCPCFHQG KEYAPGETVK IGCNTCVCQDRKWNCTDHVCDA

SEQ ID NO 6: amino acids 764-1035 (TIL'/E'/VWD3 I):
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKKRVTILVEGGEIELFDGEVNV

KRPMKDETHFEVVESGRYII LLLGKALSVVWDRHLSISVVLKQTYQEKVCGLCGNFDGIQ

NNDLTSSNLQ VEEDPVDFGN SWKVSSQCADTR

SEQ ID NO 7: amino acids 764-1041 (TIL'/E'/VWD3 II):
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQ VEEDPVDFGN SWKVSSQCADTRKVPLDS

SEQ ID NO 8: amino acids 764-1045 (TIL'/E'/VWD3 III):
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQ VEEDPVDFGN SWKVSSQCADTRKVPLDSSPAT

SEQ ID NO 9: amino acids 764-1128 (TIL'/E'/VWD3/C8-3) - Cysteine
1099 is marked with bold. This cysteine can be substituted to
another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKKRVTILVEGGEIELFDGEVNVK

RPMKDETHFEVVESGRYII LLLGKALSVVWDRHLSISVVLKQTYQEKVCGLCGNFDGIQ

NNDLTSSNLQVEEDPVDFGNSWKVSSQCADTRKVPLDSSPATCHNNIMKQTMVDSSCRILT

SDVFQDCNKLVDPEPYLDVCIYDTCSCESIGDCACFCDTIAAYAHVCAQHGKVVTWRTATL

CPQ

SEQ ID NO 10: amino acids 764-1198 (TIL'/E'/VWD3/C8-3/TIL-3) -
Cysteines 1099 and 1142 are marked with bold. One or both of
these cysteines can be substituted to another amino acid,
e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ
```

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPV

SEQ ID NO 11: amino acids 764-1250 (TIL'/E'/D3 I) - Cysteines
1099 and 1142 are marked with bold. One or both of these
cysteines can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDA

SEQ ID NO 12: amino acids 864-1250 (D3 I)- Cysteines 1099 and
1142 are marked with bold. One or both of these cysteines can
be substituted to another amino acid, e.g. Ser:
ATCSTIGMAHYLTFDGLKYLFPGECQYVLVQDYCGSNPGTFRILVGNKGCSHPSVKCKK

RVTILVEGGEIELFDGEVNVKRPMKDETHFEVVESGRYIILLLGKALSVVWDRHLSISVVLKQT

YQEKVCGLCGNFDGIQNNDLTSSNLQVEEDPVDFGNSWKVSSQCADTRKVPLDSSPATCH

NNIMKQTMVDSSCRILTSDVFQDCNKLVDPEPYLDVCIYDTCSCESIGDCACFCDTIAAYAHV

CAQHGKVVTWRTATLCPQSCEERNLRENGYECEWRYNSCAPACQVTCQHPEPLACPVQC

VEGCHAHCPPGKILDELLQTCVDPEDCPVCEVAGRRFASGKKVTLNPSDPEHCQICHCDVV

NLTCEACQEPGGL WPPTDA

SEQ ID NO 13: amino acids 864-1268 (D3 II) - Cysteines 1099
and 1142 are marked with bold. One or both of these cysteines
can be substituted to another amino acid, e.g. Ser:
ATCSTIGMAHYLTFDGLKYLFPGECQYVLVQDYCGSNPGTFRILVGNKGCSHPSVKCKK

RVTILVEGGEIELFDGEVNVKRPMKDETHFEVVESGRYIILLLGKALSVVWDRHLSISVVLKQT

YQEKVCGLCGNFDGIQNNDLTSSNLQVEEDPVDFGNSWKVSSQCADTRKVPLDSSPATCH

NNIMKQTMVDSSCRILTSDVFQDCNKLVDPEPYLDVCIYDTCSCESIGDCACFCDTIAAYAHV

CAQHGKVVTWRTATLCPQSCEERNLRENGYECEWRYNSCAPACQVTCQHPEPLACPVQC

VEGCHAHCPPGKILDELLQTCVDPEDCPVCEVAGRRFASGKKVTLNPSDPEHCQICHCDVV

NLTCEACQEPGGL VVPPTDAPVSPTTLYVEDISEPPLHD

SEQ ID NO 14: amino acids 764-1261(TIL'/E'/D3 II) - Cysteines 1099
and 1142 are marked with bold. One or both of these cysteines
can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKKRVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

-continued

DELLQTCVDPEDCPVCEVAGRRFASGKKVTLNPSDPEHCQ ICHCDVVNLTCEACQEPGGL

VVPPTDAPVSPTTLYVED

SEQ ID NO 15: amino acids 764-1264 (TIL'/E'/D3 III) - Cysteines
1099 and 1142 are marked with bold. One or both of these cysteines
can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDAPVSPTTLYVEDISEP

SEQ ID NO 16: amino acids 764-1268 (TIL'/E'/D3 IV) - Cysteines
1099 and 1142 are marked with bold. One or both of these cysteines
can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDAPVSPTTLYVEDISEPPLHD

SEQ ID NO 17: amino acids 764-1459 (TIL'/E'/D3/A1 I) - Cysteines
1099 and 1142 are marked with bold. One or both of these cysteines
can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDAPVSPTTLYVEDISEPPLHDFYCS RLLDLVFLLD GSSRLSEAEF EVLKAFVVDM

MERLRISQKWVRVAVVEYHDGSHAYIGLKDRKRPSELRRI ASQVKYAGSQVASTSEVLKY

TLFQIFSKIDRPEASRITLLLMASQEPQRMSRNFVRYVQGLKKKKVIVIPVGIGPHANLK

QIRLIEKQAPENKAFVLSSVDELEQQRDEI VSYLCD

SEQ ID NO 18: amino acids 764-1463 (TIL'/E'/D3/A1 II) - Cysteines
1099 and 1142 are marked with bold. One or both of these cysteines
can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

-continued

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDAPVSPTTLYVEDISEPPLHDFYCS RLLDLVFLLD GSSRLSEAEF EVLKAFVVDM

MERLRISQKWVRVAVVEYHDGSHAYIGLKDRKRPSELRRI ASQVKYAGSQVASTSEVLKY

TLFQIFSKIDRPEASRITLLLMASQEPQRMSRNFVRYVQGLKKKKVIVIPVGIGPHANLK

QIRLIEKQAPENKAFVLSSVDELEQQRDEI VSYLCDLAPE

SEQ ID NO 19: amino acids 764-1464 (TIL'/E'/D3/A1 III) - Cysteines 1099 and 1142 are marked with bold. One or both of these cysteines can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDAPVSPTTLYVEDISEPPLHDFYCS RLLDLVFLLD GSSRLSEAEF EVLKAFVVDM

MERLRISQKWVRVAVVEYHDGSHAYIGLKDRKRPSELRRI ASQVKYAGSQVASTSEVLKY

TLFQIFSKIDRPEASRITLLLMASQEPQRMSRNFVRYVQGLKKKKVIVIPVGIGPHANLK

QIRLIEKQAPENKAFVLSSVDELEQQRDEI VSYLCDLAPEA

SEQ ID NO 20: amino acids 764-1683 (TIL'/E'/D3/A1/A2) - Cysteines 1099 and 1142 are marked with bold. One or both of these cysteines can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDAPVSPTTLYVEDISEPPLHDFYCS RLLDLVFLLD GSSRLSEAEF EVLKAFVVDM

MERLRISQKWVRVAVVEYHDGSHAYIGLKDRKRPSELRRI ASQVKYAGSQVASTSEVLKY

TLFQIFSKIDRPEASRITLLLMASQEPQRMSRNFVRYVQGLKKKKVIVIPVGIGPHANLK

QIRLIEKQAPENKAFVLSSVDELEQQRDEIVSYLCDLAPEAPPPTLPPDMAQVTVGPLLGV

STLGPKRNSMVLDVAFVLEGSDKIGEADFNRSKEFMEEVIQRMDVGQDSIHVTVLQYSYMV

TVEYPFSEAQSKGDILQRVREIRYQGGNRTNTGLALRYLSDHSFLVSQGDREQAPNLVYMV

TGNPASDEIKRLPGDIQVVPIGVGPNANVQELERIGWPNAPILIQDFETLPREAPDLVLQRCC

SGE GLQIPTLSPA

SEQ ID NO 21: amino acids 764-1873 (TIL'/E'/D3/A1/A2/A3) - Cysteines 1099 and 1142 are marked with bold. One or both of these cysteines can be substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKK RVTILVEGGEIELFDGEVNV

KRPMKDETHFEVVESGRYII LLLGKALSVVWDRHLSISVVLKQTYQEKVCGLCGNFDGIQ

NNDLTSSNLQVEEDPVDFGN SWKVSSQCADTRKVPLDSSPATCHNNIMKQTMVDSSCRIL

TSDVFQDCNKLVDPEPYLDVCIYDTCSCESIGDCACFCDTIAAYAHVCAQHGKVVTWRTA

TLCPQSCEERNLRENGYECEWRYNSCAPACQVTCQHPEPLACPVQCVEGCHAHCPPGKIL

DELLQTCVDPEDCPVCEVAGRRFASGKKVTLNPSDPEHCQ ICHCDVVNLTCEACQEPGGL

VVPPTDAPVSPTTLYVEDISEPPLHDFYCS RLLDLVFLLD GSSRLSEAEF EVLKAFVVDM

MERLRISQKWVRVAVVEYHDGSHAYIGLKDRKRPSELRRI ASQVKYAGSQVASTSEVLKY

TLFQIFSKIDRPEASRITLLLMASQEPQRMSRNFVRYVQGLKKKKVIVIPVGIGPHANLKQIRLI

EKQAPENKAFVLSSVDELEQQRDEIVSYLCDLAPEAPPPTLPPDMAQVTVGPLLGVSTLG

PKRNSMVLDVAFVLEGSDKIGEADFNRSKEFMEEVIQRMDVGQDSIHVTVLQYSYMVTVEY

PFSEAQSKGDILQRVREIRYQGGNRTNTGLALRYLSDHSFLVSQGDREQAPNLVYMVTGNP

ASDEIKRLPGDIQVVPIGVGPNANVQELERIGWPNAPILIQDFETLPREAPDLVLQRCCSGEG

LQIPTLSPAPDCSQPLDVILLLDGSSSFPASYFDEMKSFAKAFISKANIGPRLTQVSVL

QYGSITTIDVPWNVVPEKAHLLSLVDVMQREGGPSQIGDALGFAVRYLTSEMHGARPGAS

KAVVILVTDVSVDSVDAAADAARSNRVTVFPIGIGDRYDAAQLRILAGPAGDSNVVKLQRIED

LPTMVTLGNSFLHKLCS

SEQ ID NO 22: wild-type human VWF according to the UniProtKB/Swiss-Prot database (entry P04275) - cysteine residues at positions 1099 and 1142 are marked with bold:
MIPARFAGVLLALALILPGTLCAEGTRGRSSTARCSLFGSDFVNTFDGSMYSFAGYCSYLLA

GGCQKRSFSIIGDFQNGKRVSLSVYLGEFFDIHLFVNGTVTQGDQRVSMPYASKGLYLETEA

GYYKLSGEAYGFVARIDGSGNFQVLLSDRYFNKTCGLCGNFNIFAEDDFMTQEGTLTSDPY

DFANSWALSSGEQWCERASPPSSSCNISSGEMQKGLWEQCQLLKSTSVFARCHPLVDPE

PFVALCEKTLCECAGGLECACPALLEYARTCAQEGMVLYGWTDHSACSPVCPAGMEYRQC

VSPCARTCQSLHINEMCQERCVDGCSCPEGQLLDEGLCVESTECPCVHSGKRYPPGTSLS

RDCNTCICRNSQWICSNEECPGECLVTGQSHFKSFDNRYFTFSGICQYLLARDCQDHSFSI

VIETVQCADDRDAVCTRSVTVRLPGLHNSLVKLKHGAGVAMDGQDVQLPLLKGDLRIQHTV

TASVRLSYGEDLQMDWDGRGRLLVKLSPVYAGKTCGLCGNYNGNQGDDFLTPSGLAEPR

VEDFGNAWKLHGDCQDLQKQHSDPCALNPRMTRFSEEACAVLTSPTFEACHRAVSPLPYL

RNCRYDVCSCSDGRECLCGALASYAAACAGRGVRVAWREPGRCELNCPKGQVYLQCGTP

CNLTCRSLSYPDEECNEACLEGCFCPPGLYMDERGDCVPKAQCPCYYDGEIFQPEDIFSDH

HTMCYCEDGFMHCTMSGVPGSLLPDAVLSSPLSHRSKRSLSCRPPMVKLVCPADNLRAEG

LECTKTCQNYDLECMSMGCVSGCLCPPGMVRHENRCVALERCPCFHQGKEYAPGETVKI

GCNTCVCQDRKWNCTDHVCDATCSTIGMAHYLTFDGLKYLFPGECQYVLVQDYCGSNPGT

FRILVGNKGCSHPSVKCKKRVTILVEGGEIELFDGEVNVKRPMKDETHFEVVESGRYIILLLG

KALSVVWDRHLSISVVLKQTYQEKVCGLCGNFDGIQNNDLTSSNLQVEEDPVDFGNSWKVS

SQCADTRKVPLDSSPATCHNNIMKQTMVDSSCRILTSDVFQDCNKLVDPEPYLDVCIYDTCS

CESIGDCACFCDTIAAYAHVCAQHGKVVTWRTATLCPQSCEERNLRENGYECEWRYNSCA

-continued

PACQVTCQHPEPLACPVQCVEGCHAHCPPGKILDELLQTCVDPEDCPVCEVAGRRFASGK

KVTLNPSDPEHCQICHCDVVNLTCEACQEPGGLVVPPTDAPVSPTTLYVEDISEPPLHDFYC

SRLLDLVFLLDGSSRLSEAEFEVLKAFVVDMMERLRISQKWVRVAVVEYHDGSHAYIGLKDR

KRPSELRRIASQVKYAGSQVASTSEVLKYTLFQIFSKIDRPEASRITLLLMASQEPQRMSRNF

VRYVQGLKKKKVIVIPVGIGPHANLKQIRLIEKQAPENKAFVLSSVDELEQQRDEIVSYLCDLA

PEAPPPTLPPDMAQVTVGPGLLGVSTLGPKRNSMVLDVAFVLEGSDKIGEADFNRSKEFME

EVIQRMDVGQDSIHVTVLQYSYMVTVEYPFSEAQSKGDILQRVREIRYQGGNRTNTGLALR

YLSDHSFLVSQGDREQAPNLVYMVTGNPASDEIKRLPGDIQVVPIGVGPNANVQELERIGW

PNAPILIQDFETLPREAPDLVLQRCCSGEGLQIPTLSPAPDCSQPLDVILLLDGSSSFPASYFD

EMKSFAKAFISKANIGPRLTQVSVLQYGSITTIDVPWNVVPEKAHLLSLVDVMQREGGPSQIG

DALGFAVRYLTSEMHGARPGASKAVVILVTDVSVDSVDAAADAARSNRVTVFPIGIGDRYDA

AQLRILAGPAGDSNVVKLQRIEDLPTMVTLGNSFLHKLCSGFVRICMDEDGNEKRPGDVWT

LPDQCHTVTCQPDGQTLLKSHRVNCDRGLRPSCPNSQSPVKVEETCGCRWTCPCVCTGS

STRHIVTFDGQNFKLTGSCSYVLFQNKEQDLEVILHNGACSPGARQGCMKSIEVKHSALSVE

LHSDMEVTVNGRLVSVPYVGGNMEVNVYGAIMHEVRFNHLGHIFTFTPQNNEFQLQLSPKT

FASKTYGLCGICDENGANDFMLRDGTVTTDWKTLVQEWTVQRPGQTCQPILEEQCLVPDS

SHCQVLLLPLFAECHKVLAPATFYAICQQDSCHQEQVCEVIASYAHLCRTNGVCVDWRTPD

FCAMSCPPSLVYNHCEHGCPRHCDGNVSSCGDHPSEGCFCPPDKVMLEGSCVPEEACTQ

CIGEDGVQHQFLEAWVPDHQPCQICTCLSGRKVNCTTQPCPTAKAPTCGLCEVARLRQNA

DQCCPEYECVCDPVSCDLPPVPHCERGLQPTLTNPGECRPNFTCACRKEECKRVSPPSCP

PHRLPTLRKTQCCDEYECACNCVNSTVSCPLGYLASTATNDCGCTTTTCLPDKVCVHRSTI

YPVGQFWEEGCDVCTCTDMEDAVMGLRVAQCSQKPCEDSCRSGFTYVLHEGECCGRCL

PSACEVVTGSPRGDSQSSWKSVGSQWASPENPCLINECVRVKEEVFIQQRNVSCPQLEVP

VCPSGFQLSCKTSACCPSCRCERMEACMLNGTVIGPGKTVMIDVCTTCRCMVQVGVISGF

KLECRKTTCNPCPLGYKEENNTGECCGRCLPTACTIQLRGGQIMTLKRDETLQDGCDTHFC

KVNERGEYFWEKRVTGCPPFDEHKCLAEGGKIMKIPGTCCDTCEEPECNDITARLQYVKVG

SCKSEVEVDIHYCQGKCASKAMYSIDINDVQDQCSCCSPTRTEPMQVALHCTNGSVVYHEV

LNAMECKCSPRKCSK

SEQ ID NO 57: amino acids 764-1242 - Cysteines 1099 and 1142
are marked with bold. One or both of these cysteines can be
substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

YLFPGECQYVLVQDYCGSNPGTFRILVGNKGCSHPSVKCKKRVTILVEGGEIELFDGEVNVK

RPMKDETHFEVVESGRYIILLLGKALSVVWDRHLSISVVLKQTYQEKVCGLCGNFDGIQNND

LTSSNLQVEEDPVDFGNSWKVSSQCADTRKVPLDSSPATCHNNIMKQTMVDSSCRILTSDV

FQDCNKLVDPEPYLDVCIYDTCSCESIGDCACFCDTIAAYAHVCAQHGKVVTWRTATLCPQ

SCEERNLRENGYECEWRYNSCAPACQVTCQHPEPLACPVQCVEGCHAHCPPGKILDELLQ

TCVDPEDCPVCEVAGRRFASGKKVTLNPSDPEHCQ ICHCDVVNLTCEACQEPGG

SEQ ID NO 58: amino acids 764-1482 - Cysteines 1099 and 1142
are marked with bold. One or both of these cysteines can be
substituted to another amino acid, e.g. Ser:
SLSCRPPMVKLVCPADNLRAEGLECTKTCQNYDLECMSMGCVSGCLCPPGMVRHENRCV

ALERCPCFHQGKEYAPGETVKIGCNTCVCQDRKWNCTDHVCDATCSTIGMAHYLTFDGLK

-continued
```
YLFPGECQYVLVQDYCGSNPGTFRILVGNKGCSHPSVKCKKRVTILVEGGEIELFDGEVNVK

RPMKDETHFEVVESGRYIILLLGKALSVVWDRHLSISVVLKQTYQEKVCGLCGNFDGIQNND

LTSSNLQVEEDPVDFGNSWKVSSQCADTRKVPLDSSPATCHNNIMKQTMVDSSCRILTSDV

FQDCNKLVDPEPYLDVCIYDTCSCESIGDCACFCDTIAAYAHVCAQHGKVVTWRTATLCPQ

SCEERNLRENGYECEWRYNSCAPACQVTCQHPEPLACPVQCVEGCHAHCPPGKILDELLQ

TCVDPEDCPVCEVAGRRFASGKKVTLNPSDPEHCQICHCDVVNLTCEACQEPGGLVVPPT

DAPVSPTTLYVEDISEPPLHDFYCSRLLDLVFLLDGSSRLSEAEFEVLKAFVVDMMERLRISQ

KWVRVAVVEYHDGSHAYIGLKDRKRPSELRRIASQVKYAGSQVASTSEVLKYTLFQIFSKID

RPEASRITLLLMASQEPQRMSRNFVRYVQGLKKKKVIVIPVGIGPHANLKQIRLIEKQAPENK

AFVLSSVDELEQQRDEIVSYLCDLAPEAPPPTLPPDMAQVTVGPGL
```

FVIII Molecules/Variants/Derivatives/Analogues: The term "FVIII" as used herein, is intended to designate any FVIII molecule having FVIII activity, incl. wt FVIII, B domain deleted/truncated FVIII molecules, variants of FVIII exhibiting substantially the same or improved biological activity relative to wt FVIII and FVIII-related polypeptides, in which one or more of the amino acids of the parent peptide have been chemically modified, e.g. by protein:protein fusion, alkylation, PEGylation, HESylation, PASylation, PSAylation, acylation, ester formation or amide formation or the like (conjugated to a half-life extending moiety).

Half-Life Extending Moieties/Protractive Groups: The term "half-life extending moieties" is herein understood to refer to one or more chemical groups, e.g. a hydrophilic polymer, such as e.g. PEG and/or a polysaccharide covalently attached to FVIII via e.g. —SH, —OH, —COOH, —CONH2, —NH2, or one or more N- and/or O-glycan structures that can increase in vivo circulatory half-life when conjugated to these proteins. Examples of protractive groups/half-life extending moieties suitable for being conjugated to FVIII in connection with the present invention include: Biocompatible fatty acids and derivatives thereof, Hydroxy Alkyl Starch (HAS) e.g. Hydroxy Ethyl Starch (HES), Poly Ethylene Glycol (PEG), Poly (Glyx-Sery)n (HAP), Hyaluronic acid (HA), Heparosan polymers (HEP), Phosphorylcholine-based polymers (PC polymer), Fleximers, Dextran, Polysialic acids (PSA), an Fc domain, an Fc receptor, Transferrin, Albumin, Elastin like peptides, XTEN polymers, Albumin binding peptides, a CTP peptide, and any combination thereof. In general, conjugation of FVIII with one or more half-life extending moieties (such as e.g. hydrophilic polymers) generally have a better bioavailability in connection with s.c./intradermal co-administration with VWF fragments according to the invention as compared with FVIII with no half-life extending moieties.

PEGylated FVIII molecules in connection with the present invention may have one or more polyethylene glycol (PEG) molecules attached to any part of the FVIII protein including any amino acid residue or carbohydrate moiety. Chemical and/or enzymatic methods can be employed for conjugating PEG or other polymeric groups (half-life extending moieties) to a glycan on FVIII. An example of an enzymatic conjugation process is described e.g. in WO03031464. The glycan may be naturally occurring or it may be inserted via e.g. insertion of an N-linked and/or O-linked glycan using methods well known in the art. "Cysteine-PEGylated FVIII" according to the present invention have one or more PEG molecules conjugated to a sulfhydryl group of a cysteine present in FVIII. "Cysteine-acylated FVIII" according to the present invention have one or more hydrophobic half-life extending moieties (e.g. fatty acids) conjugated to a sulfhydryl group of a cysteine in FVIII—this cysteine residue may be introduced by genetic engineering or a part of the native amino acid sequence. It is furthermore possible to link half-life extending moieties to other amino acid residues.

Fusion Proteins: Fusion proteins according to the present invention are proteins created through the in-frame joining of two or more DNA sequences which originally encoded FVIII and the fusion partner. Translation of the fusion protein DNA sequence will result in a single protein sequence which may have functional properties derived from each of the original proteins or peptides. DNA sequences encoding fusion proteins may be created artificially by standard molecular biology methods such as overlapping PCR or DNA ligation and the assembly is performed excluding the stop codon in the first 5'-end DNA sequence while retaining the stop codon in the 3' end DNA sequence. The resulting fusion protein DNA sequence may be inserted into an appropriate expression vector that supports the heterologous fusion protein expression in a standard host organism.

Fusion proteins may contain a linker or spacer peptide sequence that separates the protein or peptide parts which define the fusion protein. The linker or spacer peptide sequence may facilitate the correct folding of the individual protein or peptide parts and may make it more likely for the individual protein or peptide parts to retain their individual functional properties. Linker or spacer peptide sequences may be inserted into fusion protein DNA sequences during the in frame assembly of the individual DNA fragments that make up the complete fusion protein DNA sequence i.e. during overlapping PCR or DNA ligation. Examples of fusion proteins comprising FVIII and a fusion partner are shown in WO2011101284.

Fc Fusion Protein: The term "Fc fusion protein" is herein meant to encompass FVIII fused to an Fc domain that can be derived from any antibody isotype. An IgG Fc domain will often be preferred due to the relatively long circulatory half-life of IgG antibodies. The Fc domain may furthermore be modified in order to modulate certain effector functions such as e.g. complement binding and/or binding to certain Fc receptors. Fusion of FVIII with an Fc domain, which has the capacity to bind to FcRn receptors, will generally result in a prolonged in vivo circulatory half-life. Mutations in positions 234, 235 and 237 in an IgG Fc domain will generally result in reduced binding to the FcγRI receptor and possibly also the FcγRIIa and the FcγRIII receptors. These mutations do not alter binding to the FcRn receptor, which promotes a long circulatory in vivo half-life by an endocytic recycling pathway. Preferably, a modified IgG Fc domain of a fusion protein according to the invention comprises one or more of the following mutations that will result in decreased affinity to certain Fc receptors (L234A, L235E, and G237A) and in reduced C1q-mediated complement fixation (A330S and P331S), respectively. Alternatively, the Fc domain may be an IgG4 Fc domain, preferably comprising the S241P/S228P mutation.

Bioavailability (of FVIII): The term "Bioavailability" describes the percentage of compound absorbed to the blood after extravascular is calculated as the Area under the concentration time curves after extravascular dosing of the compound. This is calculated from the Area under the concentration curves of FVIII after s.c. administration divided by the dose, relatively to the area under the concentrations curve divided by the dose of the same FVIII compound, dosed i.v. According to the present invention, the bioavailability of FVIII molecules (in connection with subcutaneous/intradermal co-administration of FVIII and VWF fragments according to the invention) is at least 3%, preferably at least 5%, preferably at least 6%, preferably at least 7%, preferably at least 8%, preferably at least 9%, preferably at least 10%, preferably at least 11%, preferably at least 12%, preferably at least 13%, preferably at least 14%, preferably at least 15%, preferably at least 16%, preferably at least 17%, preferably at least 18%, preferably at least 19%, preferably at least 20%, preferably at least 21%, preferably at least 22%, preferably at least 23%, preferably at least 24%, preferably at least 25%, preferably at least 26%, preferably at least 27%, preferably at least 28%, preferably at least 29%, preferably at least 30%, preferably at least 31%, preferably at least 32%, preferably at least 33%, preferably at least 34%, preferably at least 35%, preferably at least 36%, preferably at least 37%, preferably at least 38%, preferably at least 39%, preferably at least 40%, preferably at least 41%, preferably at least 42%, preferably at least 43%, preferably at least 44%, preferably at least 45%, preferably at least 46%, preferably at least 47%, preferably at least 48%, preferably at least 49%, preferably at least 50%, preferably at least 55%, preferably at least 60%, preferably at least 65%, preferably at least 70%, and most preferably at least 75%. Bioavailability can be measured as described herein. Preferably, the FVIII bioavailability (FVIII antigen and/or activity) of formulations according to the invention will be high enough to exert prophylactic effects under conditions with normal activity when such formulations are administered extravascularly (e.g. subcutaneously or intradermally) e.g. once or twice a day or once, twice or three times a week. Preferably, FVIII dosages are comparable with those used in connection with I.V. administration of FVIII, preferably twice as high, and more preferably three times as high, more preferably four times as high, more preferably about 10 times as high, more preferably about 15 times as high, more preferably about 20 times as high, and most preferably about 25 times as high. Safety and cost considerations may be considered in connection with dosage determinations.

Saturation of FVIII with VWF Fragments according to the invention: saturation of FVIII with VWF fragment/the relative amount of FVIII bound to or in complex with VWF/the amount of FVIII bound to VWF divided by the total amount of FVIII. This calculation is based on the KD value of the binding between FVIII and the protein. For FVIII binding to VWF fragments, the measured KI values are used as KD.

The following (quadratic) equations can be used to calculate the concentration of bound FVIII (A) to another protein (B) from the total concentrations $[A]_t$, $[B]_t$.

$$K_D = \frac{[A] \times [B]}{[AB]}$$

$$[A] = [A]_t - [AB]$$

$$[B] = [B]_t - [AB]$$

$$[AB]^2 - (K_D + [A]_t + [B]_t) \times [AB] + [A]_t \times [B]_t = 0$$

$$\alpha \times [AB]^2 + \beta \times [AB] + \delta = 0$$

$$\alpha = 1, \beta = -(K_D + [A]_t + [B]_t), \delta = [A]_t \times [B]_t$$

$$[AB] = \frac{-\beta \pm \sqrt{\beta^2 - 4 \times \alpha \times \delta}}{2 \times \alpha}$$

Pharmaceutical Compositions: The present invention provides compositions comprising VWF fragments and preferably also FVIII.

Accordingly, one object of the invention is to provide a pharmaceutical composition comprising a FVIII molecule present in a concentration from 40 IU/ml to 25,000 IU/ml, and wherein said composition has a pH from 2.0 to 10.0. In a preferred embodiment, the FVIII molecules are co-administered together with VWF fragments. In another embodiment, the pharmaceutical composition comprises (i) a FVIII molecule and (ii) a VWF fragment; in one embodiment thereof, the pharmaceutical composition is an aqueous liquid, ready-to use composition, in another embodiment, the composition is a freeze-dried composition that should be dissolved before use. Formulations of FVIII, particularly liquid formulations, are stabilised against degradation by addition of VWF fragments. Pharmaceutical compositions according to the invention may thus comprise FVIII in a concentration of from 40 IU/ml to 25,000 IU/ml, such as e.g. from 50-25,000 IU/ml, 100-25,000 IU/ml, 250-25,000 IU/ml, 500-25,000 IU/ml, 1000-25,000 IU/ml, 2000-25,000 IU/ml, 3000-25,000 IU/ml, 4000-25,000 IU/ml, 5000-25,000 IU/ml, 6000-25,000, 7000-25,000, 8000-25,000, 9000-25,000, 10,000-25,000 IU/ml, 50-20,000 IU/ml, 100-20,000 IU/ml, 250-20,000 IU/ml, 500-20,000 IU/ml, 1000-20,000 IU/ml, 2000-20,000 IU/ml, 3000-20,000 IU/ml, 4000-20,000 IU/ml, 5000-20,000 IU/ml, 6000-20,000 IU/ml, 7000-20,000 IU/ml, 8000-20,000 IU/ml, 9000-20,000 IU/ml, 10,000-20,000 IU/ml, 50-15,000 IU/ml, 100-15,000 IU/ml, 250-15,000 IU/ml, 500-15,000 IU/ml, 1000-15,000 IU/ml, 2000-15,000 IU/ml, 3000-15,000 IU/ml, 4000-15,000 IU/ml, 5000-15,000 IU/ml, 6000-15,000 IU/ml, 7000-15,000 IU/ml, 8000-15,000 IU/ml, 9000-15,000 IU/ml, 10,000-15,000 IU/ml, 50-10,000 IU/ml, 100-10,000 IU/ml, 250-10,000 IU/ml, 500-10,000 IU/ml, 1000-10,000 IU/ml, 2000-10,000 IU/ml, 3000-10,000 IU/ml, 4000-10,000 IU/ml, 5000-10,000 IU/ml, 50-5000 IU/ml, 100-5000 IU/ml, 250-5000 IU/ml, 500-5000 IU/ml, and 1000-5000 IU/ml. Compositions according to the invention may further comprise one or more pharmaceutically acceptable excipients such as e.g. a buffer system, a preservative, a tonicity agent, a chelating agent, a stabilizer, or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19th edition, 1995.

In one embodiment, the pharmaceutical composition is an aqueous composition. Such a composition is typically a solution or a suspension, but may also include colloids, dispersions, emulsions, and multi-phase materials. The term "aqueous composition" is defined as a composition comprising at least 50% w/w water. Likewise, the term "aqueous solution"

is defined as a solution comprising at least 50% w/w water, and the term "aqueous suspension" is defined as a suspension comprising at least 50% w/w water. In one embodiment, the pharmaceutical composition is an aqueous solution; in another embodiment it is a liquid, ready-to-use composition.

In another embodiment, the pharmaceutical composition is a freeze-dried composition, to which the physician or the patient adds solvents and/or diluents prior to use.

In one embodiment, the pharmaceutical compositions according to the present invention are suitable for extravascular administration (e.g. s.c. or intradermal administration) in prophylactic/therapeutic treatment of blood clotting diseases. In another embodiment, the pharmaceutical composition is suitable for intravenous administration.

In one embodiment, the pharmaceutical composition according to the invention is a pharmaceutical composition for intravenous administration; in further embodiments thereof, the pharmaceutical composition is (i) a freeze-dried composition or (ii) a liquid composition.

"Ratio of FVIII:VWF": According to the present invention, preferred ratios of FVIII and VWF/VWF fragment include FVIII/VWF ratios (molar ratios) from 0.5:1 to 1:50, such as e.g. 1:1 to 1:50, such as e.g. 1:1 to 1:25, such as e.g. 1:1 to 1:20, or 1:1 to 1:15, or 1:1 to 1:10, or 1:1 to 1:7.5, or 1:7 to 1:8, or 1:6 to 1:8, or 1:6 to 1:9, or 1:5 to 1:10. Preferred ratios thus include: 1:1, 1:2, 1:3, 1:4, 1:5.1:5.5; 1:6; 1:6.5, 1:7; 1:7.1; 1:7.2; 1:7.3; 1:7.4; 1:7.5; 1:7.6; 1:7.7; 1:7.8; 1:7.9, 1:8, 1:9, 1:10, 1:15, 1:20, 1:25, 1:30, 1:35, 1:40, 1:45, and 1:50. Preferred ratios include: 0.5:1; 0.6:1; 0.7:1; 0.8:1; 0.9:1; 1:1; 1.1:1; 1.2:1; 1.3:3; 1.4:1, and 1.5:1. A molar ratio close to 1:1 generally has the advantage of minimizing the required amount of active substance. The optimal ratio between FVIII and VWF fragment in a co-formulation mixture may be determined by calculating the amount of bound FVIII:VWF at certain protein concentrations based on the binding affinity to the VWF variant for the FVIII species in question. The binding affinity can be determined e.g. by ELISA, SPR or by ITC.

"Haemophilia": Haemophilia/hemophilia/blood clotting diseases is a group of hereditary genetic disorders that impair the body's ability to control blood clotting or coagulation ("bleeding disorders"), which is used to stop bleeding when a blood vessel is broken. Haemophilia A (clotting factor VIII deficiency) is the most common form of the disorder, present in about 1 in 5,000-10,000 male births. In connection with the present invention, the term "haemophilia" encompasses von Willebrand disease.

List of Embodiments:
1. A VWF fragment comprising up to 1500, 1400, 1300, or 1200, wherein said VWF fragment comprises the TIL' domain. Said fragment may comprise different or repetitive VWF sequences joined by peptide bonds.
2. A VWF fragment according to the invention, wherein said fragment comprises the TIL' and the E' domains.
3. A VWF fragment consisting of the TIL' or the TIL'/E' domains.
4. A VWF fragment (according to the invention), wherein said fragment comprises the amino acid sequence according to any one of SEQ ID NO 4, 5, 6, 7, 8, 9, 10, 11, 12, 13, 14, 15, 16, 17, 18, 19, 20, 21, 57 or 58.
5. A VWF fragment according to the invention, wherein said VWF fragment does not comprise cysteine residues at position(-s) 1099 and/or 1142 of SEQ ID NO 22. These cysteine residue(-s) can be deleted by amino acid substitution and/or deletion.
6. A VWF fragment according to the invention, wherein said fragment comprises SEQ ID NO 9, wherein the 1099 Cysteine residue is substituted with another amino acid, such as e.g. Histidine, Alanine, Isoleucine Arginine, Leucine, Asparagine, Lysine, Aspartic acid, Methionine, Phenylalanine, Glutamic acid, Threonine, Glutamine, Tryptophan, Glycine, Valine, Proline, Serine, Taurine, and Tyrosine.
7. A VWF fragment according to the invention, wherein the 1099 cysteine residue is substituted with Serine.
8. A VWF fragment according to the invention, wherein said fragment comprises an amino acid sequence selected from the list consisting of: SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 57 and SEQ ID NO 58 wherein the 1099 and the 1142 cysteine residues are substituted with another amino acid, such as e.g. Histidine, Alanine, Isoleucine Arginine, Leucine, Asparagine, Lysine, Aspartic acid, Methionine, Phenylalanine, Glutamic acid, Threonine, Glutamine, Tryptophan, Glycine, Valine, Proline, Serine, Taurine, and/or Tyrosine.
9. A VWF fragment according to the invention, wherein the 1099 and the 1142 cysteine residues are substituted with serine.
10. A pharmaceutical composition comprising a VWF fragment according to the invention, wherein less than 10%, preferably less than 9%, preferably less than 8%, preferably less than 7%, preferably less than 6%, preferably less than 5%, preferably less than 4%, preferably less than 3%, preferably less than 2%, preferably less than 1% of said VWF fragment are in the form of oligomers and/or multimers.
11. A VWF fragment according to the invention, wherein said VWF fragment is part of a dimer. The percentage of dimer formation may be at least 5%, preferably at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, most preferably at least 95%.
12. A pharmaceutical composition comprising FVIII and a VWF fragment, wherein FVIII bioavailability is at least 5% following extravascular (e.g. sub-cutaneous/intradermal) administration of said pharmaceutical formulation.
13. A pharmaceutical composition comprising FVIII and a VWF fragment, wherein FVIII bioavailability is at least 5% following extravascular (e.g. sub-cutaneous/intradermal) administration of said pharmaceutical formulation, wherein the ratio of FVIII and VWF fragment is about 0.5:1-1:50. Preferably said ratio is about 0.5:1, 1:1, or 1:2.
14. A VWF fragment, wherein the amino acid sequence of said VWF fragment comprises or consists of an amino acid sequence selected from the list consisting of: SEQ ID NO 4, SEQ ID NO 5, SEQ ID NO 6, SEQ ID NO 7, SEQ ID NO 8, SEQ ID NO 9, SEQ ID NO 10, SEQ ID NO 11 SEQ ID NO 12, SEq ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 57 and SEQ ID NO 58.
15. A pharmaceutical composition comprising: (i) a VWF fragment according to the invention; and (ii) FVIII, preferably recombinant FVIII. Alternatively, said composition may comprise two, three, four, five or more different VWF fragments according to the invention and/or two, three, four, or five different FVIII molecules.

16. A pharmaceutical composition according to the invention, wherein said FVIII molecule comprises a truncated B domain at a size of 5-700 amino acids, such as e.g. 5-500, 5-400, 5-300, 5-200, 5-100, 5-50, 5-40, 5-30, 5-25, 5-20, 10-700, 10-500, 10-400, 10-300, 10-200, 10-100, 10-50, 10-40, 10-30, 10-20, 20-700, 20-500, 20-400, 20-300, 20-200, 20-100, 20-50, 20-25, 50-700, 50-500, 50-400, 50-300, 50-200, 50-100, 100-700, 100-500, 100-400, 100-300, 100-200, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 75, or 100 amino acids 17. A pharmaceutical composition according to the invention, wherein the amino acid sequence of said truncated B domain is derived from the wt FVIII B domain amino acid sequence.

18. A pharmaceutical composition according to the invention, wherein said FVIII molecule is a B domain truncated FVIII molecule, wherein said B domain comprises an O-glycan linked to the Ser 750 amino acid residue as set forth in SEQ ID NO 1. Preferably, said FVIII molecule comprises one O-linked glycan in the truncated B domain, wherein said O-linked glycan is attached to the Ser 750 residue as set forth in SEQ ID NO 1.

19. A pharmaceutical composition according to the invention, wherein said FVIII molecule comprises a B domain having the amino acid sequence as set forth in SEQ ID NO 2. Alternatively, one or more amino acids in the B domain are deleted from SEQ ID NO 2, such as e.g. the N-terminal Ser residue and/or the C-terminal Arg residue.

20. A pharmaceutical composition according to the invention, wherein the amino acid sequence of the FVIII B domain comprises or consists of an amino acid sequence selected from the group consisting of: amino acids 741-857+1637-1648; amino acids 741-914+1637-1648; amino acids 741-954+1637-1648; amino acids 741-965+1637-1648; amino acids 741-965+1637-1648; amino acids 741-1003+1637-1648; amino acids 741-1003+1637-1648; amino acids 741-1020+1637-1648; amino acids 741-1079+1637-1648; amino acids 741-1206+1637-1648; amino acids 741-1261+1637-1648; amino acids 741-1309+1637-1648; amino acids 741-914+1637-1648; amino acids 741-954+1637-1648; amino acids 741-968+1637-1648; amino acids 741-1003+1637-1648; amino acids 741-1018+1637-1648; amino acids 741-1070+1637-1648; amino acids 741-1230+1637-1648; amino acids 741-1301+1637-1648; amino acids 741-965+1637-1648; amino acids 741-965+1637-1648; amino acids 741-965+1637-1648; and amino acids 741-965+1637-1648 as set forth in SEQ ID NO 1.

21. A pharmaceutical composition according to the invention, wherein said FVIII molecule is conjugated with at least one half-life extending moiety. Preferably, said half-life extending moiety is a water soluble polymer. Preferably a PEG and/or a polysaccharide.

22. A pharmaceutical composition according to the invention, wherein at least one water soluble polymer is covalently attached to a glycan present in the B domain, preferably an O-glycan, preferably an O-glycan attached to the Ser750 amino acid residue as set forth in SEQ ID NO 1.

23. A pharmaceutical composition according to the invention, wherein said water soluble polymer is selected from the group consisting of: PEG, PSA, HES, HEP and HSA.

24. A pharmaceutical composition according to the invention, wherein said FVIII molecule is produced using an expression vector encoding a FVIII molecule comprising the FVIII B domain is as set forth in SEQ ID NO 2.

25. A pharmaceutical composition according to the invention, wherein the bioavailability of said FVIII molecule is at least 2, 3, 4, 5, 6, 7, 8, 9, or 10%. Preferably, the bioavailability is measured as the area under the curve of the plasma levels of FVIII after subcutaneous administration using either an antigen assay or a clotting assay.

26. A pharmaceutical composition according to the invention, wherein the ratio between FVIII and VWF is 1:50, 1:34, 1:25, 1:20:1:15, 1:10.1:7.5, preferably 0.5:1, 1:1, or 1:2.

27. A pharmaceutical formulation according to the invention, wherein the concentration of FVIII is at least about 100, 150, 200, 250, 300, 350, 400, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 20,000, 21,000, 22,000, 23,000, 24,000, 25,000, 26,000, 27,000, 28,000, 29,000, or 30,000 IU/ml.

28. A pharmaceutical formulation according to the invention, wherein the amount of FVIII bound to VWF fragment is at least 20, 25, 30, 35, 40, 45, 50, 55, 60, 65, 70, 75, 80, 85, 90, or 95% of the total amount of FVIII in said formulation.

29. Use of a compound according to the invention, or a pharmaceutical composition according to the invention, for treatment of haemophilia by extravascular, preferably subcutaneous, administration. The pharmaceutical composition according to the invention can also be administered by intradermal administration. The pharmaceutical composition according to the invention can furthermore be administered by intravenous administration.

30. A method of treatment of a haemophilia, wherein said method comprises subcutaneous administration of a therapeutically effective amount of a compound according to the present invention, or a pharmaceutical composition according to the present invention, to a patient in need thereof.

31. A method of increasing bioavailability of FVIII, wherein said method comprises a step of extravascular (e.g. subcutaneous/intradermal) co-administration of FVIII and a VWF fragment according to the invention, wherein the ratio of said FVIII and said VWF fragment is about 1:1-1:50, preferably 0.5:1, 1:1, 1:2, 1:10, 1:20 or 1:34.

32. A DNA molecule encoding a VWF fragment according to the invention.

33. An expression vector comprising a DNA molecule according to the invention.

34. A host cell comprising an expression vector according to the invention.

35. A method for making a VWF fragment according to the invention, wherein said method comprises incubation of a host cell in a suitable medium under suitable conditions and subsequently recovering said recombinant VWF fragment.

36. A pharmaceutical composition according to the invention, wherein said composition comprises one or more VWF fragments according to the invention.

37. A pharmaceutical composition comprising one or more VWF fragments according to the invention.
38. A method of treatment of von willebrand disease, wherein said method comprises extravascular (e.g. subcutaneous) administration of a therapeutically effective amount of a pharmaceutical composition according to the present invention, to a patient in need thereof.
39. A VWF fragment or VWF-like polypeptide comprising the 15 N terminal amino acids of the TIL' sequence 764-778, or more.
40. A VWF fragment according to the invention, wherein said VWF fragment interacts with/binds to residues C1858-Q1874, S2063-D2074 AND V2125-A2146 of the FVIII amino acid sequence as set forth in SEQ ID NO 1.
41. A VWF fragment according to the invention, wherein said fragment is conjugated with a half-life extending moiety.
42. A VWF fragment according to the invention, wherein said fragment is conjugated with a half-life extending moiety via a N- and/or O-linked glycan.
43. A VWF fragment according to the invention, wherein said VWF fragment reduced uptake of FVIII by antigen presenting cells in connection with binding of said VWF fragment to FVIII.
44. A pharmaceutical composition according to the invention, wherein the pharmaceutical composition is for intravenous administration.
45. A pharmaceutical composition according to the invention, which is a freeze-dried composition.
46. A pharmaceutical composition according to the invention, which is a liquid composition.
47. A pharmaceutical composition according to the invention, wherein the pharmaceutical composition is for intravenous administration and is a freeze-dried composition.
48. A pharmaceutical composition according to the invention, wherein the pharmaceutical composition is for intravenous administration and is a liquid composition.

It is understood that all aspects and embodiments of the invention can be combined and that they are not to be understood in any limiting way.

EXAMPLES

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Example 1

Subcutaneous Administration in FVIII Knockout Mice (1):
Two test compounds were prepared:
a) GlycoPEGylated FVIII, i.e. "N8-GP" (prepared essentially as disclosed in example 1+2 in WO2009108806) 2000 U FVIII/ml determined by chromogenic activity equivalent to 1.2 µM based on protein content.
b) GlycoPEGylated FVIII i.e. N8-GP (2000 U FVIII/ml or 1.2 µM, co-formulated with 0.74 mg/ml VWF fragment TIL'/E'/D3/A1 (equivalent to 9.3 µM) Both test compounds were formulated in 18 mg/ml NaCl, 3 mg/ml saccharose, 1.5 mg/ml L-histidine, 0.1 mg/ml polysorbate 80, 0.25 mg/ml $CaCl_2$, pH 7.3

12 FVIII KO mice, exon 16 knock-out in a mixed background of C57Bl/6 and SV129, bred at Taconic M&B (B6.129S4-F8tm1Kaz/J) with an approximate weight of 22 g were dosed subcutaneously in the flank with 10000 IU/kg FVIII or FVIII/VWF, 6 mice with each test compound.

Blood was sampled at 1, 3, 7, 17, 24, 30, 48, 72 and 96 h post administration. The mice were anaesthetized by Isoflurane/$O_2$/$N_2O$ prior to blood sampling via the retroorbital plexus. Three samples were taken from each mouse. Blood (45 µl) was stabilised with 5 µl of sodium-citrate (0.13 M) and added 200 µl FVIII coatest SP buffer (50 mM TRIS-HCl, 1% BSA, Ciprofloxacin 10 mg/L, pH 7.3). After centrifugation at 4000 g for 5 minutes at room temperature, the supernatants were immediately frozen on dry ice before storage at −80° C. prior to analysis.

Samples were analysed with regards to FVIII activity in a chromogenic assay as described by Ovlisen K et al. J. Thromb. Haemost, 2008, 6: 969-975 and by FVIII antigen analysis using two FVIII light chain antibodies (4F45 and 4F11) in a FVIII LOCI assay (Luminescence oxygen channelling immunoassay).

Mean plasma concentration versus time data were analysed by non-compartmental analysis using WinNonlin Phoenix (Pharsight Corporation) estimating the given pharmacokinetic parameters. The bioavailability was estimated using a previous i.v. pharmacokinetic study of N8-GP in FVIII KO mice.

Figure 2:
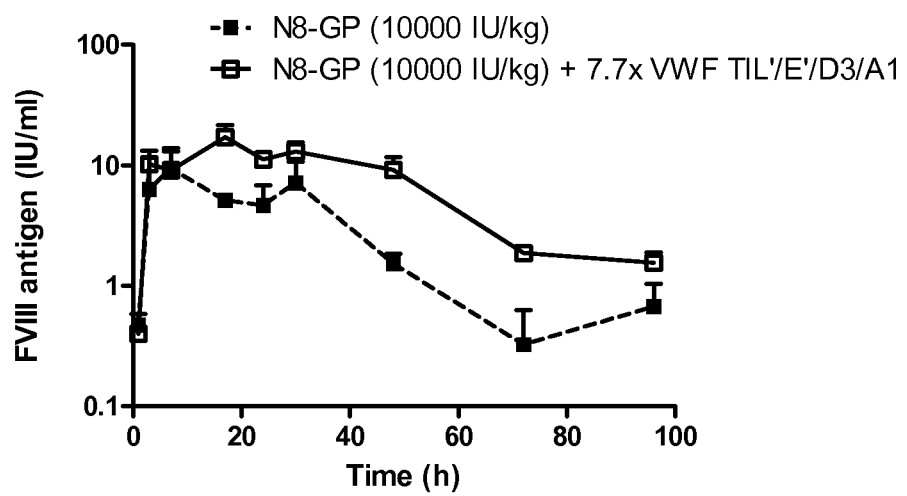
FIG. 2: FVIII antigen in plasma after subcutaneous administration of 10000 U/kg N8-GP with or without co-administration of 7.7 times the molar dose of VWF TIL'/E'/D3/A1 relatively to N8-GP. Data are mean and standard deviation of measurements from n=2 FVIII KO mice per time point

The circulating profiles of FVIII activity are shown graphically in FIG. 1, the circulating concentrations of FVIII antigen are shown in FIG. 2.

In this experiment, the bioavailability of GlycoPEGylated FVIII alone was calculated to be 27% based on activity and 19% based on antigen. The co-formulation with VWF increased the bioavailability to 40 and 47%, respectively.

Example 2

Subcutaneous Administration in FVIII Knockout Mice (2):
Two test compounds were prepared:
a) GlycoPEGylated FVIII (500 IU FVIII/ml determined by chromogenic activity equivalent to 0.3 µM)
b) GlycoPEGylated FVIII (500 IU FVIII/ml or 0.3 µM, co-formulated with 0.185 mg/ml VWF fragment TIL'/E'/D3/A1 (equivalent to 2.3 µM)
Based on a measured IC50 of 1.5 nM of the VWF fragment to FVIII and assuming that the measured IC50 equals $K_d$, 99% of the FVIII should be bound to VWF in this composition.
Both test compounds were formulated in 18 mg/ml NaCl, 3 mg/ml saccharose, 1.5 mg/ml L-histidine, 0.1 mg/ml polysorbate 80, 0.25 mg/ml $CaCl_2$, pH ~7.3

12 FVIII KO mice, exon 16 knock-out in a mixed background of C57Bl/6 and SV129, bred at Taconic M&B (B6.129S4-F8tm1Kaz/J) with an approximate weight of 22 g were dosed subcutaneously in the flank with 2500 IU/kg FVIII or FVIII/VWF, 6 mice with each test compound.

Blood was sampled at 1, 3, 7, 17, 24, 30, 48, 72 and 96 h post administration. The mice were anaesthetized by Isoflurane/$O_2$/$N_2O$ prior to blood sampling via the retroorbital plexus. Three samples were taken from each mouse. 45 µl of blood was stabilised with 5 µl of sodium-citrate (0.13 M) and added 200 µl FVIII coatest SP buffer (50 mM TRIS-HCl, 1% BSA, Ciprofloxacin 10 mg/L, pH 7.3). After centrifugation at 4000 g for 5 minutes at room temperature, the samples were immediately frozen on dry ice before storage at −80° C. prior to analysis.

Samples were analysed with regards to FVIII activity in a chromogenic assay as described by Ovlisen K et al. J. Thromb. Haemost, 2008, 6: 969-975 and by FVIII antigen analysis using two FVIII light chain antibodies (4F45 and 4F11) in a FVIII LOCI assay (Luminescence oxygen channeling immunoassay).

Mean plasma concentration versus time data were analysed by non-compartmental analysis using WinNonlin Phonix (Pharsight Corporaton) estimating the given pharmacokinetic parameters. The bioavailability was estimated using a previous i.v. pharmacokinetic study of N8-GP in FVIII KO mice.

Figure 3:
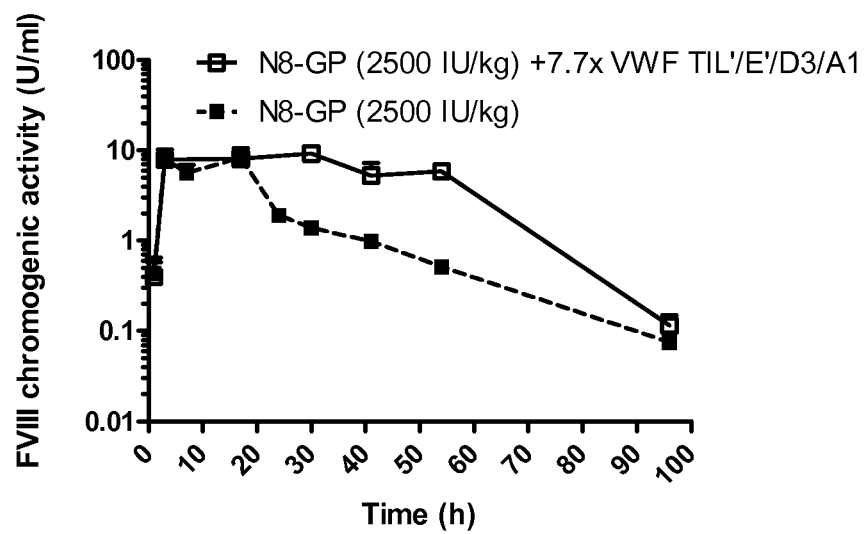
FIG. 3: FVIII activity in plasma after subcutaneous administration of 2500 U/kg N8-GP with or without co-administration of 7.7 times the molar dose of VWF TIL'/E'/D3/A1 relatively to N8-GP. Data are mean and standard deviation of measurements from n=2 FVIII KO mice per time point
Figure 4:
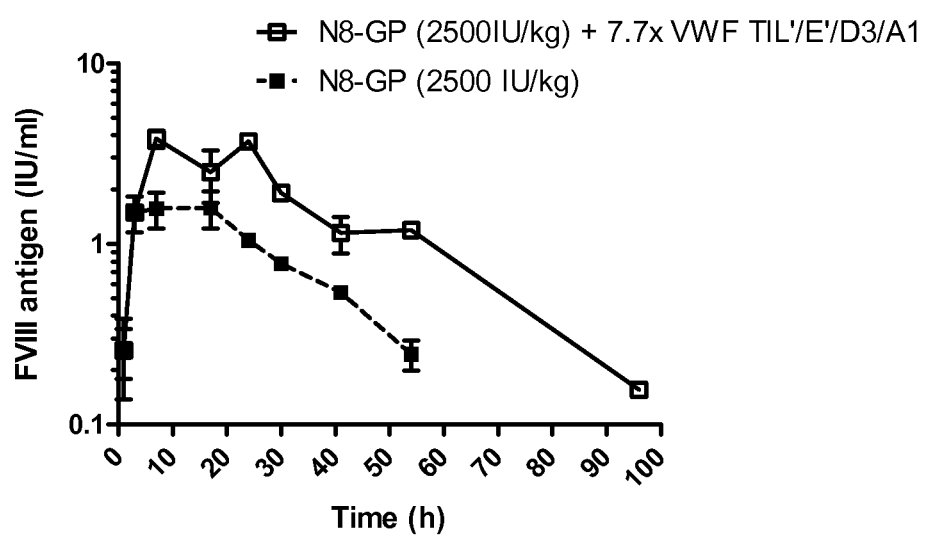
FIG. 4: FVIII antigen in plasma after subcutaneous administration of 2500 U/kg N8-GP with or without co-administration of 7.7 times the molar dose of VWF TIL'/E'/D3/A1 relatively to N8-GP. Data are mean and standard deviation of measurements from n=2 FVIII KO mice per time point.

The circulating profiles of FVIII activity are shown graphically in FIG. 3, the circulating concentrations of FVIII antigen are shown in FIG. 4.

In this experiment, the bioavailability of GlycoPEGylated FVIII alone was calculated to be 29% based on activity and 14% based on antigen. The co-formulation with VWF increased the bioavailability to 36% (antigen measurement).

Example 3

Figure 10:
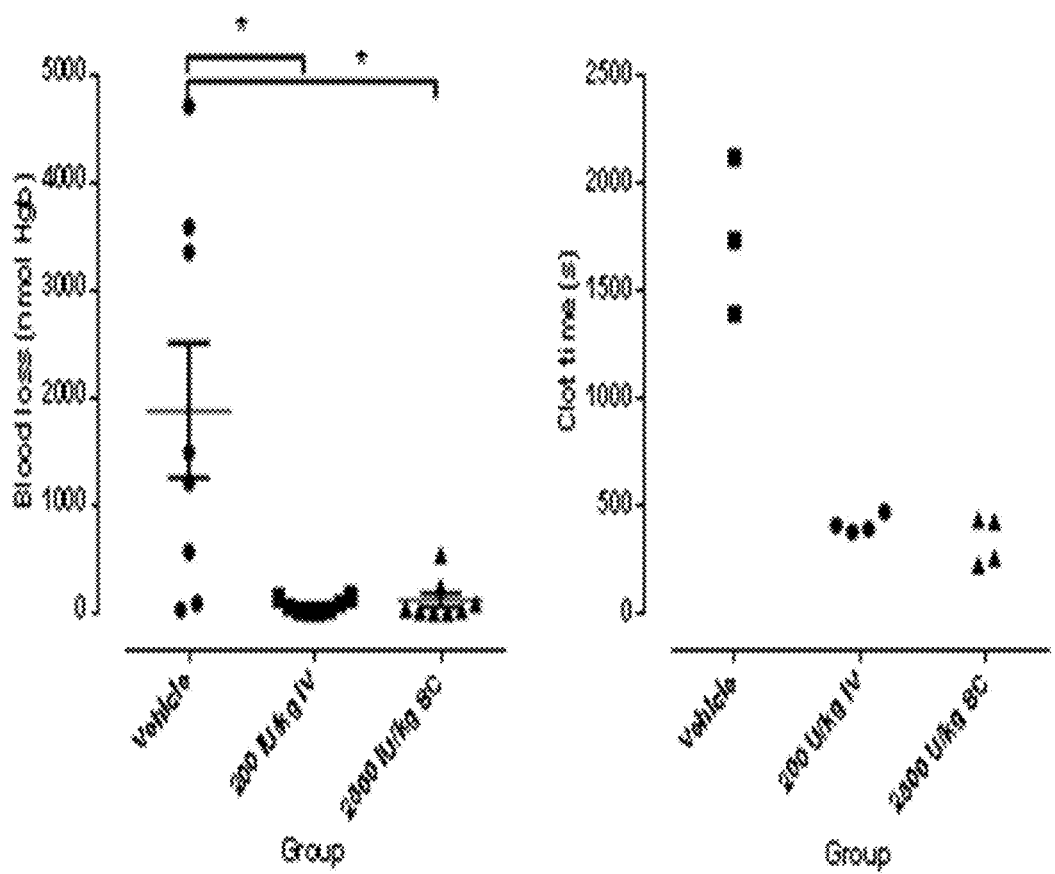
FIG. 10: s.c. administrated N8-GP is haemostatic effective in vivo. The left panel shows blood loss in FVIIIKO mice treated s.c. with N8-GP or vehicle 24 hr before tail transection, or i.v. 5 min before tail transection. N8-GP'' is a glyco-PEGylated FVIII molecule produced as described in Examples 1+2 in WO2009108806. The right panel shows clot times in whole blood from the mice ex vivo using ROTEM.
Figure 11:
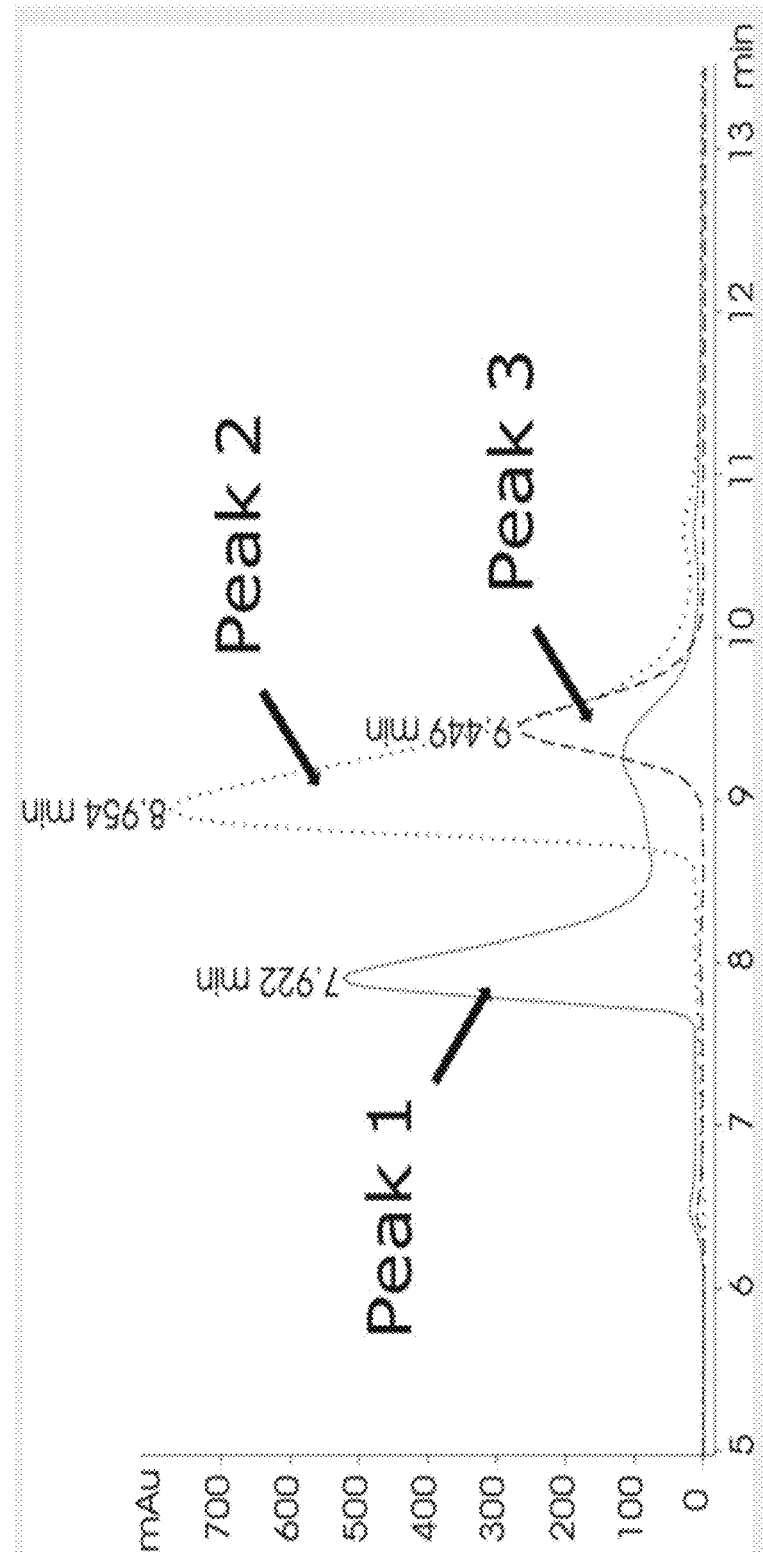
FIG. 11: SEC-UV (280 nm) chromatograms for FVIII, TIL'/E'/D3/A1 III, and a mixture of FVIII and TIL'/E'/D3/A1 III in 155 mM NaCl, 10 mM Calciumacetat, 10% Isopropanol at 25° C.
Figure 12:
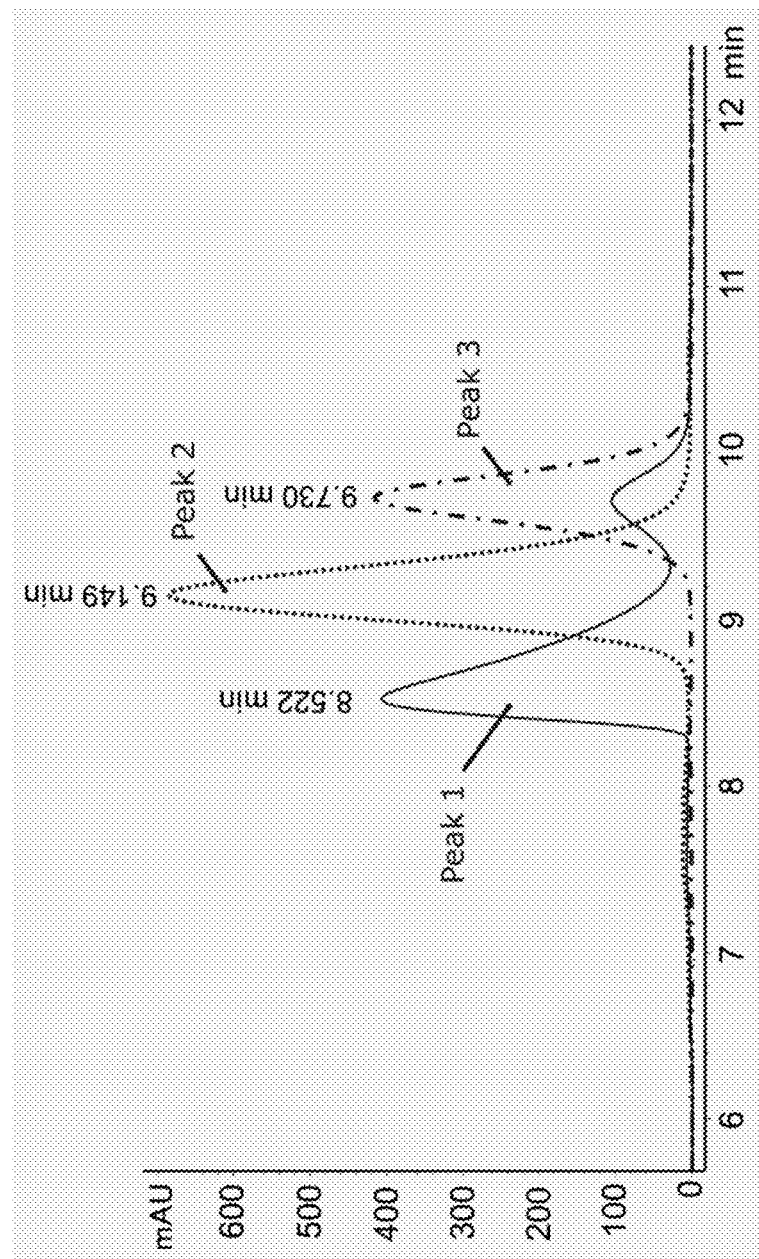
FIG. 12:. SEC-UV (280 nm) chromatograms for FVIII, TIL'/E'/D3 II, and a mixture of FVIII and TIL'/E'/D3 II in 155 mM NaCl, 10 mM Calciumacetat, 10% Isopropanol at 25° C.

Haemostatic Efficacy of s.c. Administered Co-Formulations of FVIII Compounds with VWF Compounds:

Study Outline:
Animals: FVIII k/o mice, 8-18 weeks old, male and females
Tail bleeding: n=6-12 per timepoint/group
Thrombo-elastography: n=2-4 per timepoint/group
Administration route: s.c. in the neck or flank (i.v. in the tail vein for control groups)
Dose volumes 1-10 ml/kg
Groups:
Vehicle controls dosed 24 hr prior to injury
i.v. controls dosed 5 min prior to injury
FVIII compounds co-formulated with VWF compounds dosed s.c. 5 min, 1, 3, 5, 12, 24, 48, 72, 96, 120, 144 or 168 hr prior to injury.
Procedures:
Compounds of interest are prepared in buffer (10 mM L-Histidine, 8.8 mM Sucrose, 0.01% Polysorbate 80, 308 mM NaCl, 1.7 mM CaCl2 (dihydrate), 0.37 mM L-Methionine, pH 6.9) to a concentration between 40 and 10000 U/ml and stored at −80 C until use.
Before tail transection, the mice are anaesthetised with isoflurane and placed on a heating pad
The tails are placed in pre-heated saline at 37° C. for 10 min
I.v. controls are injected 5 min, 24 or 48 hr prior to injury
The tail is transected 4 mm from the tip
Immediately before tail cut a 20 µl blood sample is drawn from the peri-orbital plexus for FVIII determination
Blood is collected over 30 min and the haemoglobin concentration determined by spectrophotometry at 550 nm
Parallel animals are used for blood sampling and subsequent analysis of their clotting parameters (ex vivo efficacy).
Results:
The prophylactic effect of the co-formulation is determined from comparing the blood loss during the 30 min study period at a certain time after s.c. administration (5 min until 168 hr) to that of 1, a vehicle control and 2, an i.v. control group with FVIII or glycoPEGylated FVIII. FIG. 10 shows that glycoPEGylated FVIII are haemostatic effective 24 hr after s.c. administration of 2500 U/kg as shown by reduction of blood loss and shortening of clot time ex vivo. Similar effect is seen for FVIII co-formulated with a VWF fragment.

Example 4

Evaluation of Bioavailability of FVIII:
Bioavailability of co-compositions of FVIII and VWF/VWF fragments according to the invention can be determined from evaluations of the effect on bioavailability in PK experiments as those described in examples 1 and 2 as well as evaluations of the prophylactic effect as described in example 3.

The bioavailability of a FVIII compound co-formulated with a concentration of VWF fragment that enables the majority of FVIII to be bound to a VWF fragment compound in the injection composition can be determined from the concentration of FVIII compound in the composition and from experiments evaluating the binding affinity of the VWF fragment compound to the FVIII compound such as e.g. surface plasmon resonance experiments.

Example 5

Titration of Dosis of FVIII: VWF Co-Composition:
Dose titration can be carried out as disclosed in examples 1-3. Briefly, plasma concentration of FVIII will be evaluated after s.c. administration of doses of 70, 100, 150, 280, 500, 1000 and 2500 IU/kg (FVIII units) alone or together with a VWF fragment in FVIII k/o mice.

Example 6

Titration of Ratio Between FVIII Compound and VWF Compound:
Titration of ratios between FVIII and VWF can be carried out as disclosed in experiments similar to that in examples 1 and 2 as well as that described in example 3.
For PK evaluation, doses of 280, 500, 1000 or 2500 IU/kg FVIII compound will be co-formulated with VWF fragments at a molar ratio of 1:1, 1:1.5, 1:2, 1:3, 1:4, 1:5, 1:7.7 or up to 1:100 (FVIII to VWF fragment) and plasma concentration of FVIII evaluated in FVIII k/o mice after s.c. administration. The maximum molar surplus of VWF fragment to FVIII will be determined from binding affinities of the fragment to the FVIII compound in question; the highest molar surplus used will be the one that should result in at least 99% of the FVIII used bound to a VWF fragment.
For prophylactic effect, the candidate compositions from the PK experiments will be evaluated in efficacy models, such as the tail bleeding described in example 3.

Example 7

Effect of VWF on Immunogenicity of FVIII
The immuno-modulatory effect of VWF co-formulated with a FVIII compound is evaluated in comparison to wild type FVIII and FVIII compounds alone.
In vivo, the relative immunogenicity is evaluated from the titer of FVIII binding antibodies and the determination of the level of neutralizing antibodies (inhibitors) at certain time points after administration. The assay for detection of FVIII binding antibodies is a radioimmunoassay (RIA). Briefly, anti-FVIII antibodies from a sample bind to radioactive $^{125}$I-labelled rFVIII. Immunoglobulin and immune complexes bind to protein G-sepharose and is precipitated by centrifugation. The radioactivity in the precipitate is measured and this is proportional to the amount of anti-FVIII antibodies in the sample. The result is expressed in percent of the total amount of added radioactivity. i.e. as % bound/total (% B/T).
Samples positive for anti-FVIII antibodies are analysed for the presence of FVIII neutralizing antibodies using a chromogenic assay. Briefly, samples are incubated with 1 IU/ml FVIII for 1 hr. The remaining FVIII activity is determined by addition of FIX, FX, thrombin, $CaCl_2$ and phospholipids. After incubation the amount of generated FXa is determined by addition of the chromogenic substrate S-2760 and the change in optical density (OD) is measured. The OD change is proportional to FVIII activity in the samples, and is compared to samples containing a known amount of FVIII and no inhibitors. The % remaining activity of the test sample is calculated compared to the reference samples without inhibitors/anti-FVIII antibodies added. Furthermore, the presence of anti-VWF antibodies is measured by ELISA using monoclonal or polyclonal anti-human VWF antibodies which does not cross react with murine VWF. If a strong anti-VWF response is detected, this can be expected to interfere with the binding of VWF to FVIII and the in vivo analysis is repeated using murine VWF fragments.

The appearance of anti-drug antibodies is evaluated after repeated (e.g. once weekly for 4 weeks or once daily for three weeks) s.c. administration of the compounds in naïve mice, in FVIII k/o mice as well as in mice tolerized to human FVIII. The readout is the ratio of animals with positive titres at certain time points after the first and/or the last administration (e.g. 1, 2, 3, 4, 5, 6, 7 or 8 weeks). FVIII k/o mice are injected weekly e.g. with 1000 IU/kg FVIII alone or in combination with VWF in a molar ratio ensuring that at least e.g. 87% of FVIII is bound to VWF. For daily administration, the FVIII dose is lower and based upon the bioavailability of the FVIII-VWF complex. Mice tolerized to hFVIII are injected weekly for e.g. eight weeks s.c. with e.g. 1000 IU/kg FVIII with or without VWF and in some experiments including additional challenge with complete Freund's adjuvant (CFA) for the first injection followed by weekly challenges by incomplete Freund's adjuvant (IFA).

Relative immunogenicity of VWF versus VWF fragments and of wild type FVIII versus a FVIII compound co-formulated with VWF is furthermore evaluated in vitro in a human CD4+ T-cell assay. This is done using peripheral blood mononuclear cells (PBMCs) depleted of CD8+ T-cells. FVIII is added to the cell culture e.g. for eight days. T-cell proliferation is evaluated during the course of the assay by pulsing for e.g. 18 h with $^3$H-thymidine in sub-samples from the cultures and subsequently measuring $^3$H-thymidine incorporation. Interleukin 2 production is measured at the end of the assay using an ELISPOT IL-2 kit e.g. from R&D Systems, following the manufacturer's instructions. The data obtained in the assays are converted to a "stimulation index" describing the ratio between compound-stimulated versus un-stimulated cells.

The HLA-binding capacity of VWF has been evaluated using in silico analysis of HLA-binding properties. Strong binding to a sequence in a modified VWF may indicate novel T-cell epitopes, although the in silico analysis tool is predicting epitopes that may not be processed by the naturally occurring proteases. In order to predict if the Cys->Ser mutation will induce a risk of induced immunogenicity in the VWF-mutants, the VWF protein sequences are applied to an in silico peptide/HLA-II binding prediction software. The peptide/HLA-II binding prediction software is based on two different algorithms, NetMHCIIpan 2.1 (NetMHCIIpan-2.0—Improved pan-specific HLA-DR predictions using a novel concurrent alignment and weight optimization training procedure. Nielsen M, Lundegaard C, Justesen S, Lund O, and Buus S. Immunome Res. 2010 Nov. 13; 6(1):9) performing pan-specific HLA-DR predictions—and NetMHCII 2.0 (NN-align—A neural network-based alignment algorithm for MHC class II peptide binding prediction. Nielsen M and Lund O. BMC Bioinformatics. 2009 Sep. 18; 10:296) performing HLA-DP/DQ predictions.

Twenty-three amino acid long peptides with the point of mutation in position 12 are used as input to the algorithms. The optimal processed peptide is assumed to be a 15'mer peptide with a nine amino acid core peptide binding to the HLA-II. The output is 15 amino acid long peptides with 9 amino acid long core peptides (in contact with HLA-II) and the predicted binding affinities in nanomolar.

The predicted binding affinities of the VWF mutant peptides are in the same range as the binding affinities of the wild type sequences (data not shown)—and because the peptides are predicted to bind with relatively poor affinity to the HLA-II molecules, the risk of inducing novel CD4+ T-cell epitopes is considered to be very low.

Of note, the in silico peptide/HLA-II binding predictions are based on experimental peptide/HLA-II binding data where it is very challenging to test cysteine-rich peptides (due to the nature of the peptides). Thus, cysteine-rich peptides are underrepresented in data sets used to train the different prediction algorithms. Therefore, the peptide/HLA-II binding predictions of these cysteine-rich VWF peptides are uncertain and should be analysed further using other immunogenicity prediction platforms (etc. in vitro peptide/HLA-II binding assays or ex vivo T-cell assays).

Example 8

Subcutaneous Administration in FVIII Knockout Mice (3): Two Test Compounds were Prepared:
a) B-domain truncated FVIII ("turoctocog alfa"/"N8"—produced essentially as disclosed in example 1 in WO2009108806) (4000 IU FVIII/ml determined by chromogenic activity assay and equivalent to 2.4 µM)
b) B-domain truncated FVIII (turoctocog alfa) (1000 IU FVIII/ml determined by chromogenic activity assay and equivalent to 0.6 µM) co-formulated with 0.37 mg/ml VWF fragment TIL'/E'/D3/A1 (equivalent to 4.6 µM)
Based on a measured binding affinity of 1.5 nM of the VWF fragment to FVIII, 99% of the FVIII should be bound to VWF in this composition.
Both test compounds were formulated in 18 mg/ml NaCl, 3 mg/ml saccharose, 1.5 mg/ml L-histidine, 0.1 mg/ml polysorbate 80, 0.25 mg/ml $CaCl_2$, pH ~7.3

12 FVIII KO mice, exon 16 knock-out in a mixed background of C57Bl/6 and SV129, bred at Taconic M&B (B6.129S4-F8tm1Kaz/J) with an approximate weight of 22 g were dosed subcutaneously in the flank with 10000 IU/kg FVIII or FVIII/VWF, 6 mice with each test compound.

Blood was sampled at 1, 3, 7, 17, 24, 30, 48, 72 and 96 h post administration. The mice were anaesthetized by Isoflurane/$O_2$/$N_2$O prior to blood sampling via the retroorbital plexus. Three samples were taken from each mouse. 45 µl of blood was stabilised with 5 µl of sodium-citrate (0.13 M) and added 200 µl FVIII coatest SP buffer (50 mM TRIS-HCl, 1% BSA, Ciprofloxacin 10 mg/L, pH 7.3). After centrifugation at 4000 g for 5 minutes at room temperature, the supernatants were immediately frozen on dry ice before storage at −80° C. prior to analysis.

Samples were analysed with regards to FVIII activity in a chromogenic assay as described by Ovlisen K et al. J. Thromb. Haemost, 2008, 6: 969-975 and by FVIII antigen analysis using two FVIII light chain antibodies (4F45 and 4F11) in a FVIII LOCI assay (Luminescence oxygen channelling immunoassay).

Mean plasma concentration versus time data were analysed by non-compartmental analysis using WinNonlin Phoenix (Pharsight Corporaton) estimating the given pharmacokinetic parameters. The bioavailability was estimated using a previous i.v. pharmacokinetic study of N8-GP in FVIII KO mice.

Figure 5:
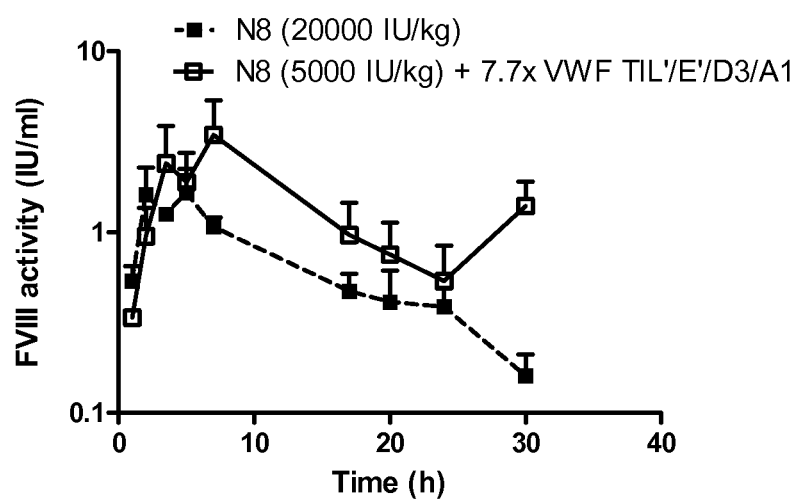
FIG. 5: FVIII activity in plasma after subcutaneous administration of 5000 or 20000 IU/kg wt FVIII (N8, turoctocog alfa) with or without co-administration of 7.7 times the molar dose of VWF TIL'/E'/D3/A1 relatively to FVIII, respectively. Data are mean and standard deviation of measurements from n=2 FVIII KO mice per time point. "N8"/"turocotog alfa" is a B domain truncated FVIII molecule produced as described in Example 1 in WO2009108806.
Figure 6:
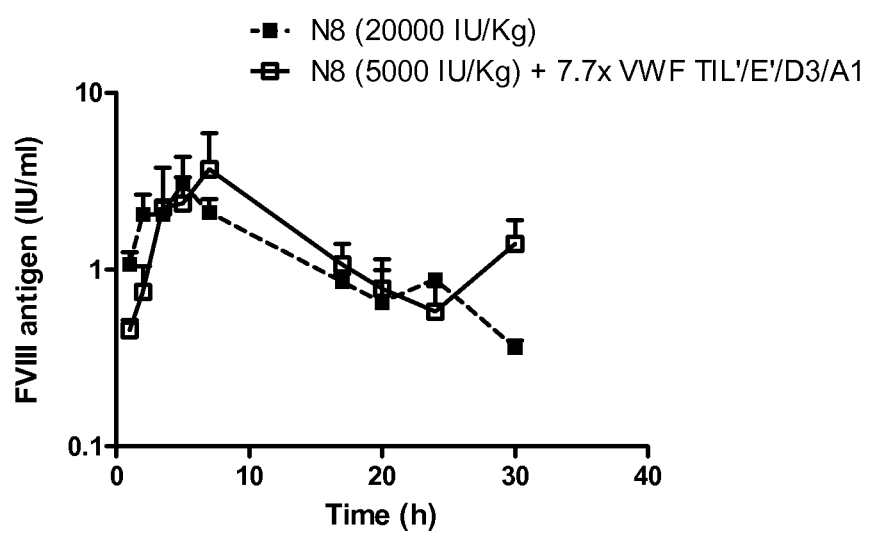
FIG. 6: FVIII antigen in plasma after subcutaneous administration of 5000 or 20000 IU/kg wt FVIII (N8, turoctocog alfa) with or without co-administration of 7.7 times the molar dose of VWF TIL'/E'/D3/A1 relatively to FVIII. Data are mean and standard deviation of measurements from n=2 FVIII KO mice per time point.

The circulating profiles of FVIII activity are shown graphically in FIG. 5 and antigen levels are shown in FIG. 6.

In this experiment, the bioavailability of B-domain truncated FVIII alone was calculated to be 0.9% based on activity. The co-formulation with the VWF fragment increased the bioavailability to 11%.

Example 9

Subcutaneous Administration in FVIII Knockout Mice (4):
Two Test Compounds were Prepared:
a) 226 amino acid B domain variant (1000 IU FVIII/ml determined by chromogenic activity assay and equivalent to 2.4 µM)
b) 226 amino acid B domain variant (1000 IU FVIII/ml determined by chromogenic activity assay and equivalent to 0.6 µM) co-formulated with 0.37 mg/ml VWF fragment TIL'/E'/D3/A1 (equivalent to 4.6 µM)
  Based on a measured binding affinity of 1.5 nM of the VWF fragment to FVIII, 99% of the FVIII should be bound to VWF in this composition.
  Both test compounds were formulated in 18 mg/ml NaCl, 3 mg/ml saccharose, 1.5 mg/ml L-histidine, 0.1 mg/ml polysorbate 80, 0.25 mg/ml $CaCl_2$, pH ~7.3

12 FVIII KO mice, exon 16 knock-out in a mixed background of C57Bl/6 and SV129, bred at Taconic M&B (B6.129S4-F8tm1Kaz/J) with an approximate weight of 22 g were dosed subcutaneously in the flank with 10000 IU/kg FVIII or FVIII/VWF, 6 mice with each test compound.

Blood was sampled at 1, 3, 7, 17, 24, 30, 48, 72 and 96 h post administration. The mice were anaesthetized by Isoflurane/$O_2$/$N_2$O prior to blood sampling via the retro-orbital plexus. Three samples were taken from each mouse. 45 µl of blood was stabilised with 5 µl of sodium-citrate (0.13 M) and added 200 µl FVIII coatest SP buffer (50 mM TRIS-HCl, 1% BSA, Ciprofloxacin 10 mg/L, pH 7.3). After centrifugation at 4000 g for 5 minutes at room temperature, the supernatants were immediately frozen on dry ice before storage at −80° C. prior to analysis.

Samples were analysed with regards to FVIII activity in a chromogenic assay as described by Ovlisen K et al. J. Thromb. Haemost, 2008, 6: 969-975 and by FVIII antigen analysis using two FVIII light chain antibodies (4F45 and 4F11) in a FVIII LOCI assay (Luminescence oxygen channelling immunoassay).

Mean plasma concentration versus time data were analysed by non-compartmental analysis using WinNonlin Phonix (Pharsight Corporaton) estimating the given pharmacokinetic parameters. The bioavailability was estimated using a previous i.v. pharmacokinetic study of N8-GP in FVIII KO mice.

In this experiment, the bioavailability of the 226 amino acid B domain FVIII variant alone was similar to that obtained with co-formulation with VWF. Hence, for this variant with a longer B-domain, VWF did not increase the bioavailability.

Example 10

Construction of Expression Vectors Encoding FVIII Molecules

Plasmid with insert encoding the F8-500 FVIII molecule (F8-500 equals turoctocog alfa/N8 encoding sequence) was used for production of FVIII. Starting at the N-terminus, the F8-500 vector encodes the FVIII heavy chain without the B domain (amino acids 1-740), a 21 amino acid linker (SFSQNSRHPSQNPPVLKRHQR—SEQ ID NO 2), and the FVIII light chain (amino acids 1649-2332 of full-length wild-type human FVIII). The sequence of the 21 amino acid linker is derived from the FVIII B domain and consists of amino acids 741-750 and 1638-1648 of full length wild-type human FVIII. Fragments of FVIII cDNA were amplified from full length FVIII cDNA and inserted into F8-500 coding plasmid giving rise to DNA constructs encoding the BDD FVIII.

Contructs encoding F8-500D-HIS-C2-linked-(GGGS)6-hFc(IgG1), F8-500D-HIS-C2-linked-(GGGS)6-mFc (IgG2A), and F8-500D-HIS-C2-linked-(GGGS)6-albumin were established as described in the following. The internal BamHI site (aa 604-606) in F8-500 coding DNA was eliminated by site-directed mutagenesis and DNA encoding the flexible $(GGGS)_6$ linker was inserted 3' to the coding region. A new BamHI site was introduced in the 3' end of the linker-coding DNA in order to ease cloning of C-terminal fusion partners between BamHI and NotI sites. Thus, a construct encoding F8-500-C2-linked-(GGGS)$_6$ was generated. DNA encoding human Fc (IgG1), mouse Fc (IgG2a), and human serum albumin was amplified.

The PCR products were inserted between the BamHI and Not I sites of the F8-500-C2-linked-(GGGS)6 coding vector giving rise to constructs encoding F8-500-C2-linked-(GGGS)6-hFc(IgG1), F8-500-C2-linked-(GGGS)6-mFc (IgG2A), and F8-500-C2-linked-(GGGS)6-albumin. A SphI/ClaI restriction fragment from the latter constructs were transferred to a F8-500D-His coding constructs in order to generate F8-500D-HIS-C2-linked-(GGGS)6-hFc(IgG1)-, F8-500D-HIS-C2-linked-(GGGS)6-mFc(IgG2A)-, and F8-500D-HIS-C2-linked-(GGGS)6-albumin coding constructs.

For transient expression as described in Example 11, DNA constructs consisting of the mammalian expression vector pTT5 with insert encoding BDD FVIII were utilized. For generation of stable cell lines producing BDD FVIII, the vector pTSV7 is utilized. This vector encodes dihydrofolate reductase allowing selection of transfected cells with the dihydrofolate reductase system. A SpeI/AgeI restriction fragment from a pTT5-derived vector encoding F8-500D-His was transferred to a pTSV7-derived vector encoding F8-500 leading to construct #1917 consisting of pTSV7 with insert encoding F8-500D-His.

Example 11

Transient Expression of FVIII

HKB11 cells at a density of 0.9-1.1×10$^6$ were transfected with a complex of plasmid (0.7 mg/l or 1.0 mg/l) and the transfection agent, 293Fectin (Invitrogen) (1.0 ml/l or 1.4 ml/l). The transfection complex was prepared by diluting the plasmid and the transfection separately, mixing the two solutions, and incubating the mixture at room temperature for 20 minutes. The complex mixture was added to the cell suspension and the suspension was incubated in shaker incubator for 4 or 5 days at 36.5° C. or 37° C. and at 5% or 8% $CO_2$. Cell culture harvests were analysed by chromogenic FVIII assay as described in Example 14 and/or filtered through a 0.22 µm membrane filter and utilized for purification of FVIII as described in Example 13.

Example 12

Stable Cell Line Expressing FVIII

Serum-free adapted CHO-DUKX-B11 cells were transfected with the expression plasmid construct #1917 described in Example 10 and encoding the FVIII F8-500D-His. Transfected cells were selected with the dihydrofolate reductase system and cloned by limiting dilution. Clones were screened for FVIII production by ELISA and chromogenic activity assay. The clone GedT019A was selected for upscaling. The cells were transferred to a bioreactor. The F8-500D-His protein was purified from cell culture harvests as described in Example 13

Example 13

Purification of FVIII

A column was packed with the resin VIIISelect (GE Healthcare), with the dimensions 1.6 cm in diameter and 4 cm in bed height giving 8 mL, and was equilibrated with 20 mM Imidazole+10 mM $CaCl_2$+0.01% Tween80+250 mM NaCl, pH7.3 at 500 cm/h. The culture filtrate prepared as described in Example 3 was applied to the column, and the column was subsequently washed with first equilibration buffer and then 20 mM Imidazole+10 mM $CaCl_2$+0.01% Tween80+1.5M NaCl, pH7.3. The bound FVIII was eluted isocratic at 90 cm/h with 20 mM Imidazole+10 mM $CaCl_2$+0.01% Tween80+1M Ammoniumacetate+6.5M Propylenglycol, pH7.3. The fractions containing FVIII were pooled and diluted 1:10 with 20 mM Imidazole+10 mM $CaCl_2$+0.01% Tween80, pH7.3 and applied to a column packed with F25-Sepharose (Thim et al., Haemophilia, 2009). The column dimension was 1.6 cm in diameter and 2 cm in bed height giving 4 mL in column volume. The column was equilibrated at 180 cm/h with 20 mM Imidazole+10 mM $CaCl_2$+0.01% Tween80+150 mM NaCl+1M Glycerol, pH7.3 prior to application. After application the column was washed first with equilibration buffer and then 20 mM Imidazole+10 mM $CaCl_2$+0.01% Tween80+ 650 mM NaCl, pH7.3. The bound FVIII was isocratic eluted with 20 mM Imidazole+10 mM $CaCl_2$ 0.01% Tween80+ 2.5M NaCl+50% (v/v) Ethylenglycol, pH7.3 at 30 cm/h. The fractions containing FVIII were pooled and diluted 1:15 with 20 mM Imidazole+10 mM $CaCl_2$+0.01% Tween80, pH7.3, except FVIII-variants with deletions of the a3 domain which were diluted 1:45 in the same buffer. The diluted pool was applied to a column packed with Poros 50HQ (PerSeptive Biosystem), with the column dimensions 0.5 cm in diameter and 5 cm in bed height giving 1 mL in column volume. The column was equilibrated at 300 cm/h with 20 mM Imidazole+ 10 mM $CaCl_2$+0.01% Tween80+50 mM NaCl+1M Glycerol, pH7.3 prior to application. The column was washed with equilibration buffer before the elution using a linear gradient over 5 column volumes from equilibration buffer to 20 mM Imidazole+10 mM $CaCl_2$+0.01% Tween80+1M NaCl+1M Glycerol, pH7.3. The fractions containing FVIII were pooled and the pool was stored at −80° until use.b The FVIII molecules with HIS-tag were purified essentially as described above, however the second purification step (F25-sepharose) was exchanged to Chelating Sepharose FF (GE Healtcare) charged with 2 column volumes of 1M $NiSO_4$. The column dimension was 0.5 cm in diameter and 5 cm bed height giving 1 mL column volume. The column was equilibrated with 30 mM Imidazole+10 mM $CaCl_2$+0.01% Tween80+1.5M NaCl, pH7.3 at 180 cm/h prior to application. After application the column was washed with 30 column volumes of equilibration buffer prior to elution using a linear gradient over 5 column volumes to 250 mM Imidazole+10 mM $CaCl_2$+0.01% Tween80+1.5M NaCl, pH7.3. The fractions containing FVIII were pooled and diluted 1:30 with 20 mM Imidazole+10 mM $CaCl_2$+0.01% Tween80, pH7.3. The final purification step (Poros 50HQ) was performed as described above.

Example 14

FVIII Activity in Cell Culture Harvests Measured by Chromogenic Assay

The FVIII activity (FVIII:C) of the rFVIII compound was evaluated in a chromogenic FVIII assay using Coatest SP reagents (Chromogenix) as follows: rFVIII samples and a FVIII standard (Coagulation reference, Technoclone) were diluted in Coatest assay buffer (50 mM Tris, 150 mM NaCl, 1% BSA, pH 7.3, with preservative). Fifty µl of samples, standards, and buffer negative control were added to 96-well microtiter plates (Spectraplates MB, Perkin Elmer). All samples were tested diluted 1:100, 1:400, 1:1600, and 1:6400. The factor IXa/factor X reagent, the phospholipid reagent and $CaCl_2$ from the Coatest SP kit were mixed 5:1:3 (vol:vol:vol) and 75 µl of this added to the wells. After 15 min incubation at room temperature, 50 µl of the factor Xa substrate 5-2765/thrombin inhibitor I-2581 mix was added and the reactions were incubated 5 min at room temperature before 25 µl 1 M citric acid, pH 3, was added. The absorbance at 405 nm was measured on an Envision microtiter plate reader (Perkin Elmer) with absorbance at 620 nm used as reference wavelength. The value for the negative control was subtracted from all samples and a calibration curve prepared by linear regression of the absorbance values plotted vs. FVIII concentration. The yields of the present FVIII relative to that of the F8-500 protein are shown in Table 1.

Example 15

FVIII Activity in Purified Samples Measured by Chromogenic Assay

The FVIII activity (FVIII:C) of the rFVIII compound was evaluated in a chromogenic FVIII assay using Coatest SP reagents (Chromogenix) as follows: rFVIII samples and a FVIII standard (e.g. purified wild-type rFVIII calibrated against the 7th international FVIII standard from NIBSC) were diluted in Coatest assay buffer (50 mM Tris, 150 mM NaCl, 1% BSA, pH 7.3, with preservative). Fifty µl of samples, standards, and buffer negative control were added to 96-well microtiter plates (Nunc) in duplicates. The factor IXa/factor X reagent, the phospholipid reagent and $CaCl_2$ from the Coatest SP kit were mixed 5:1:3 (vol:vol:vol) and 75 µl of this added to the wells. After 15 min incubation at room temperature 50 µl of the factor Xa substrate S-2765/thrombin inhibitor I-2581 mix was added and the reactions incubated 10 min at room temperature before 25 µl 1 M citric acid, pH 3, was added. The absorbance at 415 nm was measured on a Spectramax microtiter plate reader (Molecular Devices) with absorbance at 620 nm used as reference wavelength. The value for the negative control was subtracted from all samples and a calibration curve prepared by linear regression of the absorbance values plotted vs. FVIII concentration. The specific activity was calculated by dividing the activity of the samples with the protein concentration determined by HPLC. For HPLC, the concentration of the sample was determined by integrating the area under the peak in the chromatogram corresponding to the light chain and compare with the area of the same peak in a parallel analysis of a wild-type rFVIII, where the concentration was determined by amino acid analyses. The results are shown in Table 1.

Example 16

FVIII Activity in Purified Samples Measured by One-Stage Clot Assay

FVIII activity (FVIII:C) of the rFVIII compounds was further evaluated in a one-stage FVIII clot assay as follows: rFVIII samples and a FVIII standard (e.g. purified wild-type rFVIII calibrated against the 7th international FVIII standard from NIBSC) were diluted in HBS/BSA buffer (20 mM hepes, 150 mM NaCl, pH 7.4 with 1% BSA) to approximately 10 IU/ml followed by 10-fold dilution in FVIII-deficient plasma containing VWF (Dade Behring or Siemens). The samples were subsequently diluted in HBS/BSA buffer. The APTT clot time was measured on an ACL300R or an ACL9000 instrument (Instrumentation Laboratory) using the single factor program. FVIII-deficient plasma with VWF (Dade Behring or Siemens) was used as assay plasma and SynthASil, (HemosIL™, Instrumentation Laboratory) as aPTT reagent. In the clot instrument, the diluted sample or standard is mixed with FVIII-deficient plasma, aPTT reagents at 37° C. Calcium chloride is assed and time until clot formation is determined by turbidity. The FVIII activity in the sample is calculated based on a standard curve of the clot formation times of the dilutions of the FVIII standard. The results are shown in table 1.

TABLE 1

Yields and specific activities of different BDD FVIII molecules ("His-tagged" for easier purification).

| Compound | B domain amino acids | Yield by transient transfection (relative to F8-500) | Specific activity measured by chromogenic assay (IU/mg) | Specific activity measured by one-stage clot assay (IU/mg) |
|---|---|---|---|---|
| F8-500E-His | 741-857 + 1637-1648 | 0.7 | 10501 | 9122 |
| F8-500L-His | 741-914 + 1637-1648 | 0.6 | 10330 | 8282 |
| F8-500M-His | 741-954 + 1637-1648 | 0.6 | 12404 | 10259 |
| F8-500D-His | 741-965 + 1637-1648 | 0.3 | 9015 | 9579 |
| F8-500G-His | 741-965 + 1637-1648 Amino acid replacements: N757Q-N784Q-N828Q-N900Q-N943Q-N963Q | 0.7 | 11507 | 9822 |
| F8-500N-His | 741-1003 + 1637-1648 | 0.4 | — | — |
| F8-500H-His | 741-1020 + 1637-1648 | 0.7 | 10027 | 10541 |
| F8-500I-His | 741-1079 + 1637-1648 | 0.7 | — | — |
| F8-500J-His | 741-1206 + 1637-1648 | 0.6 | — | — |
| F8-500F-His | 741-1261 + 1637-1648 | 0.3 | 5691 | 4855 |
| F8-500K-His | 741-1309 + 1637-1648 | 0.4 | — | — |
| F8-500-His2-4N | 741-914 + 1637-1648 | 0.6 | — | — |
| F8-500-His2-5N | 741-954 + 1637-1648 | 0.7 | — | — |
| F8-500-His2-6N | 741-968 + 1637-1648 | 0.6 | 14088 | 12784 |
| F8-500-His2-7N | 741-1003 + 1637-1648 | 0.5 | 7211 | 7542 |
| F8-500-His2-8N | 741-1018 + 1637-1648 | 0.7 | 8664 | 7481 |
| F8-500-His2-10N | 741-1070 + 1637-1648 | 0.6 | 12391 | 8253 |
| F8-500-His2-11N | 741-1230 + 1637-1648 | 0.5 | — | — |
| F8-500-His2-15N | 741-1301 + 1637-1648 | 0.4 | — | — |
| F8-500D-His-D519V-E1984A | 741-965 + 1637-1648 | 0.5 | 15282 | 9729 |
| F8-500D-His-C2 linked-(GGGS)6-hFc(IgG1) | 741-965 + 1637-1648 | 0.6 | — | — |
| F8-500D-His-C2 linked-(GGGS)6-mFc(IgG2a) | 741-965 + 1637-1648 | 0.6 | 13509 | 8858 |
| F8-500D-His-C2 linked-(GGGS)6-albumin | 741-965 + 1637-1648 | 0.7 | 12226 | 5852 |

Example 17

Construction of Expression Vectors Encoding VWF Fragments

DNA fragments encoding the VWF signal peptide, followed by different C-terminally truncated versions, the VWF D' domain and the VWF D3 domain, an Ala-Leu-Ala spacer and a HPC4 tag were generated by polymerase chain reaction (PCR) using plasmid pLC095 as template (Plasmid pLLC095 is described in Example 26. The primer JP1000 was used as forward primer in all PCR reactions in combination with the reverse primers JP1001-JP1008 shown in Table 2.

TABLE 2

| Forward primer | Forward primer Sequence (5'-3') |
|---|---|
| JP1000 VWF-HindIII S | CTAAGCGTAAGCTTGCCACCATGATTCCTGCCAGATTTGCCGG (SEQ ID NO 23) |

TABLE 2-continued

| Reverse primer | Reverse primer Sequence (5'-3') |
|---|---|
| JP1001 VWF 764-828 | TGGTCCTCAGCTAGCGCGGGACACCTTTCCAGGGCCACAC (SEQ ID NO 24) |
| JP1002 VWF 764-865 | TGGTCCTCAGCTAGCGCGGCATCACACACATGGTCTGTGC (SEQ ID NO 25) |
| JP1003 VWF 764-1035 | TGGTCCTCAGCTAGCGCTCTGGTGTCAGCACACTGCGAGCTC (SEQ ID NO 26) |
| JP1004 VWF 764-1041 | TGGTCCTCAGCTAGCGCTGAGTCCAGAGGCACTTTTCTGG (SEQ ID NO 27) |
| JP1005 VWF 764-1045 | TGGTCCTCAGCTAGCGCGGTGGCAGGGGATGAGTCCAGAG (SEQ ID NO 28) |
| JP1006 VWF 764-1250 | TGGTCCTCAGCTAGCGCGGCATCTGTGGGAGGCACCACC (SEQ ID NO 29) |
| JP1007 VWF 764-1261 | TGGTCCTCAGCTAGCGCGTCCTCCACATACAGAGTGGTG (SEQ ID NO 30) |
| JP1008 VWF 764-1268 | TGGTCCTCAGCTAGCGCATCGTGCAACGGCGGTTCCGAG (SEQ ID NO 31) |

The PCR products were digested with HindIII and NheI and were subsequently cloned into a HindIII and NheI digested pJSV164 vector using Rapid DNA Ligation kit (Roche Diagnostics GmbH, Mannheim, Germany). pJSV164 is a pTT5 based expression vector (Yves Durocher, CNRC, Montreal, Canada) containing a CD33 signal peptide and a HPC4 tag. Digestion of pJSV164 with HindIII and NheI removes the CD33 signal peptide and allows cloning of the gene of interest in frame with the HPC4 tag to generate an expression cassette encoding a C-terminally HPC4 tagged gene of interest in which the gene of interest and the HPC4 tag is separated by an Ala-Leu-Ala linker peptide. The ligation reactions were transformed into Top10 cells (Life Technologies, Carlsbad, Calif., USA).

The resulting eight plasmids were named as shown in Table 3. The amino acid sequences of the generated proteins are outlined in SEQ ID NO 4, 5, 6, 7, 8, 11 and 16.

TABLE 3

| Vector name | Insert |
|---|---|
| pJSV343 | VWF 764-828-HPC4 (SEQ ID NO 4) |
| pJSV344 | VWF 764-865-HPC4 (SEQ ID NO 5) |
| pJSV345 | VWF 764-1035-HPC4 (SEQ ID NO 6) |
| pJSV346 | VWF 764-1041-HPC4 (SEQ ID NO 7) |
| pJSV347 | VWF 764-1045-HPC4 (SEQ ID NO 8) |
| pJSV348 | VWF 764-1250-C1099/1142S-HPC4 (SEQ ID NO 11) |
| pJSV349 | VWF 764-1261-C1099/1142S-HPC4 (SEQ ID NO 14) |
| pJSV350 | VWF 764-1268-C1099/1142S-HPC4 (SEQ ID NO 15) |

Example 18

Construction of Expression Vectors Encoding VWF Fragments (2)

Three additional HPC4 tagged, truncated variants of VWF were generated by Ligation independent cloning (LIC) using pJSV348 (see Example 17) as template. Three independent PCR reactions were set-up on pJSV438 using the primers shown in Table 4.

TABLE 4

| Fragment | Primer name | Primer sequence (5'-3') |
|---|---|---|
| VWF(864-1250)-HPC4 (SEQ ID NO 12) | VWF(864-1250)-HPC4 S | GGGACCCTTTGTGATGCCACGTGCTCCACGATCG (SEQ ID NO 32) |
| | VWF(864-1250)-HPC4 AS | GCACGTGGCATCACAAAGGGTCCCTGGCAAAATGAG (SEQ ID NO 33) |
| VWF(764-1128)-HPC4 (SEQ ID NO 9) | VWF(764-1128)-HPC4 S | TTGTGCCCCAGGAGGACCAAGTAGATCCGCGGCTC (SEQ ID NO 34) |
| | VWF(764-1129)-HPC4 AS | TACTTGGTCCTCCTGGGGGCACAATGTGGCCGTC (SEQ ID NO 35) |

TABLE 4-continued

| Fragment | Primer name | Primer sequence (5'-3') |
|---|---|---|
| VWF(764-1198)-HPC4 (SEQ ID NO 10) | VWF(764-1198)-HPC4 S | GACTGTCCAGTGGAGGACCAAGTAGATCCGCGG (SEQ ID NO 36) |
| | VWF(764-1198)-HPC4 AS | TTGGTCCTCCACTGGACAGTCTTCAGGGTCAA (SEQ ID NO 37) |

The three PCR fragments VWF(864-1250)-HPC4, VWF(764-1128)-HPC4 and VWF(764-1198)-HPC4 were 5685/5610/5817 by in size respectively. The PCR fragments were DpnI treated to remove methylated template DNA. The PCR fragments were subsequently purified from gel and were self-ligated by LIC using the In-Fusion HD Cloning Kit (Clontech, Mountain View, Calif., USA) to generate circular DNA fragments and subsequently transformed into Top10 cells (Life Technologies, Carlsbad, Calif., USA).

The resulting three plasmids were named as shown in Table 5. The amino acid sequences of the generated proteins are outlined in SEQ ID NOs 12, 9, and 10.

TABLE 5

| Vector name | Insert |
|---|---|
| pJSV405 | VWF(864-1250)-C1099/1142S-HPC4 monomer (SEQ ID NO 12) |
| pJSV406 | VWF(764-1128)-C1099S-HPC4 monomer (SEQ ID NO 9) |
| pJSV407 | VWF(764-1198)-C1099/1142S-HPC4 monomer (SEQ ID NO 10) |

Example 19

Transient Expression of VWF Fragments

Human embryonic kidney 293 6E suspension cells at a density of $0.9-1.1 \times 10^6$ cells/ml were transfected with a complex of VWF fragment coding plasmid (0.7 mg/l or 1.0 mg/l) and the transfection agent 293Fectin (Invitrogen) (1.0 ml/l or 1.4 ml/l). The transfection complex was prepared by diluting the plasmid and the transfection separately, mixing the two solutions, and incubating the mixture at room temperature for 20 minutes. The complex mixture was added to the cell suspension and the suspension was incubated in shaker incubator for 5 days at 36.5° C. or 37° C. and at 5% or 8% $CO_2$. Cell culture harvests were filtered through a 0.22 µm membrane filter and utilized for purification of VWF fragment as described in Example 22.

Example 20

Preparation of Dimer Forms of VWF Fragments

In the native full length VWF molecule (SEQ ID NO 22) two cysteine residues in the N-terminal part of the molecule are supposed to participate in the dimerization and/or multimerization of VWF: Cys1099 and Cys1142.

In all of the monomeric fragments of the sequences (SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, and SEQ ID NO 21) two cysteine residues (Cys1099 and Cys1142) are mutated to other amino acid residues so that the expressed molecule is not able to form dimers/multimers. A monomeric fragment of SEQ ID NO 9 is generated by mutating Cys 1099 to another amino acid residue.

In some cases, a dimeric form of the VWF fragments is wanted. This can be accomplished in several ways:

One method to accomplish dimer formation is to keep the two residues at position 1099 and position 1142 as cysteines. In order to make a recombinant dimeric molecule, the cDNA encoding the desired VWF fragment is including the presequence of VWF e.g the D1D2 sequence of VWF (amino acid residues 23-763 of SEQ ID NO 22). This will, during processing in the golgi apparatus align two monomers of a given VWF fragment in a configuration allowing a dimeric molecule to be formed with two disulphide bonds in which Cys1099 in monomer 1 is connected to a Cys1099 in monomer 2 and Cys1142 in monomer 1 is connected to Cys1142 in monomer 2.

Another method to accomplish dimer formation is to avoid the inclusion of the presequence (amino acid residues 23-763 of SEQ ID NO 22) and simply let a recombinant VWF fragment with Cys in position 1099 and 1142 form a dimeric molecule. This can in principle result in a series of different dimers e.g.:

Cys1099-Cys1099/Cys1142-Cys1142 (two disulphide bonds—like above)
Cys1099-Cys1142/Cys1099-Cys1142 (two disulphide bonds)
Cys1099-Cys1099 (one disulphide bond)
Cys1142-Cys1142 (one disulphide bond)
Cys1099-Cys1142 (one disulphide bond)

Yet another method to accomplish dimer formation may be toto replace one of the cysteine residues 1099 or 1142 with other amino acid residues (e.g. Serine, Arginine).

If Cys1099 is replaced with a non-Cysteine residue, the molecule may form a dimer by establishment of a disulphide bond between Cys1142 in monomer 1 with Cys1142 in monomer 2.

If Cys1142 is replaced with a non-Cysteine residue, the molecule may form a dimer by establishment of a disulphide bond between Cys1099 in monomer 1 with Cys1099 in monomer 2.

The dimeric forms mentioned above may be constructed either with or without the D1D2 presequence of VWF (amino acid residues 23-763 of SEQ ID NO 22).

The different monomeric and dimeric forms will have different properties with regards to their binding to FVIII, their ease of production and their effect on bioavailability of FVIII when injected subcutaneously as a co-formulation.

Example 21

Evaluation of Binding of VWF and VWF Fragments to FVIII Using a Competition ELISA In order to investigate the binding of the different VWF fragments to FVIII the following method is used. Briefly, human VWF is coated in a microtiterplate and incubated overnight at 4° C. After blocking, a solution with pre-incubated FVIII (1 nM) and VWF/VWF-fragment is added to the plate, followed by detection with biotinylated anti FVIII antibody and streptavidin-peroxidase S-POD (1:20000). The absorbance is measured at 450/620 nm. The IC50 values are shown in Table 6.

acetic acid, 100 mM NaCl, pH=4.0. The pool from the anti-VWF column is adjusted to pH=7.5 and applied onto a Mono Q column. Prior to the application the Mono Q column is equilibrated with 20 mM HEPES, 100 mM NaCl, pH=7.5.

TABLE 6

| Compound number | Domain/comment | VWF fragment sequence | Derived from SEQ ID NO | IC50 (Ki) |
|---|---|---|---|---|
| 2304 | TIL'E' | VWF(764-865)-ALA-HPC4 monomer | 5 | 2.0 μM |
| 2306 | TIL'/E'/VWD3 II | VWF(764-1041)-ALA-HPC4 monomer | 7 | 2.2 μM |
| 2307 | TIL'/E'/VWD3 III | VWF(764-1045)-ALA-HPC4 monomer | 8 | 2.0 μM |
| 2308 | TIL'/E'/D3 I | VWF(764-1250)-C1099/1142S-ALA-HPC4 monomer | 11 | 12 nM |
| 2309 | TIL'/E'/D3 II | VWF(764-1261)-C1099/1142S-ALA-HPC4 monomer | 14 | 10 mM |
| 2310 | TIL'/E'/D3 III | VWF(764-1268)-C1099/1142S-ALA-HPC4 monomer | 16 | 15 nM |
| 0170 | TIL'/E'/D3/A1 III | VWF(764-1464)-C1099/1142S-HPC4 monomer | 19 | 12 nM |
| 0194 | TIL'/E'/D3/A1 III | VWF(764-1464)-C1099S-HPC4 monomer | 19 | 8.0 nM |
| 0240 | TIL'/E'/D3/A1 IIIdimer | VWF(764-1464)-HPC4 dimer | 19 | 0.7 nM |
| 0001 | D3 I | VWF(864-1250)-C1099/1142S-ALA-HPC4 monomer | 12 | 20 μM |
| 0003 | TIL'/E'/VWD3/C8-3/TIL-3 | VWF(764-1198)-C1099/1142S-ALA-HPC4 monomer | 10 | 28 nM |
| 0314 | Plasma derived full length VWF | VWF (764-2813) | 22 | 1.1 nM |

These differences in FVIII binding between different fragments could indicate different effects in a subcutaneously administered FVIII co-formulation. The IC50 values are also being used to determine the optimal VWF and FVIII concentrations in the co-formulation mixtures.

Example 22

Purification and Characterisation of HPC4-Tagged VWF Fragments

Some VWF fragments are cloned and expressed with a C-terminal HPC4 tag: EDQVDPRLIDGK (SEQ ID NO 38). Sometimes an additional linker with the sequence of ALA is introduced between the VWF fragment and the HPC4 tag. After cloning, expression and cell culturing the cell media is added $CaCl_2$ to a final concentration of 1 mM. The media is passed over an anti-HPC4 column. The column is equilibrated with 20 mM HEPES, 100 mM NaCl, 1 mM $CaCl_2$, pH=7.5. After application of the cell media, the column is washed with 20 mM HEPES, 1M NaCl, 1 mM $CaCl_2$, pH=7.5 and the HPC4-tagged VWF fragment is subsequently eluted with 20 mM HEPES, 100 mM NaCl, 5 mM EDTA, pH=7.5. The pool from the anti-HPC4 column is added 3 volumes of water to reduce the conductivity and applied onto a Mono Q column. Prior to the application the Mono Q column is equilibrated with 20 mM HEPES, 100 mM NaCl, 5 mM EDTA, pH=7.5. The Mono Q column is washed with 20 mM HEPES, 100 mM NaCl, pH=7.5 and the VWF fragment is eluted with a gradient from 100 mM NaCl to 2M NaCl in 20 mM HEPES, 10 mM $CaCl_2$, pH=7.5.

The purified protein is characterised by 1) SDS-gel electrophoreses, 2) analytical HPLC and 3) amino acid sequence analysis.

Purification and Characterisation of Non-Tagged VWF Fragments.

After cloning, expression and cell culturing the cell media is passed over an anti-VWF column. The anti-VWF antibody recognise amino acid residue number 764-865 of VWF (SEQ ID NO 5).The column is equilibrated with 20 mM HEPES, 100 mM NaCl, pH=7.5. After application of the cell media, the column is washed with 20 mM HEPES, 1M NaCl, pH=7.5 and the VWF fragment is subsequently eluted with 50 mM The Mono Q column is washed with 20 mM HEPES, 100 mM NaCl, pH=7.5 and the VWF fragment is eluted with a gradient from 100 mM NaCl to 2M NaCl in 20 mM HEPES, pH=7.5.

The purified VWF fragment is characterised by 1) SDS-gel electrophoreses, 2) analytical HPLC and 3) amino acid sequence analysis.

Example 23

Figure 9:
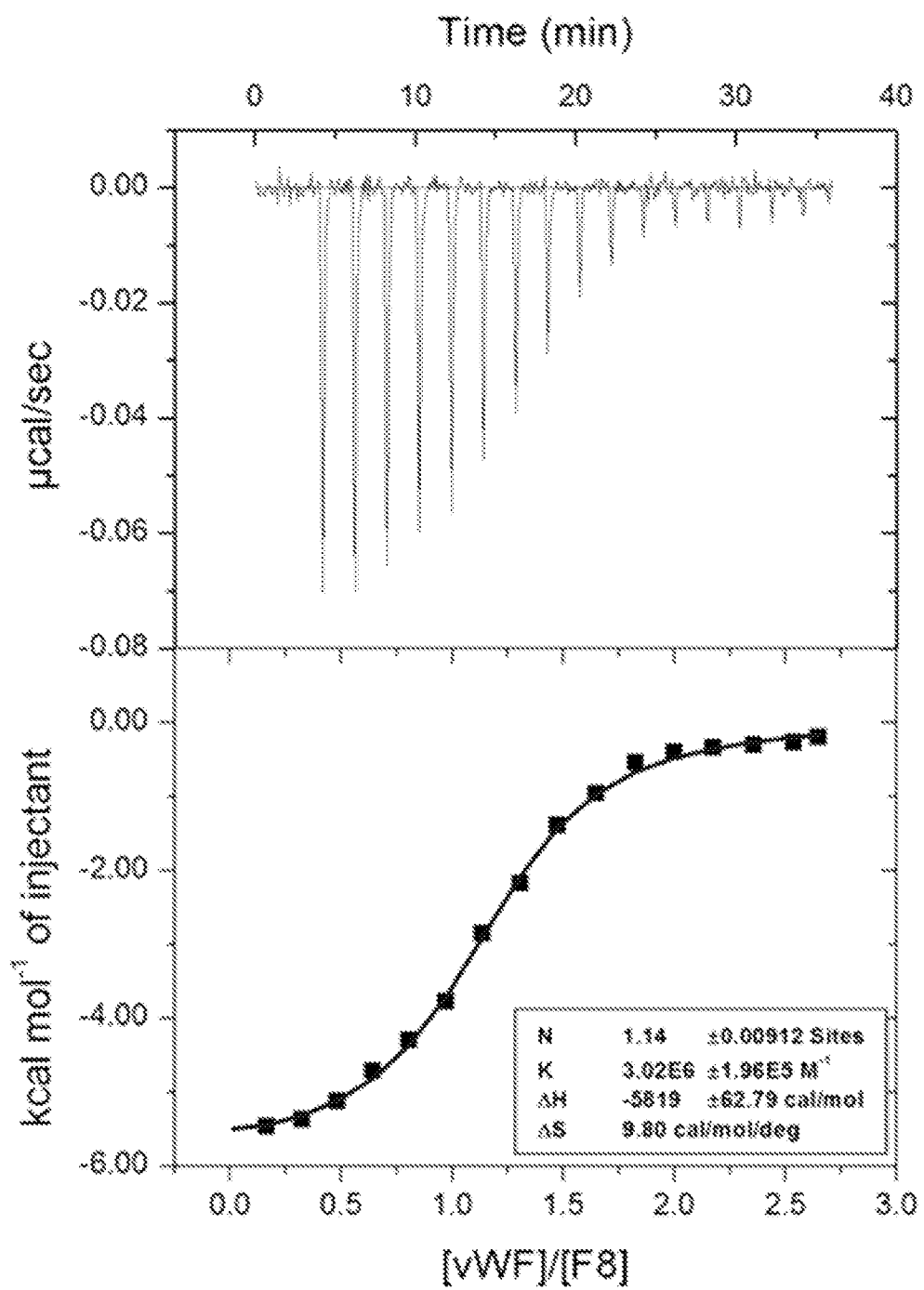
FIG. 9: VWF variant (764-865 SEQ ID NO 5) binding to FVIII (N8, turoctocog alfa) at 20° C. The upper panel shows raw data of heat released upon each titration. Lower panel shows binding isotherm obtained from integrating raw data. Data analysis shows that VWF variant (SEQ ID NO 5) binds to FVIII in an exothermic reaction with a stoichiometry of 1.14, $\Delta H$ of $-5.82$ kcal/mole, $\Delta S$ of 9.8 cal/mol/deg and a $K_d$ of 0.33 µM. "F8/N8/turoctocog alfa" is a B domain truncated FVIII molecule produced as disclosed in Example 1 in WO2009108806.

Evaluation of VWF Fragments Binding to FVIII by Using Isothermal Titration Calorimetry All protein samples are dialyzed in 50 mM Hepes pH 7.4, 150 mM NaCl, 10 mM $CaCl_2$ buffer. Each iTC experiment involves filling the iTC cell with FVIII (approximately 250 μL) and the syringe with VWF variants (approximately 40 μL). Temperature is set as required and the protein sample is allowed to equilibrate under given experimental conditions (approximately 10 minutes). Typically 17-20 injections (of 2-2.5 μL) of VWF variants into cell, containing FVIII, are performed. The first injection is always of 0.2 μL and is discarded from the final data analysis in order to account for diffusion during equilibration step. Stirring speed is set between 700-1000 rpm. Filter period for data collection is 5 sec with a high feedback mode setting. Each titration is spaced by 120 sec. Appropriate control experiments are performed. Raw data is processed to set baseline and integrated to obtain a final isotherm. This binding isotherm is fit to a single-site model to yield $K_d$, stoichiometry (n), $\Delta H$, and $\Delta S$ values to complete characterization of VWF variant binding to FVIII. An example binding isotherm is shown in FIG. 9. These data are being used for determining the optimal concentrations of the FVIII and the VWF fragment in co-formulations intended for subcutaneous administrations.

Example 24

Subcutaneous Administration in FVIII Knockout Mice

Test compounds were prepared as follows: Test compounds were formulated in 18 mg/ml NaCl, 3 mg/ml saccharose, 1.5 mg/ml L-histidine, 0.1 mg/ml polysorbate 80, 0.25 mg/ml CaCl2, pH ~7.3. For test formulations containing VWF or VWF fragments the % FVIII bound by VWF in the co-formulation was calculated using the available IC50 (Ki) values as described above in example 21 (table 6) assuming $K_i=K_d$ or the $K_d$ values obtained as described in example 23.

FVIII KO mice, exon 16 knock-out in a mixed background of C57Bl/6 and SV129, bred at Taconic M&B (B6.129S4-F8tm1Kaz/J) with an approximate weight of 22 g were dosed subcutaneously in the flank with FVIII in combination with various proteins, 6-9 mice with each test compound. The dose volume was 5 ml/kg or 0.25 ml/kg if indicated in table 7.

Blood was sampled at 9 time points from 0-96 h, n=2-3 mice/time point, 3 blood samples from each mice in a sparse sampling regime. The mice were anaesthetized by Isoflurane/$O_2$/$N_2O$ prior to blood sampling via the retroorbital plexus. 45 µl of blood was stabilised with 5 µl of sodium-citrate (0.13 M) and added 200 µl FVIII Coatest SP buffer (50 mM TRIS-HCl, 1% BSA, Ciprofloxacin 10 mg/L, pH 7.3). After centrifugation at 4000 g for 5 minutes at room temperature, the supernatants were immediately frozen on dry ice before storage at −80° C. prior to analysis.

Samples were analysed with regards to FVIII chromogenic activity as described by Ovlisen K et al. J. Thromb. Haemost, 2008, 6: 969-975 and by FVIII antigen analysis using two FVIII light chain antibodies (4F45 and 4F11) in a FVIII LOCI assay (Luminescence oxygen channelling immunoassay).

Mean plasma concentration versus time data were analysed by non-compartmental analysis using WinNonlin Phoenix (Pharsight Corporaton) estimating the given pharmacokinetic parameters. The bioavailability was estimated using a previous i.v. pharmacokinetic study of N8 or N8-GP in the FVIII KO mouse strain.

Figure 7:
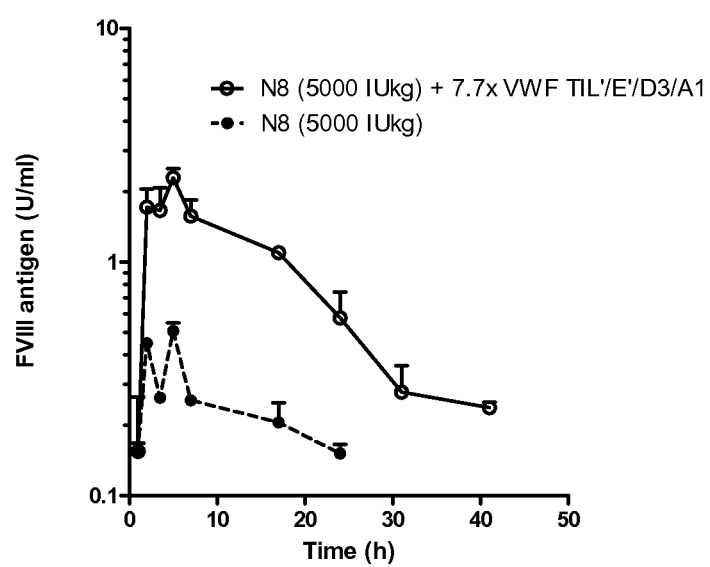
FIG. 7: FVIII antigen in plasma after subcutaneous administration of 5000 IU/kg FVIII (N8, turoctocog alfa) with or without co-administration of 7.7 times the molar dose of VWF TIL'/E'/D3/A1 relatively to FVIII. Data are mean and standard deviation of measurements from n=2 FVIII KO mice per time point.
Figure 8:
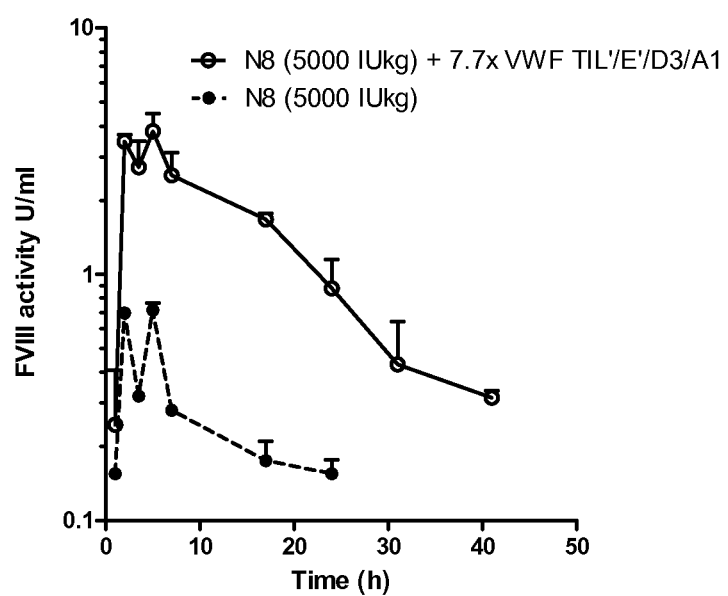
FIG. 8: FVIII activity in plasma after subcutaneous administration of 5000 IU/kg FVIII (N8, turoctocog alfa) with or without co-administration of 7.7 times the molar dose of VWF TIL'/E'/D3/A1 relatively to FVIII. Data are mean and standard deviation of measurements from n=2 FVIII KO mice per time point.

The s.c. FVIII bioavailabilities of the test compounds are shown in table 7 below and in FIGS. 7 and 8.

TABLE 7

FVIII Bioavailability values of a series of different FVIII molecules and FVIII/VWF fragment co-formulations obtained with s.c. administration in FVIII k/o mice.

| FVIII | FVIII Dose | Co-Formulation Protein | Molar Ratio | FVIII Saturation | F % |
|---|---|---|---|---|---|
| Turoctocog alfa | 5000 | (764-1464) monomer VWF | 1 | 87% | 7.3 |
| rFVIII derived from the full-length sequence (Kogenate ®) | 2500 | (764-1464) Dimer VWF | 1 | 82% | 7.4 |
| Turoctocog alfa | 2500 | (764-1250) Monomer VWF | 1 | 82% | 7.6 |
| Turoctocog alfa | 2500 | (764-1041) Monomer VWF | 34 | 82% | 7.8 |
| Turoctocog alfa | 2500 | (764-828) Monomer VWF | 1 | 12% | 1.4 |
| Turoctocog alfa | 2500 | (764-865) Monomer VWF | 1 | 12% | 2.7 |
| Turoctocog alfa | 2500 | (764-1045) Monomer VWF | 1 | 12% | 2.0 |
| Turoctocog alfa | 2500 | (764-865) Monomer VWF | 34 | 83.3% | 4.3 |
| Turoctocog alfa | 2500/ 0.25 ml/kg | (764-1041) Monomer VWF | 3x | 85.5% | 5.03 |
| Turoctocog alfa | 2500/ 0.25 ml/kg | (764-865) Monomer VWF | 3x | 86.5% | 1.9 |
| Turoctocog alfa | 2500/ 0.25 ml/kg | (764-1464) Dimer VWF | 1x | 99% | 8.4 |
| Turoctocog alfa | 2500 | (764-1464) Murine monomer VWF | 1 | 82% | 5.6 |
| Turoctocog alfa | 2500 | Human serum Albumin | 611 | Not applicable | 3.7 |
| Turoctocog alfa | 2500 | plasma derived full length VWF | 1 | 99% | 0.0 |
| Turoctocog alfa | 5000 | (764-1464) monomer VWF | 7.7 | 99% | 8.2 |
| Turoctocog alfa | 5000 | (764-1464) monomer VWF | 3 | 99% | 6.7 |
| Turoctocog alfa | 5000 | (764-1464) monomer VWF | 1 | 87% | 7.3 |
| Turoctocog alfa | 5000 | None | Not applicable | Not applicable | 2.3 |
| FVIII with a 226 aa B domain | 5000 | None | Not applicable | Not applicable | 4.3 |
| FVIII with a-226 aa B domain | 5000 | (764-1464) monomer VWF | 7.7 | 0.99 | 7.0 |
| N8-GP | 2500 | (764-1464) monomer VWF | 1 | 0.82 | 27 |
| N8-GP | 10000 | (764-1464) monomer VWF | 7.7 | 0.99 | 47 |
| N8-GP | 2500 | (764-1464) monomer VWF | 7.7 | 0.99 | 36 |
| N8-GP | 2500 | (764-1464) Dimer VWF | 1 | 0.99 | 33 |
| FVIII-K1804-Hep157 | 2500 | (764-1464) monomer VWF | 1 | 0.82 | 50 |

TABLE 7-continued

FVIII Bioavailability values of a series of different FVIII molecules and FVIII/VWF fragment co-formulations obtained with s.c. administration in FVIII k/o mice.

| FVIII | FVIII Dose | Co-Formulation Protein | Molar Ratio | FVIII Saturation | F % |
|---|---|---|---|---|---|
| FVIII-K1804-Hep157 | 2500 | None | Not applicable | Not applicable | 27 |
| PSA40Kd-O-Glycan-N8 | 2500 | (764-1464) monomer VWF | 1 | 0.82 | 8.8 |
| PSA40Kd-O-Glycan-N8 | 2500 | None | Not applicable | Not applicable | 6.1 |
| 40kDa-PEG-FVIII-K2092A + F2093A | 10000 | None | Not applicable | Not applicable | 20 |
| N8-GP | 10000 | 4F30 FVIII reduced uptake antibody | 5 | 0.99 | 11 |
| N8-GP | 1000 | Hirudin | 0.5 mg/kg | Not applicable | 7.6 |
| N8-GP | 10000 | Hyaluronidase | 0.5 activity ratio | Not applicable | 8.4 |
| N8-GP | 20000 | None | Not applicable | Not applicable | 28 |
| N8-GP | 10000 | None | Not applicable | Not applicable | 19 |
| N8-GP | 2500 | None | Not applicable | Not applicable | 14 |
| N8-GP | 1000 | None | Not applicable | Not applicable | 17 |

The left column "FVIII" denotes the FVIII compound used in the experiment.
The column labelled "FVIII dose" denotes the FVIII dose (IU/kg) used in the experiment,
the column labelled "co-formulation protein" denotes the co-formulated protein (if any) used in the experiment.
The column labelled "Molar ratio" denotes the molar ratio to FVIII of the protein in the co-formulation.
The column labelled "FVIII Saturation" denotes the calculated fraction of FVIII that is binding the co-formulated protein at the concentrations used in the experiment.
The column labelled "F %" denotes the bioavailability of FVIII obtained in the experiment.

The s.c. bioavailability of FVIII co-formulated with a VWF fragment appear to depend on the saturation of the FVIII VWF binding sites in the co-formulation rather than on the VWF fragment length. The shortest VWF fragment, wherein a >80% saturation of FVIII was achieved, was 764-865—this formulation displayed a FVIII bioavailability of 4.3% (34 molar excess of N8/turoctocog alfa over VWF fragment). The longest VWF fragment tested, under similar conditions with respect to saturation, was the 764-1464 fragment which resulted in a FVIII bioavailability of 7.3%. The dimer form of the 764-1464 dosed in a lower volume of 0.25 ml/kg resulted in a FVIII bioavailability of 8.4%.

Fragments shorter than 764-1250, which do not contain the entire D3 region, bind FVIII with a higher IC50 ($K_i$) than longer fragments. Thus, 1 to 1 molar formulation of FVIII and VWF fragments shorter than 764-1250 displayed lower FVIII bioavailabilities, i.e. less than 4%.

The s.c. FVIII bioavailability-improving effect of VWF fragments according to the invention may thus be obtained by saturation of the FVIII VWF binding sites with VWF-fragment. Short VWF fragments with relatively low FVIII binding affinity should thus be used in higher ratios compared to longer VWF fragments with better binding FVIII binding properties in order to obtain a high degree of bioavailability.

FVIII derived from the full-length sequence (Kogenate®) displayed the same degree of bioavailability as FVIII with a truncated B domain (turoctocog alfa/N8) when co-formulated with the 764-1464 VWF fragment. This indicates that high FVIII bioavailability is not dependent on co-formulation with turoctocog alfa/N8 but is dependent on presence of the VWF fragment.

Co-formulation of FVIII (turoctocog alfa/N8) with full-length plasma-derived human VWF resulted in FVIII bioavailability of about 0% thus demonstrating that only fragments of VWF are able to enhance bioavailability of FVIII. The reason for the lack of effect of the full-length VWF may be due to the presence of collagen binding site in the A3 domain which may result in binding and entrapment of. Preferred VWF fragments according to the present do thus not comprise the A3 domain. Alternatively or additionally, the multimerisation capabilities of full-length VWF produces large multimers that restricts systemic absorption due to size of the complex. The data indicates that also longer VWF fragments (preferably without the A3 domain) than those tested in table 7 will have the same beneficial effect on FVIII bioavailability.

Serum albumin did not improve the s.c. bioavailability of FVIII (turoctocog alfa/N8). Thus, presence of additional protein in a FVIII formulation does not appear to increase the s.c. bioavailability of FVIII—unless this protein is a VWF fragment according to the present invention.

VWF dose was not critical for FVIII s.c. bioavailability as seen for molar ratios between 1:1 and 1:7.7 of FVIII:VWF fragment. The critical factor for achieving a high FVIII bioavailability thus appear to be a high degree of FVIII saturation (binding) with VWF fragment. All compositions in these experiments comprising a calculated saturation of N8 of at least 86.8% thus resulted in similar bioavailabilities. VWF fragments according to the invention may thus protect FVIII at the s.c. injection site.

FVIII with a 226 amino acid (aa) B domain (SEQ ID NO 3), displayed a higher s.c. FVIII bioavailability than turoctocog alfa/N8. However, bioavailability of this FVIII with a 226 aa B-domain was comparable to turoctocog alfa/N8 in connection with s.c. co-administration with the VWF-fragment 764-1464 (TIL'/E'/D3/A1) monomer. It may thus be speculated that the additional amino acids in the 226 aa B-domain (compared to turoctocog alfa/N8) may protect clearance sites of FVIII in connection with extravascular administration thereof, meaning that such FVIII molecules might be used for s.c. administration with or without VWF according to the present invention.

FVIIIK1804C-HEP157, displayed a bioavailability of 50% dosed in co-administration with the VWF-fragment 764-1464 (TIL'/E'/D3/A1) monomer and a bioavailability of 27% dosed alone. PSA40 Kd-O-Glycan-N8, displayed a bioavailability of 8.8% dosed in co-administration with the VWF-fragment 764-1464 (TIL'/E'/D3/A1) monomer and 6.11% dosed alone. It may thus be speculated that conjugation of FVIII molecules with Heparosan polymers and/or Polysialic acid polymers either protects FVIII against breakdown/uptake in the sub cutis or enhances s.c. absorption. Heparosan appear to be more effective than Sialic acid polymers in enhancing the s.c. bioavailability. Both FVIII variants displayed higher bioavailability's when dosed together with VWF fragment.

N8-GP and FVIIIK1804C-HEP157+764-1464 (TIL'/E'/D3/A1) monomer and dimer, resulted in the highest bioavailability obtained. Bioavailability of N8-GP may thus be increased by increasing the dose or the concentration in the co-formulation. Dose volume was 5 ml/kg in all dosing's, thus the N8-GP concentration in the dosing solution was 2 times higher in the 20000 IU/kg dosing than in the 10000 IU/kg dosing. This resulted in 28% and 19% bioavailability respectively.

The 764-1464 dimer VWF fragment does not contain any mutations. The 764-1464 dimer VWF fragment binds stronger to Turoctocog alfa and N8-GP (table 6) but result in a similar bioavailability of FVIII as the monomer version of the fragment. This indicates that substituting Cys1099 and/or Cys1142 in the VWF fragments according to the invention does not influence the bioavailability of FVIII. Also, the binding affinity of VWF fragments to N8-GP does not influence the effect on bioavailability of N8-GP as long as more than 80% of the FVIII molecules are in complex with VWF fragment in co-formulation. Additionally, since the dimer version of VWF fragment 764-1464 improves the bioavailability, the maximum molecular weight of a desired VWF fragment may be equal to or larger than 158.8 KDa.

Co-formulation of N8-GP with hyaluronidase did not increase the FVIII bioavailability, indicating that the Hyaluron network in the extracellular matrix in the subcutis is not hindering the passage of FVIII into the bloodstream. Likewise, Hirudin dosed to a level that inhibits thrombin activity in vivo did not affect bioavailability of N8-GP. Thrombin activation of FVIII does thus not appear to affect s.c. FVIII bioavailability.

The antibody 4F30 (further characterised in WO2012035050), which bind to C1 and inhibits cellular uptake of FVIII, did not improve the bioavailability of N8-GP. In this formulation, 2000 IU/ml N8-GP was co-formulated with 1 mg/ml of 4F30 which means that 99.6% of FVIII was bound to the mAb also after in vivo dilution assuming a $K_d$ of 0.6 nM, an in vivo dilution of 20×, a molecular weight for FVIII (turoctocog alfa/N8) of 170000 g/mol, a specific activity of 10000 IU/mg for turoctocog alfa/N8, and a molecular weight for 4F30 of 150000 g/mol. Also, the PEGylated FVIII with K2092A+F2093A mutations displayed decreased uptake in cells but the mutations did not improve the bioavailability compared to N8-GP. Inhibition of cellular FVIII uptake does thus not appear to be the mechanism by which co-formulated VWF fragments result in increased s.c. bioavailability of FVIII.

Example 25

Subcutaneous Administration in New Zealand White Rabbits

Test compounds were formulated in 18 mg/ml NaCl, 3 mg/ml saccharose, 1.5 mg/ml L-histidine, 0.1 mg/ml polysorbate 80, 0.25 mg/ml $CaCl_2$, pH ~7.3. For test formulations containing VWF or VWF fragments the % FVIII bound by VWF was calculated using the available IC50 values (table 6) assuming $1C50=K_i=K_d$.

Female New Zealand white rabbits weighing approximately 2-3 kg were used for the study. The animals were allowed free access to feed and water. The rabbits were dosed subcutaneously over the thigh with FVIII in combination with various proteins, 4-5 rabbits with each test compound. The dose volume was 0.2 ml/kg or 1 ml/kg.

Blood was sampled at 11 time points from 0 to 96 h with n=4-5 rabbits/time point. At each sampling time point, 1 ml blood was sampled from an ear artery by use of a 21G needle and EDTA coated tubes. The tubes were centrifuged within 10 minutes after blood drawing at 4000 G for 5 minutes and plasma separated The samples were immediately frozen on dry ice before storage at −80° C. prior to analysis. The samples were analysed by FVIII antigen analysis using two FVIII light chain antibodies (4F45 and 4F11) in a FVIII LOCI assay (Luminescence oxygen channeling immunoassay).

Mean plasma concentration versus time data were analysed by non-compartmental analysis using WinNonlin Phoenix (Pharsight Corporation) estimating the given pharmacokinetic parameters. The bioavailability was estimated using pharmacokinetics of FVIII (turoctocog alfa/N8) and N8-GP administered i.v. to rabbits.

The obtained bioavailabilities are shown in table 8.

TABLE 8

| FVIII | FVIII Dose/dose volume | co formulation protein | Molar ratio co-formulation protein:FVIII | Saturation FVIII with co-formulated protein (%) | F % |
|---|---|---|---|---|---|
| FVIII (turoctocog alfa/N8) + VWF | 2000/0.2 ml/kg | TIL'/E'/D3/A1 | 3 | 99 | 6.2 |
| N8-GP | 700/0.2 ml/kg | — | — | — | 40 |
| N8-GP + VWF | 700/0.2 ml/kg | TIL'/E'/D3/A1 | 3 | 99 | 59 |
| N8-GP + VWF | 500/1 ml/kg | TIL'/E'/D3/A1 | 3 | 82 | 34 |

The s.c. bioavailability in rabbits of N8-GP and N8-GP co-formulated with VWF fragment TIL'/E'/D3/A1 dosed in a dosing volume of 0.2 ml/kg was 40 and 59%, respectively. The bioavailability of N8-GP+VWF dosed in a dosing volume of 1 ml/kg was 34%. The bioavailability of N8-GP may thus be influenced either by the species or by the differences in dosing volumes (5 ml/kg in mice and 0.2 ml/kg or 1 ml/kg in rabbits). 0.2 ml/kg is closest to a dosing volume relevant for humans. FVIII (turoctocog alfa/N8) dosed together with VWF fragment TIL'/E'/D3/A1 displayed a similar bioavailability in rabbits compared to mice despite the higher dosing concentration.

Example 26

Construction of Expression Vectors Encoding VWF Fragments

Plasmid #796 consisting of the pZEMHygro vector with insert consisting of wild-type human VWF cDNA was utilized as the starting point for generating DNA constructs for the expression of truncated human VWF proteins.

DNA encoding the VWF signal peptide, followed by the VWF TIL'E' domain, the VWF D3 domain, the VWF A1 domain, and a HPC4 tag was generated by polymerase chain reaction (PCR) using plasmid #796 as template, forward primer oLLC089 VWF forward, and reverse primer oLLC092 VWF A1 HPC4 reverse. These primers contain a Nhe I and a Not I restriction site, respectively. The resulting PCR product was inserted into the pCR2.1-TOPO vector (Invitrogen). From here the VWF(TIL'/E'/D3/A1)-HPC4 coding DNA was excised with the Nhe I and a Not I restriction enzymes and inserted into pZEM219b digested with the same restriction enzymes. Thus, the pLLC089 construct was established consisting of pZEM219b with insert encoding VWF (TIL'/E'/D3/A1)-HPC4.

Nucleotide substitutions leading to the amino acid replacements C1099/1142S in the VWF VWF(TIL'/E'/D3/A1)-HPC4 protein encoded by pLLC089 were introduced by site-directed mutagenesis of pLCC089 using the QuikChange XL Site-directed Mutagenesis kit (Stratagene) and the oLLC101-f, oLLC102-r, oLLC103-f, and oLLC104-r mutagenesis primers. The site directed mutagenesis gave rise to the pLLC095 vector consisting of pZEM219b with insert encoding VWF (TIL'/E'/D3/A1)C1099/1142S-HPC4.

BHK cell line producing VWF (TIL'/E'/D3/A1)C1099/1142S-HPC4. The cells were seeded in a biofermentor and the VWF (TIL'/E'/D3/A1)C1099/1142S-HPC4 protein was purified from the cell culture supernatant as described in Example 22.

CHO-DUKX-B11 suspension cells grown in suspension were transfected with pLLC095 by electroporation. A pool of transfected cells was generated by adaptation to growth in medium without nucleosides. Subsequently, the pool was adapted to growth in the presence of 100 mM methotrexate giving rise to the VWF (TIL'/E'/D3/A1)C1099/1142S-HPC4 producing non-clonal CHO-DUKX-B11 cell line MBML001. The cells were seeded in a biofermentor and the VWF (TIL'/E'/D3/A1)C1099/1142S-HPC4 protein was purified from the cell culture supernatant as described in Example 22.

Example 28

VWF Fragments Protects FVIII Against Cellular Uptake

The effect of plasma-derived (pd) VWF and fragments of VWF on FVIII cellular uptake is evaluated in human monocyte-derived macrophages or dendritic cells, which both are antigen presenting cells, or U87 MG cells. U87 MG cells are obtained from ATCC (HTB-14). The cells are cultured in fibronectin-coated 24-well plates for 48 hours in EMEM supplemented with 10% heat inactivated FCS at 37° C. in 5% $CO_2$ The cells are carefully washed with buffer A (10 mM HEPES, 150 mM NaCl, 4 KCl, 11 mM Glucose, pH 7.4) and incubated for 15 min with buffer B (buffer A supplemented with 5 mM $CaCl_2$ and 1 mg/ml BSA). Radioactively labelled FVIII ($^{125}$I-FVIII, final concentration 1 nM) is incubated alone or premixed with different concentrations of pdVWF (American Diagnostica, final concentration 0.001 nM-50 nM based on monomer content) or TIL'/E'/D3/A1 (final concentration 0.25 nM -500 nM or 1000 nM) 10 min prior to addition

TABLE 9

Oligonucleotide primers used for generating VWF fragment coding DNA contructs

| Primer name | Primer sequence (5'-3') |
| --- | --- |
| oLLC089 VWF forward | CCGCTAGCCCATGATTCCTGCCAGATTTGCCGGGGTGCTGCTTGCTCT GGCCCTCATTTTGCCAGGGACCCTTTGTAGCCTATCCTGTCGGCCCCCC ATG (SEQ ID NO 39) |
| oLLC092 VWF A1 HPC4 reverse | GATGCGGCCGCCTACTACTATTTGCCATCAATCAGACGCGGATCCACCT GATCTTCGGCTTCAGGGGCAAGGTCACAGAGGTAGC (SEQ ID NO 40) |
| oLLC101-f | CATTGGGGACTGCGCCTCCTTCTGCGACACCATTGCTGCC (SEQ ID NO 41) |
| oLLC102-r | GGCAGCAATGGTGTCGCAGAAGGAGGCGCAGTCCCCAATG (SEQ ID NO 42) |
| oLLC103-f | CGGGAGAACGGGTATGAGTCTGAGTGGCGCTATAACAGCTGTGC (SEQ ID NO 43) |
| oLLC104-r | GCACAGCTGTTATAGCGCCACTCAGACTCATACCCGTTCTCCCG (SEQ ID NO 44) |

Example 27

Stable Cell Lines Expressing VWF Fragments

Baby hamster kidney (BHK) cells grown in Dulbecco's modified Eagle's medium with 10% fetal calf serum were transfected with pLL095 using Genejuice transfection reagent (Merck). A pool of transfected cells was generated by selection with 1.5 M methotrexate giving rise to a non-clonal to the U87 MG cells and incubated with the cells 1 hour at 37° C. to allow binding and internalization. Cells are subsequently washed three times with ice-cold buffer B. Surface bound proteins are cleaved off by incubating the cells in PBS containing 100 μg/ml trypsin, 50 μg/ml proteinase K, 5 mM EDTA (pH 7.4) for 1 hour on ice. The detached cells are transferred to tubes and centrifuged to pellet the cells. The supernatant representing the cell bound FVIII is transferred to new tubes. The radioactivity in tubes with the supernatants (bound FVIII) and cell pellets (internalized FVIII) are quantified in a gamma counter, and values calculated in FVIII concentration by using a standard curve based on $^{125}$I-FVIII. Bound $^{125}$I-FVIII in the absence of VWF are set to 100%.

Dendritic cells and macrophages are differentiated from monocytes isolated from buffy coats by magnetic separation using magnetic anti-CD14-beads (Miltenyi Biotec) and a MACS column (Miltenyi Biotec) according to the manufactures instructions. Monocytes ($0.5 \times 10^6$ cells/ml) are seeded in T-75 tissue culture flasks and cultured in IMDM media (GIBCO) containing 10% FBS, 1% penicillin/streptomycin and 3.3 ng/ml M-CSF (R&D Systems) in order to differentiate the cells into macrophages. Additional 3.3 ng/ml M-CSF is added after three days of culturing. The monocytes can alternatively be differentiated into dendritic cells by stimulating with 40 ng/ml GM-CSF (R&D Systems) and 40 ng/ml IL-4 for five days. Dendritic cells are washed in buffer B and transferred to low binding Nunc tubes with $0.5 \times 10^6$ cells/tube. Fluorescently labelled FVIII, e.g. Oregon-Green FVIII (e.g. 30 and 100 nM) are added and incubated 1 hour at 37° C. Cells are washed once and analysed by flow cytometry using a LRS Fortessa instrument (BD). The macrophages are after six days culturing washed with PBS and incubated 10-20 min at 4° C. with 2.5 mM EDTA in PBS with 5% FCS to detach cells. Macrophages ($7 \times 10^5$/well) are seeded on fibronectin-coated 96-well glass bottom tissue culture plates (Perkin Elmer ViewPlate Black). 24 hours post seeding the cells are washed once with buffer B before addition of 30 nM fluorescently-labelled FVIII (e.g. OregonGreen-FVIII) alone or in the presence of increasing concentrations (15-240 nM) of pdVWF (American Diagnostica) or TIL'/E'/D3/A1. Macrophages are incubated for 1 hour at 37° C. Subsequently, cells are washed twice with buffer B to remove non-internalized material before addition of PBS containing 2.5 µg/ml Hoechst33342 (Molecular Probes) to visualize the cell nuclei. The plate is then immediately imaged on the Operetta® High Content Screening system (Perkin Elmer, Hamburg) in widefield fluorescence mode using the 20× high NA objective. Ten fields per well are imaged and analysed. The approach to image analysis in the Harmony® software is based on counting nuclei (Hoechst channel), followed by texture analysis (FVIII channel) using the "find particle"' method to detect vesicular FVIII. Dead or apoptotic cells are excluded from the analysis based on nuclei fragmentation and/or excessive binding of FVIII to the plasma membrane. In order to quantify the internalized FVIII the integrated fluorescent intensity of the vesicular FVIII signal is calculated and plotted against time.

IC50 values for inhibition of FVIII binding and internalization in U87 MG cells and macrophages are shown in table 10. Both pdVWF and TIL'/E'/D3/A1 are able to inhibit FVIII cell binding/uptake in both cell types providing sufficient high concentrations are used. As uptake in antigen presenting cells is the initial step in presenting FVIII to the immune system, the data may indicate that a reduced immune response can be achieved upon co-formulation of FVIII with a VWF fragment.

TABLE 10

Effect of pdVWF and TIL'/E'/D3/A1 fragment on FVIII binding and internalization in U87 MG cells and uptake in macrophages.

| Cell type | IC50 (nM) | | Maximal inhibition (%) | |
| --- | --- | --- | --- | --- |
| | pdVWF | TIL'/E'/D3/A1 | pdVWF | TIL'/E'/D3/A1 |
| U87 (n = 3-4) Binding | 1.2 ± 0.9 | 17.6 ± 13.0 | 34.3 ± 4.2 | 39.8 ± 7.8 |

TABLE 10-continued

Effect of pdVWF and TIL'/E'/D3/A1 fragment on FVIII binding and internalization in U87 MG cells and uptake in macrophages.

| Cell type | IC50 (nM) | | Maximal inhibition (%) | |
| --- | --- | --- | --- | --- |
| | pdVWF | TIL'/E'/D3/A1 | pdVWF | TIL'/E'/D3/A1 |
| U87 (n = 3-4) Internalization | 1.3 ± 1.2 | 22.1 ± 19.2 | 32.2 ± 7.0 | 41.2 ± 11.5 |
| Macrophages (n = 3) | 15.6 ± 3.5 | 31.5 ± 6.1 | 32.6 ± 11.4 | 47.2 ± 11.7 |

Example 29

Efficacy of FVIII Compounds Co-Formulated with VWF Variants after Subcutaneous Dosing:

FVIII deficient, FVIII-KO mice, 12-16 weeks old, male and females are divided into 3 groups of 12 animals. In each group, eight animals are subjected to tail bleeding and 4 animals are used in parallel for ex vivo efficacy testing using ROTEM analysis.

GlycoPEGylated FVIII or vehicle is dosed s.c. 24 hr prior to tail transection. As a positive control glycoPEGylated FVIII is dosed i.v. 5 min prior to injury. The s.c injection is performed in the neck and the i.v. injection in a lateral tail vein. The dose volume is 5 ml/kg.

GlycoPEGylated FVIII is prepared in buffer (10 mM L-Histidine, 8.8 mM Sucrose, 0.01% Polysorbate 80, 308 mM NaCl, 1.7 mM $CaCl_2$ (dihydrate), 0.01% Polysorbate 80 0.1 mg/ml, pH 6.9) to a concentration of 40 and 500 IU/ml and stored at −80° C. until use.

Before tail transection, the mice are anaesthetised with isoflurane and placed on a heating pad. The tails are placed in pre-heated saline at 37° C. for 10 min. The tail is transected 4 mm from the tip.

Immediately before tail transection a 20 µl blood sample is drawn from the peri-orbital plexus for FVIII determination.

Blood is collected over 30 min and the haemoglobin concentration determined by spectrophotometry at 550 nm.

Parallel animals are used for blood sampling and subsequent analysis of their clotting parameters (ex vivo efficacy). A blood sample is taken from the peri-orbital plexus with 20 µL capillary tubes without additive. The blood sample is diluted 1:10 in 0.13M sodium citrate and carefully mixed and stored at rum temperature for immediate thromboelastography by ROTEM. The blood sample is re-calcified by adding 7 µL $CaCl_2$ to a mini curvet (StarTEM). Thereafter, 105 µL of blood is added to the mini curvet and mixed. The analysis is performed until the maximum amplitude is reached.

Results:

The prophylactic effect of s.c. administered FVIII is determined by comparing the blood loss during the 30 min study period at 24 hr after s.c. administration to that of 1) a vehicle control group and 2) an i.v. control group with glycoPEGylated FVIII. The blood loss in the group dosed s.c. with glycoPEGylated FVIII is comparable to the blood loss in the group dosed i.v. (FIG. 10, left panel). The blood loss data are supported by the ex vivo efficacy parallel study of the examined clotting parameters, e.g. clot time (FIG. 10, right panel).

In conclusion, subcutaneously administered FVIII appear to be hemostatically active based on the PK profile and the results from the ex vivo activity. Therefore, subcutaneously administered FVIII co-formulated with a VWF fragment is

Example 30

Effect of s.c. Administered FVIII±VWF Fragments in FVIII-Deficient Mice.

Test Compounds: Test compounds are prepared in 10 mM L-Histidine (1.55 mg/ml), 8.8 mM Sucrose (3.0 mg/ml), 308 mM NaCl (18 mg/ml), 1.7 mM CaCl2 dihydrate (0.25 mg/ml), 0.01% Polysorbate 80 (0.1 mg/ml), pH 7.3.

Animals: Experiments are performed using groups of F8 knockout (FVIII k/o) mice (129/C57BL/6 or C57BL/6, exon 16 disrupted). Animals are included in experiments when 12-18 weeks old at which time they are weighing roughly 18-25 grams. Twelve to 15 animals are included per group.

Administration of test compounds: Test compounds are administered subcutaneously (or intravenously for controls) using a dose volume of maximally 10 ml/kg (or 5 ml/kg for controls).

Bleeding Model: A tail vein transection (TVT) bleeding model is conducted with the mice under full isoflurane anaesthesia. Briefly, following anaesthesia the bleeding challenge comprises a template-guided transection of a lateral tail vein at a tail diameter of 2.7 mm. The tail is immersed in saline at 37° C. allowing visual recording of the bleeding for 60 min, where after the blood is isolated and the blood loss determined by measuring the haemoglobin concentration as described in "Example 3". When feasible and justified, blood is sampled for assessment of FVIII activity (FVIII:C) in plasma as described above.

Dose Response: Different doses of FVIII or FVIII co-formulated with VWF fragments (e.g. N8-GP/VWF) are injected subcutaneously at defined time point(s) prior to TVT. Vehicle and intravenous control/treatment groups are included for no effect and maximal effect, respectively.

Duration of Action: FVIII or FVIII/VWF is injected s.c. to identify prolonged effect, i.e. improved bleeding phenotype after treatment. TVT is performed at several time points, e.g. 24, 48, 72, 96, after dosing.

Repeated Dose: FVIII or FVIII/VWF fragment is dosed s.c. once daily for several days. TVT is performed at different time points to assess any improvement in the bleeding phenotype.

Data Processing and Analyses: Data are physically recorded throughout the experiment. Hereafter, data are aggregated for analysis using MS Excel (Microsoft, Wash., USA) before being analysed in GraphPad Prism version 5 (GraphPad Software, Inc, CA, USA).

Example 31

Effect of s.c. FVIII±VWF Fragments in Other FVIII-Deficient Species.

Additional pharmacodynamic experiments are conducted in other species to verify effect after subcutaneous administration in non-murine animal models of haemophilia A, e.g. rat and dog. FVIII or FVIII/VWF are injected subcutaneously before assessing ex vivo effect, before inducing a bleeding challenge, or as a means to treat or prevent spontaneous bleeds.

Test Compounds: Test compounds are prepared in 10 mM L-Histidine (1.55 mg/ml), 8.8 mM Sucrose (3.0 mg/ml), 308 mM NaCl (18 mg/ml), 1.7 mM CaCl2 dihydrate (0.25 mg/ml), 0.01% Polysorbate 80 (0.1 mg/ml), pH 7.3.

Animals: Experiments are performed in adolescent rats (~12 weeks old) or dogs (6+ months old) with haemophilia A.

Administration of test compounds: Test compounds are administered subcutaneously (or intravenously for controls) using a dose volume of maximally 10 ml/kg (or 5 ml/kg for controls).

Dog effect model: In dogs with haemophilia A the effect is assessed ex vivo using surrogate markers, e.g. thrombelastography as previously described (Knudsen et al, 2011; Haemophilia, 17, 962-970), or in vivo, e.g. using a standardized bleeding challenge monitored by acoustic force radiation force impulse (ARFI) ultrasound as described (Scola et al, 2011; Ultrasound in Med. & Biol., 37(12), 2126-2132). Capacity allowing, test compound are administered to treat spontaneously bleeding dogs. Effect is monitored by assessing the resolution of clinical manifestation in comparison with historic data on i.v. treatment.

Rat effect model: In rats with haemophilia A the effect is assessed ex vivo using surrogate markers, e.g. thrombelastography as described above for mice and dogs, or in vivo, e.g. using a standardized bleeding challenge as described for mice. Capacity allowing, test compound are administered to treat spontaneously bleeding rats. Effect is monitored by assessing the resolution of clinical manifestation in comparison with historic data on i.v. treatment.

Additional pharmacodynamic experiments are conducted in other species to verify effect after subcutaneous administration in non-murine animal models of haemophilia A, e.g. rat and dog.

Example 32

Construction of Expression Vectors Encoding VWF Fragments

A nucleotide substitution leading to the amino acid replacement S1142C in the VWF(764-1250)-C1099/1142S-ALA-HPC4 protein encoded by pJSV348 described in Example 17 was introduced by PCR-based site-directed mutagenesis using the VWF 1099C S and VWF 1099C AS primers (Table P). This gave rise to the pGB237 vector consisting of pTT5 with insert encoding VWF(764-1250)-C1099S-ALA-HPC4 (SEQ ID NO 11). The cysteine at position 1142 allows dimerization of the protein as described in Example 20.

Likewise, a nucleotide substitution leading to the amino acid replacement S1099C in the VWF(764-1250)-C1099/1142S-ALA-HPC4 protein encoded by pJSV348 described in Example 17 was introduced by PCR-based site-directed mutagenesis using the VWF 1142C S and VWF 1142C AS primers (Table P). This gave rise to the pGB238 vector consisting of pTT5 with insert encoding VWF(764-1250)-C1142S-ALA-HPC4 (SEQ ID NO 11). The cysteine at position 1099 allows dimerization of the protein as described in Example 20.

In a similar manner, the S1099C amino acid replacement was introduced in the VWF(764-1128)-C1099S-HPC4 protein encoded by pJSV406 described in Example 18, giving rise to the pGB249 vector consisting of pTT5 with insert encoding VWF(764-1128)-HPC4 (SEQ ID NO 9). The cysteine at position 1099 allows dimerization of the protein as described in Example 20.

cDNA encoding amino acid 1-1250 of human VWF was amplified by PCR using plasmid #796 (described in Example 26) as template, forward primer JP1000 VWF-HindIII S (Table 2), and reverse primer JP1006 VWF764-1250 (Table 2). Primer JP1006 VWF764-1250 contains a Nhe I site. The resulting PCR product was inserted into the pCR4BLUNT-TOPO vector (Invitrogen) downstream of Pme I restriction site. From here, the vWF(1-1250) coding DNA was excised with the Pme I and a Nhe I restriction enzymes and inserted into pJSV164 described in Example 17 generating the pGB242 vector consisting of pTT5 with insert encoding vWF (1-1250)-ALA-HPC4. The cysteines at position 1099 and 1142 allow dimerization of the protein as described in Example 20, and proteolytic removal of the presequence will generate vWF(764-1250)-ALA-HPC4 (SEQ ID NO 11).

DNA sequences of pJSV348 (described in Example 17) and construct #796 (described in Example 26) were inverse amplified by PCR using overlapping primers. The pJSV348 sequence was amplified using primer 2764pJSV348 and 1202pJSV348R (Table P), while the construct #796 sequence was amplified using primer 221#796F and 3537#796R (Table P). The amplification products from pJSV348 (recipient) and construct #796 (donor) were excised from an agarose gel and joined by ligation independent cloning (LIC) using the In-Fusion HD Cloning Kit (Clontech) to generate circular DNA and subsequently transformed into Stellar competent cells (Clontech). The resulting expression vector, named pGB252 consists of PTT5 with insert encoding VWF(1-1128)-ALA-HPC4. The cystein at position 1099 allows dimerization of the protein as described in Example 20, and proteolytic removal of the presequence will generate vWF(764-1128)-ALA-HPC4 (SEQ ID NO 9).

Likewise, amplification using pJSV348 (described in Example 17) as template with the primers 2764pJSV348 and 1202pJSV348R (Table P) and amplification using #796 (described in Example 26) as template with the primers 221#796F and 3747#796R (Table P) generated pJSV348 (recipient) and construct #796 (donor) amplification products that were also excised from an agarose gel and joined by ligation independent cloning (LIC) using the In-Fusion HD Cloning Kit (Clontech) to generate circular DNA and subsequently transformed into Stellar competent cells (Clontech). The resulting expression vector, named pGB253 consists of PTT5 with insert encoding VWF(1-1198)-ALA-HPC4. The cysteines at position 1099 and 1142 allow dimerization of the protein as described in Example 20, and proteolytic removal of the presequence will generate vWF(764-1198)-ALA-HPC4 (SEQ ID NO 10).

In a similar manner, DNA sequences of pJSV348 (described in Example 17) and construct #796 (described in Example 26) were inverse amplified by PCR using overlapping primers. The pJSV348 sequence was amplified using primer 2764pJSV348 and 2420pJSV348R (Table 11), while the construct #796 sequence was amplified using primer 3666#796F and 5203#796R (Table P). The amplification products from pJSV348 (recipient) and construct #796 (donor) were excised from an agarose gel and joined by ligation independent cloning (LIC) using the In-Fusion HD Cloning Kit (Clontech) to generate circular DNA and subsequently transformed into Stellar competent cells (Clontech). The resulting expression vector, named pGB250 consists of PTT5 with insert encoding VWF(764-1873)-C1099/1142C-ALA-HPC4 (SEQ ID NO 20).

Human VWF cDNA sequences amplified from construct #796 (described in Example 26) were combined generating the pLLC122 vector consisting of pZEM219b with insert encoding vWF (1-1464)-HPC4. The cysteines at position 1099 and 1142 allow dimerization of the protein as described in Example 20, and proteolytic removal of the presequence will generate vWF(764-1464)-HPC4 (SEQ ID NO 19).

TABLE 11

Oligonucleotide primers used for generating VWF fragment coding DNA constructs

| Primer name | Primer sequence (5'-3') |
| --- | --- |
| VWF 1099C S | GGGGACTGCGCCTGCTTCTGCGACACC (SEQ ID NO 45) |
| VWF 1099C AS | GGTGTCGCAGAAGCAGGCGCAGTCCCC (SEQ ID NO 46) |
| VWF 1142C S | GAACGGGTATGAGTGTGAGTGGCGCTATA (SEQ ID NO 47) |
| VWF 1142C AS | TATAGCGCCACTCACACTCATACCCGTTC (SEQ ID NO 48) |
| 2764pJSV348F | GCGCTAGCTGAGGACCAAGTAGATCCGCGGCTCATTGATGGG (SEQ ID NO 49) |
| 1202pJSV348R | GGGCCAGAGCAAGCAGCACCCCGGCAAATCTGGCAGG (SEQ ID NO 50) |
| 221#796F | CCTGCCAGATTTGCCGGGGTGCTGCTTGCTCTGGCCC (SEQ ID NO 51) |
| 3537#796R | TACTTGGTCCTCAGCTAGCGCCTGGGGGCACAATGTGGCCGTCCTCC (SEQ ID NO 52) |
| 3747#796R | TACTTGGTCCTCAGCTAGCGCCACTGGACAGTCTTCAGGGTCAACGC (SEQ ID NO 53) |
| 2420pJSV348R | GGCTCAGGGTGCTGACACGTGACTTGACAGGCAGGTGC (SEQ ID NO 54) |
| 3666#796F | GCACCTGCCTGTCAAGTCACGTGTCAGCACCCTGAGCC (SEQ ID NO 55) |
| 5203#796R | TACTTGGTCCTCAGCTAGCGCTGCAGGGGAGAGGGTGGGGATCTGC (SEQ ID NO 56) |

Example 33

VWF Fragments Inhibit FVIII Uptake by Human Dendritic Cells.

Human monocyte-derived dendritic cells were prepared as described in example 28. Expression of the dendritic cell markers CD209 and CD86 were controlled by flow cytometry using a LRS Fortessa instrument (BD). Fluorescent labelled FVIII (Oregon green-FVIII, 30 nM final concentration) was premixed with different concentrations of plasma-derived VWF or VWF fragments before incubating 1 h at 37° C. with dendritic cells. Live/Dead cell kit (Invitrogen #L10119, APC-Cy7) was used for gating on live dendritic cells, and FVIII uptake within this cell population was quantified. Data was normalized for each individual experiment. The signal in samples without VWF was defined as 100% FVIII uptake, and the signal in the sample with the highest concentration of plasma-derived VWF (240 nM based on monomer content) was defined as 0%. Values from 3-5 experiments were combined and IC50 values calculated using non-linear regression in Prism software (log(inhibitor) vs. response—Variable slope (four parameters)). The resulting IC50 values are shown in table 12. The data show that all tested VWF fragments were able to inhibit FVIII uptake by the dendritic cells provided sufficiently high concentrations are used. As FVIII uptake by antigen-presenting cells is the initial step in presenting FVIII to the immune system the data suggests that co-formulation of FVIII with sufficiently high concentration of VWF fragment may have a potential in reducing immunogenicity of FVIII.

TABLE 12

Effect of plasma derived VWF and VWF fragments on FVIII uptake in dendritic cells.

| Domain/comment | VWF fragment sequence | IC50 (nM)* |
|---|---|---|
| TIL'/E'/VWD3 | VWF(764-1041)-ALA-HPC4 monomer | 570 (400-820) |
| TIL'/E'/D3 | VWF(764-1250)-C1099/1142S-ALA-HPC4 monomer | 31 (25-39) |
| TIL'E'/D3/A1 monomer | VWF(764-1464)-C1099/1142S-HPC4 monomer | 31 (18-52) |
| TIL'E'/D3/A1 dimer | VWF(764-1464)-HPC4 dimer** | 16 (11-22) |
| Plasma-derived VWF | VWF (764-2813) | 9.8 (7.6-13) |

*Best fit value and 95% confidence intervals of data from 3-5 experiments
**IC50 value based on molar concentration of the dimer, i.e. multiply IC50 with 2 to reflect IC50 value based on content of VWF monomer fragment.

Example 34

Effect of s.c. FVIII±VWF Fragments in Animals with Inhibiting Antibodies Against FVIII.

The objective is to evaluate the potential of pharmaceutical compositions to treat haemophilia A patients with inhibitors against FVIII. We dose FVIII alone or co-formulated with VWF-fragments subcutaneously to naïve FVIII-KO mice or FVIII-KO mice where inhibitors are induced by repeated subcutaneous or intravenous administrations of FVIII prior to treatment with the compositions, or by injecting a polyclonal or monoclonal anti-FVIII antibody. The effect of the treatments is evaluated in anaesthetized mice after transection of a lateral tail vein. The tail is placed in pre-warmed saline at 37° C. and the bleeding is observed for 60 minutes. The blood loss during the experiment is a measure of the effect of the composition.

Example 35

Administration of VWF Fragments to VWF Knockout Mice:

Test Compound:

Murine VWF Fragment TIL'/E'/D3/A1 1.829 nmol/ml, 0.015 mg/ml

The test compound was formulated in 20 mM imidazol 150 mM NaCl, 0.02% Tween 80, 1.1M Glycerol, 10 mM CaCl2, pH 7.3

6 VWF knockout mice, with an approximate weight of 25 g were dosed intravenously in the tail with 9.48 nmol/kg Murine VWF fragment TIL'/E'/D3/A1.

Blood was sampled pre-dose and at 0.08, 0.33, 0.5, 1, 2, 4, 7, 18 and 24 h post administration in a sparse sample design with 2 mice sampled per time point. The mice were anaesthetized by Isoflurane/02/N20 prior to blood sampling via the retroorbital plexus. Three samples were taken from each mouse. Blood (45 µl) was stabilised with 5 µl of sodium-citrate (0.13 M) and added 200 µl FVIII coatest SP buffer (50 mM TRIS-HCl, 1% BSA, Ciprofloxacin 10 mg/L, pH 7.3). After centrifugation at 4000 g for 5 minutes at room temperature, the supernatants were immediately frozen on dry ice before storage at −80° C. prior to analysis.

Samples were analysed with regards to FVIII concentration in an antigen LOCI assay (Luminescence oxygen channeling immunoassay).

Mean plasma concentration versus time data were analysed relatively to the predose values.

The relative mean FVIII concentration in time after dosing is shown in table 13

TABLE 13

Effect of Murine D'D3A1 IV on FVIII blood concentration in VWF KO mice.

| Time (h) | FVIII increase (% of predose) |
|---|---|
| 0.08 | 174 |
| 0.33 | 190 |
| 0.5 | 176 |
| 1 | 163 |
| 2 | 274 |
| 4 | 250 |
| 7 | 330 |
| 18 | 225 |
| 24 | 207 |

FVIII concentration increased gradually in time after dosing of VWF fragment intravenously with a Tmax after 7

Example 36

Interaction Mapping by HX-MS of vWF Fragments TIL'/E'/D3/A1, TIL'/E'/D3, TIL'E, and TIL'/E'/VWD3 on Turoctocog Alfa (FVIII) and Turoctocog Alfa (FVIII) on vWF Fragment TIL'/E'/D3/A1

Introduction to HX-MS

The HX-MS technology exploits that hydrogen exchange (HX) of a protein can readily be followed by mass spectrometry (MS). By replacing the aqueous solvent containing hydrogen with aqueous solvent containing deuterium, incorporation of a deuterium atom at a given site in a protein will give rise to an increase in mass of 1 Da. This mass increase can be monitored as a function of time by mass spectrometry in quenched samples of the exchange reaction. The deuterium labelling information can be sub-localized to regions in the protein by pepsin digestion under quench conditions and following the mass increase of the resulting peptides.

One use of HX-MS is to probe for sites involved in molecular interactions by identifying regions of reduced hydrogen exchange upon protein-protein complex formation. Usually, binding interfaces will be revealed by marked reductions in hydrogen exchange due to steric exclusion of solvent. Protein-protein complex formation may be detected by HX-MS simply by measuring the total amount of deuterium incorporated in either protein members in the presence and absence of the respective binding partner as a function of time. The HX-MS technique uses the native components, i.e., protein and antibody or Fab fragment, and is performed in solution. Thus HX-MS provides the possibility for mimicking the in vivo conditions (for a recent review on the HX-MS technology, see Wales and Engen, Mass Spectrom. Rev. 25, 158 (2006)).

Materials

Protein batches used were:

FVIII protein batches used were:

FVIII (N8, Turoctocog alfa, SEQ ID NO 2) Batch 0155-0000-0004-37A vWF Fragments

D'D3A1 (SEQ ID NO 19; Cys1099Ser; Cys1142Ser) Batch 0129-0000-0170-6B; 2304 (SEQ ID NO 5) Batch 0129-0000-2304-1B; 2307 (SEQ ID NO 8) Batch 0129-0000-2307-1B; 2308 (SEQ ID NO 11) Batch 0129-0000-2308 2B.

All proteins were buffer exchanged into 20 mM Imidazole, 500 mM NaCl, 10 mM CaCl2, adjusted to pH 7.3 before experiments.

Methods: HX-MS Experiments

Instrumentation and Data Recording

The HX experiments were performed on a nanoACQUITY UPLC System with HDX Technology (Waters Inc.) coupled to a Synapt G2 mass spectrometer (Waters Inc.). The Waters HDX system contained a Leap robot (H/D-x PAL; Waters Inc.) operated by the LeapShell software (Leap Technologies Inc/Waters Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Waters HDX system furthermore contained a temperature controlled chamber holding the pre- and analytical columns, and the LC tubing and switching valves at 1° C. A separately temperature controlled chamber holds the pepsin column at 25° C. For the inline pepsin digestion, 100 μL quenched sample containing 100 pmol hIL-21 was loaded and passed over a Poroszyme® Immobilized Pepsin Cartridge (2.1×30 mm (Applied Biosystems)) placed at 25° C. using a isocratic flow rate of 100 μL/min (0.1% formic acid:CH$_3$CN 95:5). The resulting peptides were trapped and desalted on a VanGuard pre-column BEH C18 1.7 μm (2.1×5 mm (Waters Inc.)). Subsequently, the valves were switched to place the pre-column in-line with the analytical column, UPLC-BEH C18 1.7 μm (1×100 mm (Waters Inc.)), and the peptides separated using a 8 min gradient of 8-45% B delivered at 120 μl/min from the nanoAQUITY UPLC system (Waters Inc.). The mobile phases consisted of A: 0.1% formic acid and B: 0.1% formic acid in CH$_3$CN. The ESI MS data and the separate elevated energy (MS$^E$) experiments were acquired in positive ion mode using a Synapt G2 mass spectrometer (Waters Inc.). Leucine-enkephalin was used as the lock mass ([M+H]$^+$ ion at m/z 556.2771) and data was collected in continuum mode (For further description, see Andersen and Faber, Int. J. Mass Spec., 302, 139-148 (2011)).

Data Analysis

Peptic peptides were identified in separate experiments using standard MS$^E$ methods where the peptides and fragments are further aligned utilizing the ion mobility properties of the Synapt G2 (Waters Inc.). MS$^E$ data were processed using ProteinLynx Global Server version version 2.5 (Waters Inc.). The HX-MS raw data files were processed in the DynamX software (Waters Inc.). DynamX automatically performs the lock mass-correction and deuterium incorporation determination, i.e., centroid determination of deuterated peptides. Furthermore, all peptides were inspected manually to ensure correct peak and deuteration assignment by the software.

Epitope Mapping Experiment

Amide hydrogen/deuterium exchange (HX) was initiated by a 10-fold dilution of FVIII in the presence or absence of vWF fragment, i.e., D'D3A1, 2308, 2307, or –2304 at time 0 into 20 mM Imidazole, 150 mM NaCl, 10 mM CaCl2, pH 7.3 (uncorrected value) at later time points into the corresponding deuterated buffer (i.e. 20 mM Imidazole, 150 mM NaCl, 10 mM CaCl2 prepared in D$_2$O, 98% D$_2$O final, pH 7.3 (uncorrected value)). All HX reactions were carried out at 20° C. and contained 3 μM FVIII in the absence or presence of 4.5 μM vWF fragment thus giving a 1.5 fold molar excess of vWF fragment binding partner. At appropriate time intervals ranging from 10 sec to 240 sec, 50 μl aliquots of the HX reaction were quenched by 50 μl ice-cold quenching buffer (1.36 M TCEP, 2 M urea) resulting in a final pH of 2.5 (uncorrected value).

Results and Discussion

Interaction Mapping of 2304 and 2307 on FVIII

The HX time-course of 191 peptides, covering 83% of the primary sequence of FVIII were monitored in the absence or presence of the vWF fragments 2304 or 2307 for i.e., 10, 20, 30, 40, 60, 120, and 240 sec.

The vWF fragments 2304 and 2307 both induce identical alterations in the exchange profile of FVIII and will be described together here. The observed exchange pattern in the time points (i.e., 10, 20, 30, 40, 60, 120, and 240 sec) in the presence or absence of 2304/2307 can be divided into different groups: One group of peptides display an exchange pattern that is unaffected by the binding of 2304/2307. In contrast, another group of peptides in FVIII show protection from exchange upon 2304/2307 binding.

The regions displaying protection upon 2304/2307 binding encompass peptides covering residues 1855-1875, 1857-1875, 2062-2070, 2125-2147, 2125-2148, 2127-2147, 2275-2291, 2275-2302, 2275-2305, 2292-2305, and 2293-2312 (Table 14). However, by comparing the relative amounts of exchange protection within each peptide upon binding 2304/2307 and the lack of epitope effects in overlapping and adjacent peptides in these regions, the regions that display reduced deuterium incorporation can be narrowed to residues 1862-1875, 2062-2070, 2125-2147, and 2285-2299.

Interaction Mapping of D'D3A1 and 2308 on FVIII

The HX time-course of 185 peptides, covering 79% of the primary sequence of FVIII were monitored in the absence or presence of the vWF fragments D'D3A1 or 2308 for 10, 20, 30, 40, 60, 120, and 240 sec.

The vWF fragments D'D3A1 and 2308 both induce identical alterations in the exchange profile of FVIII and will be described together here.

The regions displaying protection upon D'D3A1 or 2308 binding encompass peptides covering residues 1669-1680, 1738-1765, 1743-1765, 1856-1869, 1870-1874, 2061-2074, 2063-2074, 2123-2146, and 2260-2280 (Table 15).

However, by comparing the relative amounts of exchange protection within each peptide upon binding of D'D3A1 or 2308 and the lack of epitope effects in overlapping and adjacent peptides in these regions, the regions that display reduced deuterium incorporation can be narrowed to residues 1671-1680, 1745-1754, 1858-1874, 2063-2074, 2125-2146, 2262-2280.

Interaction Mapping of FVIII on D'D3A1

The HX time-course of 82 peptides, covering 58% of the primary sequence of vWF fragment D'D3A1 were monitored in the absence or presence of FVIII for 10, 20, 40, 60, 120, and 240 sec.

The region displaying exchange protection upon FVIII binding encompass the peptide covering residues 768-778 (Table 16).

However, by comparing the relative amounts of exchange protection within each peptide upon binding FVIII and the lack of epitope effects in overlapping and adjacent peptides in these regions, the regions that display reduced deuterium incorporation can be narrowed to residues 770-778.

Conclusion

Upon binding of either 2304 or 2307 all regions of FVIII showed similar responses. The same group of peptides were affected by vWF fragment binding in the early time-points.

Furthermore, these affected regions identified for 2304/2307 binding were found to show overlap with affected regions upon binding to D'D3A1/2308 within domain A3 and C1 of FVIII.

Due to lacking sequence coverage of the peptic peptide map conducted to the HX-MS time course of 2304/2307 binding it was not possible to exchange characteristics for residues 1671-1680. Thus it was not possible to verify if 2304/2307 binding induces exchange protection to this region as it was identified upon D'D3A1/2308 binding.

Upon binding of FVIII the regions covering residues 770-778 of D'D3A1 showed exchange protection. The obtained sequence coverage of 58% of D'D3A1 afforded by the peptic peptides conducted to HXMS analysis of FVIII binding, does not allow to leave out that more interaction site are present within D'D3A1/2308.

Conclusion

The identified regions of FVIII showing protection upon binding to vWF fragments D'D3A1, 2308, 2304, or 2307 are structurally situated at remote distances when mapping on to the crystal structure PDB: 2R7E. This makes it highly unlikely that they can all be assigned to protection induced by binding interface between FVIII and the vWF fragments D'D3A1, 2308, 2304, or 2307. The HX-MS analysis is unable to distinguish between exchange protection induced by binding interface with exchange protections induced by rapid conformational changes.

Thus it is plausible that the observed regions showing exchange protection upon binding to vWF fragments D'D3A1, 2308, 2304, or 2307 are induced by both binding interface and conformational changes of FVIII.

The HXMS study of FVIII binding to vWF fragments D'D3A1, 2308, 2304, or 2307 revealed overlapping regions within domains A3 and C1, and therefore the complex binding to this part of FVIII is identical for the vWF fragments investigated.

The observed discrepancy in domain C2 hints that this part of FVIII undergoes conformational changes upon complex formation with the vWF-fragments. Furthermore, the obtained results hint that the truncation differences between D'D3A1/2308 and 2304/2307 induces different conformational changes of domain C2. In contrast the truncation difference between 2304 and 2307 does not seem to affect the conformational orientation of C2, since identical exchange profiles of domain C2 were observed for binding to these vWF-fragment species.

It is well known that the domains C1 and C2 are essential for the membrane binding affinity of FVIII. It can be speculated that conformational changes of these part of FVIII will reduce the membrane binding ability of FVIII. The conformational position of domains C1 and C2 of FVIII complex bound to the vWF fragments might be unfavourable for membrane binding affinity of FVIII. Furthermore, it is highly likely that the fragments in complex with FVIII will shield for the membrane binding affinity of FVIII as it has been established for the membrane binding characteristics of FVIII complex bound to endogenous vWF. A reduced membrane binding affinity of FVIII complex bound to the vWF fragments in comparison to free FVIII would lead to a reduced binding of FVIII to cell membranes of the immune system, e.g. antigen presenting cells. This could decrease presentation of FVIII-derived peptides on MHC class II and it can therefore be speculated that FVIII complex bound to vWF fragments will be less immunogenic than free FVIII.

TABLE 14

HXMS analysis of FVIII (Turoctocog alfa; seq. no. using wt FVIII) (SEQ ID 2) binding to the vWF fragments 2304 (SEQ ID 5) or 2307 (SEQ ID 8). After deuterium exchange reaction. FVIII is digested with pepsin yielding the present peptic peptides identified to show exchange protection in the presence of 2304 or 2307.

| Sequence | Domain | 2304 | 2307 |
| --- | --- | --- | --- |
| L1855-E1875 | A3 | EX | EX |
| V1857-E1875 | A3 | EX | EX |
| W2062-W2070 | A3 | EX | EX |
| V2125-R2147 | C1 | EX | EX |
| V2125-Y2148 | C1 | EX | EX |
| F2127-R2147 | C1 | EX | EX |
| F2275-T2291 | C2 | EX | EX |
| F2275-L2302 | C2 | EX | EX |
| F2275-Y2305 | C2 | EX | EX |
| P2292-Y2305 | C2 | EX | EX |
| V2293-S2312 | C2 | EX | EX |

EX: exchange protection of FVIII residues upon 2304 or 2307 binding indicating interaction region (40 sec incubation in D2O, >0.4 Da).

TABLE 15

HXMS analysis of FVIII (Turoctocog alfa; seq. no. using wt FVIII) (SEQ ID 2) binding to the vWF fragments D'D3A1 (SEQ ID 19; Cys1099Ser; Cys1142Ser) or 2308 (SEQ ID 11; Cys1099Ser; Cys1142Ser). After deuterium exchange reaction. FVIII is digested with pepsin yielding the present peptic peptides identified to show exchange protection in the presence of D'D3A1 or 2308.

| Sequence | Domain | D'D3A1 | 2308 |
|---|---|---|---|
| S1669-Y1680 | a3 | EX | EX |
| F1738-E1765 | A3 | EX | EX |
| F1743-E1765 | A3 | EX | EX |
| L1856-R1869 | A3 | EX | EX |
| Q1870-Q1874 | A3 | EX | EX |
| A2061-D2074 | C1 | EX | EX |
| S2063-D2074 | C1 | EX | EX |
| L2123-A2146 | C1 | EX | EX |
| F2260-V2280 | C2 | EX | EX |

EX: exchange protection of FVIII residues upon D'D3A1 or 2308 binding indicating interaction region (40 sec incubation in D2O, >0.4 Da).

TABLE 16

HXMS analysis of vWF fragment D'D3A1 (SEQ ID 19; Cys1099Ser; Cys1142Ser) binding to the FVIII (Turoctocog alfa (SEQ ID 2). After deuterium exchange reaction. D'D3A1 is digested with pepsin yielding the present peptic peptide identified to show exchange protection in the presence of FVIII.

| Sequence | Domain | FVIII |
|---|---|---|
| R768-A778 | D' | EX |

EX: exchange protection of D'D3A1 residues upon FVIII binding indicating interaction region (40 sec incubation in D2O, >0.4 Da).

Example 37

Complex Formation of FVIII (SEQ ID 2) with TIL'/E'/D3/A1 III (SEQ ID 19; Cys1099Ser; Cys1142Ser) and of FVIII (SEQ ID 2) with TIL'/E'/D3 II (SEQ ID 14; Cys1099Ser; Cys1142Ser) Analysed by SEC-UV.

Materials

Protein Batches Used were:

FVIII Protein Batches Used were:

FVIII (N8, Turoctocog alfa, SEQ ID NO 2) Batch 0155-0000-0004-37A; TIL'/E'/D3/A1 III (SEQ ID NO 19; Cys1099Ser; Cys1142Ser) Batch 0129-0000-0170-6B; TIL'/E'/D3 II (SEQ ID 14; Cys1099Ser; Cys1142Ser) Batch 0129-0000-2309-1B.

Methods

Size-exclusion chromatography was performed on a Waters Biosuite 4.6×300 mm column using a flow rate of 0.3 ml/min and a running buffer of 155 mM NaCl, 10 mM Calciumacetat, 10% Isopropanol at 25° C. The absorbance of the effluent was monitored by a UV detector at 280 nm. SEC-UV characterization were performed of FVIII, TIL'/E'/D3/A1 III, TIL'/E'/D3 II, and 1:2 complexes of FVIII—TIL'/E'/D3/A1 III and of FVIII—TIL'/E'/D3 II. Samples of FVIII 10 µM, TIL'/E'/D3/A1 III 20 µM, TIL'/E'/D3 II 20 µM, and in complex were prepared and 15 µL were loaded on to the column.

Results and Conclusion

SEC-UV of the mixtures of FVIII—TIL'/E'/D3/A1 III and FVIII—TIL'/E'/D3 II showed significant fractions of the complex to elute intact from the column. The complex would be expected to elute a little earlier than FVIII; this was also observed in both cases.

Example 38

Preparation of Dimer Form of VWF Fragment: 764-1242 (SEQ ID NO 57) and 764-1482 (SEQ ID NO 58)

In the native full length VWF molecule (SEQ ID NO 22) two cysteine residues in the N-terminal part of the molecule are supposed to participate in the dimerization/multimerization of VWF: Cys1099 and Cys1142.

In some cases, a dimeric form of the VWF fragments is wanted. This can be accomplished in several ways:

One method to accomplish dimer formation is to keep the two residues at position 1099 and position 1142 as cysteines. In order to make a recombinant dimeric molecule, the cDNA encoding the desired VWF fragment is including the pre-sequence of VWF e.g. the D1D2 sequence of VWF (amino acid residues 23-763 of SEQ ID NO 22). This will, during synthesis in the golgi apparatus align two monomers of a given VWF fragment in a configuration allowing a dimeric molecule to be formed with two disulphide bonds in which Cys1099 in monomer 1 is connected to a Cys1099 in monomer 2 and Cys1142 in monomer 1 is connected to Cys1142 in monomer 2. The pre-sequence is cleaved of during secretion of the dimeric VWF protein.

Another method to accomplish dimer formation is to avoid the inclusion of the pre-sequence (amino acid residues 23-763 of SEQ ID NO 22) and simply let a recombinant VWF fragment with Cys in position 1099 and 1142 form a dimeric molecule. This can in principle result in a series of different dimers e.g.:

Cys1099-Cys1099/Cys1142-Cys1142 (two disulphide bonds—like above)

Cys1099-Cys1142/Cys1099-Cys1142 (two disulphide bonds)

Cys1099-Cys1099 (one disulphide bond)

Cys1142-Cys1142 (one disulphide bond)

Cys1099-Cys1142 (one disulphide bond)

Yet another method to accomplish dimer formation is to replace one of the cysteine residues 1099 or 1142 with other amino acid residues (e.g. Serine, Arginine).

If Cys1099 is replaced with a non-Cysteine residue, the molecule can form a dimer by establishment of a disulphide bond between Cys1142 in monomer 1 with Cys1142 in monomer 2.

If Cys1142 is replaced with a non-Cysteine residue, the molecule can form a dimer by establishment of a disulphide bond between Cys1099 in monomer 1 with Cys1099 in monomer 2.

The dimeric forms mentioned above are constructed either with or without the D1D2 pre-sequence of VWF (amino acid residues 23-763 of SEQ ID NO 22).

The different monomeric and dimeric forms will have different properties with regards to their binding to FVIII, their ease of production and their effect on bioavailability of FVIII when injected subcutaneously as a co-formulation.

Example 39

Purification and Characterisation of HPC4-Tagged VWF Fragments

Some VWF fragments are cloned and expressed with a C-terminal HPC4 tag: EDQVDPRLIDGK (SEQ ID NO 38). Sometimes an additional linker with the sequence of ALA is introduced between the VWF fragment and the HPC4 tag. After cloning, expression and cell culturing the cell media is added $CaCl_2$ to a final concentration of 1 mM. The media is passed over an anti-HPC4 column. The column is equilibrated with 20 mM HEPES, 100 mM NaCl, 1 mM $CaCl_2$, pH=7.5. After application of the cell media, the column is washed with 20 mM HEPES, 1M NaCl, 1 mM $CaCl_2$, pH=7.5 and the HPC4-tagged VWF fragment is subsequently eluted with 20 mM HEPES, 100 mM NaCl, 5 mM EDTA, pH=7.5. The pool from the anti-HPC4 column is added 3 volumes of water to reduce the conductivity and applied onto a Mono Q column. Prior to the application the Mono Q column is equilibrated with 20 mM HEPES, 100 mM NaCl, 5 mM EDTA, pH=7.5. The Mono Q column is washed with 20 mM HEPES, 100 mM NaCl, pH=7.5 and the VWF fragment is eluted with a gradient from 100 mM NaCl to 2M NaCl in 20 mM HEPES, 10 mM $CaCl_2$, pH=7.5.

The purified protein is characterised by 1) SDS-gel electrophoreses, 2) analytical HPLC and 3) amino acid sequence analysis.

Example 40

Purification and Characterisation of Non HPC4-Tagged VWF Fragment

After cloning, expression and cell culturing the cell media is passed over an anti-VWF-Sepharose column. This column consists of an antibody against the N-terminal part of VWF coupled to Sepharose. The antibody is characterised by binding to the VWF fragment at neutral pH but not binding the VWF fragment at week acid pH. This allow the VWF fragment to be bound when passing cell culture media over the column at neutral pH. Hereafter the column is washed with a buffer at neutral pH where after the VWF fragment is eluted from the column with a buffer at a week acid pH (e.g. pH in the range from 3.0 to 6.5). The eluted VWF fragment is further purified by a combination classical purification steps such as ion-exchange chromatography, hydrophobic interaction chromatography and gelfiltration.

The purified VWF fragment is characterised by 1) SDS-gel electrophoreses, 2) analytical HPLC and 3) amino acid sequence analysis.

Example 41

Bioavailability of a FVIII after Subcutaneous (s.c.) Administration Co-Formulated with VWF Fragment A FVIII compound e.g. GlycoPEGylated FVIII, i.e. "N8-GP" (prepared essentially as disclosed in example 1+2 in WO2009108806) or another conjugated or non-conjugated FVIII at 2000 IU/ml or 1.2 µM is co-formulated with VWF fragment 764-1242 or 764-1482 at a concentration that enables the majority of FVIII to be bound to a VWF fragment compound in the injection composition. The binding of the VWF fragment to FVIII and the % saturation of the FVIII can be determined from the concentration of FVIII and VWF fragment in the composition and from experiments evaluating the binding affinity of the VWF fragment to the FVIII compound such as e.g. surface plasmon resonance experiments.

Test compounds are formulated in 18 mg/ml NaCl, 3 mg/ml saccharose, 1.5 mg/ml L-histidine, 0.1 mg/ml polysorbate 80, 0.25 mg/ml $CaCl_2$, pH 7.3. FVIII KO mice, exon 16 knock-out in a mixed background of C57Bl/6 and SV129, bred at Taconic M&B (B6.129S4-F8tm1Kaz/J) with an approximate weight of 22 g are dosed subcutaneously in the flank with 10000 U/kg FVIII or FVIII/VWF, 6 mice per test compound. Blood are sampled at 1, 3, 7, 17, 24, 30, 48, 72 and 96 h post administration. The mice are anaesthetized by isoflurane/$O_2$/$N_2O$ prior to blood sampling via the retroorbital plexus. Three samples are taken from each mouse. Blood (45 µl) are stabilised with 5 µl of sodium-citrate (0.13 M) and added 200 µl FVIII Coatest SP buffer (50 mM TRIS-HCl, 1% BSA, Ciprofloxacin 10 mg/L, pH 7.3). After centrifugation at 4000 g for 5 minutes at room temperature are supernatants immediately frozen on dry ice before storage at −80° C. prior to analysis. FVIII activity is measured in a chromogenic assay as described by Øvlisen K et al. J. Thromb. Haemost, 2008, 6: 969-975 and FVIII antigen is analysed using two FVIII light chain antibodies (4F45 and 4F11) in a FVIII LOCI assay (Luminescence oxygen channelling immunoassay).

Mean plasma concentration versus time data are analysed by non-compartmental analysis using WinNonlin Phoenix (Pharsight Corporation) estimating the given pharmacokinetic parameters. The bioavailability is estimated by comparing the AUC/dose after s.c. administration with AUC/dose after i.v. administration of the FVIII compound in FVIII KO mice.

Example 42

Immunogenicity of VWF Fragments

The immunogenicity of VWF fragment 764-1242 or 764-1482 relative to other VWF fragments and full-length VWF is evaluated in a species capable of ADAM28-mediated cleavage of VWF, e.g. mice.

ADAM28 (A Disintegrin And Metalloproteinase Domain 28) has been described to cleave VWF (Mochizuki et al. J Natl Cancer Inst 2012; 104: 906-922) and is according to GeneCard® expressed on lymphocytes.

The relative immunogenicity is evaluated from the titer of VWF binding antibodies at certain time points after administration of VWF fragment 764-1242 or 764-1482 and comparator VWF fragments, e.g. VWF 764-1464 or full-length VWF. The assay for detection of VWF binding antibodies is a radioimmunoassay (RIA). Briefly, anti-VWF antibodies from a sample bind to radioactive $^{125}$I-labelled VWF (full-length or fragments). Immunoglobulin and immune complexes bind to protein G-sepharose and is precipitated by centrifugation. The radioactivity in the precipitate is measured and this is proportional to the amount of anti-VWF antibodies in the sample. The result is expressed in percent of the total amount of added radioactivity. i.e. as % bound/total (% B/T).

The appearance of anti-VWF antibodies is evaluated after repeated (e.g. once weekly for 4 weeks or once daily for three weeks) s.c. or i.v. administration of the compounds in naïve mice, in VWF k/o mice as well as in mice tolerized to human VWF. Mice are injected weekly for e.g. eight weeks s.c. or i.v. with e.g. 1 µg VWF or the corresponding molar concentration (based on monomer content) of VWF fragments. The readout is the ratio of animals with positive titres at certain time points after the first and/or the last administration (e.g. 1, 2, 3, 4, 5, 6, 7 or 8 weeks). VWF k/o mice are injected weekly e.g. with VWF fragment or full-length VWF. For daily s.c. administration, the VWF dose is lower and based upon the bioavailability of the VWF fragment. Mice tolerized to hVWF are injected weekly for e.g. eight weeks s.c. with e.g. 1 µg VWF (or the corresponding molar concentration (based on monomer content) of VWF fragments). In some experiments the VWF is combined with complete Freund's adjuvant (CFA) for the first injection followed by weekly challenges by incomplete Freund's adjuvant (IFA).

Example 43

FVIII Degradation: Determination of FVIII Free Light Chain by Size-Exclusion Chromatography (SEC)

The dissociation of the rFVIII compound into free heavy and light chains is evaluated by a SEC method. The column is Sepax Zenix™ SEC-300 and the eluent is 10 mM Tris, 10 mM CaCl$_2$, 300 mM NaCl and 5% isopropanol, pH 7.0 Degradation of Factor VIII molecules is observed in SEC as appearance of a peak with longer elution times than monomeric Factor VIII. This peak has been assigned to free Light Chain (free LC).

Example 44

Stabilising Effect of vWF on Liquid FVIII Stability.

Formulations of Glycopegylated B-domain truncated/deleted FVIII ("GP-BDD-FVIII") with and without a vWF fragment were prepared. The vWF fragment was VWF(764-1464)—C1099/1142S (SEQ ID NO 19), with a C-terminal HPC4-tag added to facilitate purification. Both formulations contained about 0.85 µM GP-BDD-FVIII, 190 mM NaCl, 1.8 mM CaCl$_2$, 0.03 mg/ml polysorbate 80, 0.07 mg/ml Methionine, 10 mM sucrose, 12 mM Histidine and had a pH close to 6.9. One of the formulations furthermore contained 1.2 µM of a vWF fragment. The two samples were incubated for 4 weeks at 5° C. and assayed for free Light Chain by SEC chromatopgraphy. In order to test for the influence of the vWF on the chromatopgraphy of GP-BDD-FVIII, the samples without vWF fragment was split in two after the 4 weeks of incubation, and one of the resulting samples had vWF fragment added to a final concentration of 1.2 µM just prior to analysis. The amount of free Light Chain measured in the different samples is shown in the following table:

TABLE 17

| GP-BDD-FVIII concentration | vWF fragment concentration during incubation | vWF fragment added just before SEC analysis | % free Light Chain after 4 weeks at 5° C. |
|---|---|---|---|
| 0.85 µM | 1.2 µM | — | 1.1% |
| 0.85 µM | — | — | 5.1% |
| 0.85 µM | — | 1.2 µM | 4.5% |

It is seen that much less free Light Chain is observed after incubation with the vWF fragment. Addition of vWF just prior to analysis does not affect the result much, which shows that the effect is not a chromatographic artefact, but results from a stabilising action of the vWF fragment on GP-BDD-FVIII.

SEQUENCE LISTING

```
<160> NUMBER OF SEQ ID NOS: 58

<210> SEQ ID NO 1
<211> LENGTH: 2332
<212> TYPE: PRT
<213> ORGANISM: Homo sapiens

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205
```

```
His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
610                 615                 620
```

```
Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
            1010                1015                1020

Asn Ser Pro Ser Val Trp Gln Asn Ile Leu Glu Ser Asp Thr Glu
            1025                1030                1035

Phe Lys Lys Val Thr Pro Leu Ile His Asp Arg Met Leu Met Asp
```

-continued

```
                1040                1045                1050
Lys Asn Ala Thr Ala Leu Arg Leu Asn His Met Ser Asn Lys Thr
        1055                1060                1065
Thr Ser Ser Lys Asn Met Glu Met Val Gln Gln Lys Lys Glu Gly
        1070                1075                1080
Pro Ile Pro Pro Asp Ala Gln Asn Pro Asp Met Ser Phe Phe Lys
        1085                1090                1095
Met Leu Phe Leu Pro Glu Ser Ala Arg Trp Ile Gln Arg Thr His
        1100                1105                1110
Gly Lys Asn Ser Leu Asn Ser Gly Gln Gly Pro Ser Pro Lys Gln
        1115                1120                1125
Leu Val Ser Leu Gly Pro Glu Lys Ser Val Glu Gly Gln Asn Phe
        1130                1135                1140
Leu Ser Glu Lys Asn Lys Val Val Val Gly Lys Gly Glu Phe Thr
        1145                1150                1155
Lys Asp Val Gly Leu Lys Glu Met Val Phe Pro Ser Ser Arg Asn
        1160                1165                1170
Leu Phe Leu Thr Asn Leu Asp Asn Leu His Glu Asn Asn Thr His
        1175                1180                1185
Asn Gln Glu Lys Lys Ile Gln Glu Glu Ile Glu Lys Lys Glu Thr
        1190                1195                1200
Leu Ile Gln Glu Asn Val Val Leu Pro Gln Ile His Thr Val Thr
        1205                1210                1215
Gly Thr Lys Asn Phe Met Lys Asn Leu Phe Leu Leu Ser Thr Arg
        1220                1225                1230
Gln Asn Val Glu Gly Ser Tyr Asp Gly Ala Tyr Ala Pro Val Leu
        1235                1240                1245
Gln Asp Phe Arg Ser Leu Asn Asp Ser Thr Asn Arg Thr Lys Lys
        1250                1255                1260
His Thr Ala His Phe Ser Lys Lys Gly Glu Glu Glu Asn Leu Glu
        1265                1270                1275
Gly Leu Gly Asn Gln Thr Lys Gln Ile Val Glu Lys Tyr Ala Cys
        1280                1285                1290
Thr Thr Arg Ile Ser Pro Asn Thr Ser Gln Gln Asn Phe Val Thr
        1295                1300                1305
Gln Arg Ser Lys Arg Ala Leu Lys Gln Phe Arg Leu Pro Leu Glu
        1310                1315                1320
Glu Thr Glu Leu Glu Lys Arg Ile Ile Val Asp Asp Thr Ser Thr
        1325                1330                1335
Gln Trp Ser Lys Asn Met Lys His Leu Thr Pro Ser Thr Leu Thr
        1340                1345                1350
Gln Ile Asp Tyr Asn Glu Lys Glu Lys Gly Ala Ile Thr Gln Ser
        1355                1360                1365
Pro Leu Ser Asp Cys Leu Thr Arg Ser His Ser Ile Pro Gln Ala
        1370                1375                1380
Asn Arg Ser Pro Leu Pro Ile Ala Lys Val Ser Ser Phe Pro Ser
        1385                1390                1395
Ile Arg Pro Ile Tyr Leu Thr Arg Val Leu Phe Gln Asp Asn Ser
        1400                1405                1410
Ser His Leu Pro Ala Ala Ser Tyr Arg Lys Lys Asp Ser Gly Val
        1415                1420                1425
Gln Glu Ser Ser His Phe Leu Gln Gly Ala Lys Lys Asn Asn Leu
        1430                1435                1440
```

```
Ser Leu Ala Ile Leu Thr Leu Glu Met Thr Gly Asp Gln Arg Glu
    1445            1450                1455

Val Gly Ser Leu Gly Thr Ser Ala Thr Asn Ser Val Thr Tyr Lys
    1460            1465                1470

Lys Val Glu Asn Thr Val Leu Pro Lys Pro Asp Leu Pro Lys Thr
    1475            1480                1485

Ser Gly Lys Val Glu Leu Leu Pro Lys Val His Ile Tyr Gln Lys
    1490            1495                1500

Asp Leu Phe Pro Thr Glu Thr Ser Asn Gly Ser Pro Gly His Leu
    1505            1510                1515

Asp Leu Val Glu Gly Ser Leu Leu Gln Gly Thr Glu Gly Ala Ile
    1520            1525                1530

Lys Trp Asn Glu Ala Asn Arg Pro Gly Lys Val Pro Phe Leu Arg
    1535            1540                1545

Val Ala Thr Glu Ser Ser Ala Lys Thr Pro Ser Lys Leu Leu Asp
    1550            1555                1560

Pro Leu Ala Trp Asp Asn His Tyr Gly Thr Gln Ile Pro Lys Glu
    1565            1570                1575

Glu Trp Lys Ser Gln Glu Lys Ser Pro Glu Lys Thr Ala Phe Lys
    1580            1585                1590

Lys Lys Asp Thr Ile Leu Ser Leu Asn Ala Cys Glu Ser Asn His
    1595            1600                1605

Ala Ile Ala Ala Ile Asn Glu Gly Gln Asn Lys Pro Glu Ile Glu
    1610            1615                1620

Val Thr Trp Ala Lys Gln Gly Arg Thr Glu Arg Leu Cys Ser Gln
    1625            1630                1635

Asn Pro Pro Val Leu Lys Arg His Gln Arg Glu Ile Thr Arg Thr
    1640            1645                1650

Thr Leu Gln Ser Asp Gln Glu Glu Ile Asp Tyr Asp Asp Thr Ile
    1655            1660                1665

Ser Val Glu Met Lys Lys Glu Asp Phe Asp Ile Tyr Asp Glu Asp
    1670            1675                1680

Glu Asn Gln Ser Pro Arg Ser Phe Gln Lys Lys Thr Arg His Tyr
    1685            1690                1695

Phe Ile Ala Ala Val Glu Arg Leu Trp Asp Tyr Gly Met Ser Ser
    1700            1705                1710

Ser Pro His Val Leu Arg Asn Arg Ala Gln Ser Gly Ser Val Pro
    1715            1720                1725

Gln Phe Lys Lys Val Val Phe Gln Glu Phe Thr Asp Gly Ser Phe
    1730            1735                1740

Thr Gln Pro Leu Tyr Arg Gly Glu Leu Asn Glu His Leu Gly Leu
    1745            1750                1755

Leu Gly Pro Tyr Ile Arg Ala Glu Val Glu Asp Asn Ile Met Val
    1760            1765                1770

Thr Phe Arg Asn Gln Ala Ser Arg Pro Tyr Ser Phe Tyr Ser Ser
    1775            1780                1785

Leu Ile Ser Tyr Glu Glu Asp Gln Arg Gln Gly Ala Glu Pro Arg
    1790            1795                1800

Lys Asn Phe Val Lys Pro Asn Glu Thr Lys Thr Tyr Phe Trp Lys
    1805            1810                1815

Val Gln His His Met Ala Pro Thr Lys Asp Glu Phe Asp Cys Lys
    1820            1825                1830
```

```
Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085

Ala Arg Gln Lys Phe Ser Ser Leu Tyr Ile Ser Gln Phe Ile Ile
2090                2095                2100

Met Tyr Ser Leu Asp Gly Lys Lys Trp Gln Thr Tyr Arg Gly Asn
2105                2110                2115

Ser Thr Gly Thr Leu Met Val Phe Phe Gly Asn Val Asp Ser Ser
2120                2125                2130

Gly Ile Lys His Asn Ile Phe Asn Pro Pro Ile Ile Ala Arg Tyr
2135                2140                2145

Ile Arg Leu His Pro Thr His Tyr Ser Ile Arg Ser Thr Leu Arg
2150                2155                2160

Met Glu Leu Met Gly Cys Asp Leu Asn Ser Cys Ser Met Pro Leu
2165                2170                2175

Gly Met Glu Ser Lys Ala Ile Ser Asp Ala Gln Ile Thr Ala Ser
2180                2185                2190

Ser Tyr Phe Thr Asn Met Phe Ala Thr Trp Ser Pro Ser Lys Ala
2195                2200                2205

Arg Leu His Leu Gln Gly Arg Ser Asn Ala Trp Arg Pro Gln Val
2210                2215                2220

Asn Asn Pro Lys Glu Trp Leu Gln Val Asp Phe Gln Lys Thr Met
```

```
                2225                2230                2235

Lys Val Thr Gly Val Thr Gln Gly Val Lys Ser Leu Leu Thr
        2240                2245                2250

Ser Met Tyr Val Lys Glu Phe Leu Ile Ser Ser Gln Asp Gly
        2255                2260                2265

His Gln Trp Thr Leu Phe Phe Gln Asn Gly Lys Val Lys Val Phe
        2270                2275                2280

Gln Gly Asn Gln Asp Ser Phe Thr Pro Val Val Asn Ser Leu Asp
        2285                2290                2295

Pro Pro Leu Leu Thr Arg Tyr Leu Arg Ile His Pro Gln Ser Trp
        2300                2305                2310

Val His Gln Ile Ala Leu Arg Met Glu Val Leu Gly Cys Glu Ala
        2315                2320                2325

Gln Asp Leu Tyr
        2330

<210> SEQ ID NO 2
<211> LENGTH: 21
<212> TYPE: PRT
<213> ORGANISM: Artificial Sequence
<220> FEATURE:
<223> OTHER INFORMATION: Linker sequence

<400> SEQUENCE: 2

Ser Phe Ser Gln Asn Ser Arg His Pro Ser Gln Asn Pro Pro Val Leu
1               5                   10                  15

Lys Arg His Gln Arg
            20

<210> SEQ ID NO 3
<211> LENGTH: 1667
<212> TYPE: PRT
<213> ORGANISM: Artificial Sequence
<220> FEATURE:
<223> OTHER INFORMATION: 226 amino acid B domain FVIII variant

<400> SEQUENCE: 3

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160
```

```
His Val Asp Leu Val Lys Asp Leu Asn Ser Gly Leu Ile Gly Ala Leu
            165                 170                 175
Leu Val Cys Arg Glu Gly Ser Leu Ala Lys Glu Lys Thr Gln Thr Leu
        180                 185                 190
His Lys Phe Ile Leu Leu Phe Ala Val Phe Asp Glu Gly Lys Ser Trp
    195                 200                 205
His Ser Glu Thr Lys Asn Ser Leu Met Gln Asp Arg Asp Ala Ala Ser
210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
        275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
```

```
                    580             585             590
Arg Phe Leu Pro Asn Pro Ala Gly Val Gln Leu Glu Asp Pro Glu Phe
            595             600             605

Gln Ala Ser Asn Ile Met His Ser Ile Asn Gly Tyr Val Phe Asp Ser
610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Phe Ser Gly Tyr
            645             650             655

Thr Phe Lys His Lys Met Val Tyr Glu Asp Thr Leu Thr Leu Phe Pro
            660             665             670

Phe Ser Gly Glu Thr Val Phe Met Ser Met Glu Asn Pro Gly Leu Trp
            675             680             685

Ile Leu Gly Cys His Asn Ser Asp Phe Arg Asn Arg Gly Met Thr Ala
            690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
                725             730             735

Ile Glu Pro Arg Ser Phe Ser Gln Asn Ser Arg His Pro Ser Thr Arg
            740             745             750

Gln Lys Gln Phe Asn Ala Thr Thr Ile Pro Glu Asn Asp Ile Glu Lys
            755             760             765

Thr Asp Pro Trp Phe Ala His Arg Thr Pro Met Pro Lys Ile Gln Asn
            770             775             780

Val Ser Ser Ser Asp Leu Leu Met Leu Leu Arg Gln Ser Pro Thr Pro
785             790             795             800

His Gly Leu Ser Leu Ser Asp Leu Gln Glu Ala Lys Tyr Glu Thr Phe
            805             810             815

Ser Asp Asp Pro Ser Pro Gly Ala Ile Asp Ser Asn Asn Ser Leu Ser
            820             825             830

Glu Met Thr His Phe Arg Pro Gln Leu His His Ser Gly Asp Met Val
            835             840             845

Phe Thr Pro Glu Ser Gly Leu Gln Leu Arg Leu Asn Glu Lys Leu Gly
            850             855             860

Thr Thr Ala Ala Thr Glu Leu Lys Lys Leu Asp Phe Lys Val Ser Ser
865             870             875             880

Thr Ser Asn Asn Leu Ile Ser Thr Ile Pro Ser Asp Asn Leu Ala Ala
                885             890             895

Gly Thr Asp Asn Thr Ser Ser Leu Gly Pro Pro Ser Met Pro Val His
            900             905             910

Tyr Asp Ser Gln Leu Asp Thr Thr Leu Phe Gly Lys Lys Ser Ser Pro
            915             920             925

Leu Thr Glu Ser Gly Gly Pro Leu Ser Leu Ser Glu Glu Asn Asn Asp
930             935             940

Ser Lys Leu Leu Glu Ser Gly Leu Met Asn Ser Gln Glu Ser Ser Trp
945             950             955             960

Gly Lys Asn Val Ser Ser Thr Glu Ser Gly Arg Leu Phe Lys Gly Lys
                965             970             975

Val Leu Lys Arg His Gln Arg Glu Ile Thr Arg Thr Thr Leu Gln Ser
            980             985             990

Asp Gln Glu Glu Ile Asp Tyr Asp Asp Thr Ile Ser Val Glu Met Lys
            995             1000            1005
```

```
Lys Glu Asp Phe Asp Ile Tyr Asp Glu Asp Glu Asn Gln Ser Pro
    1010            1015            1020

Arg Ser Phe Gln Lys Lys Thr Arg His Tyr Phe Ile Ala Ala Val
    1025            1030            1035

Glu Arg Leu Trp Asp Tyr Gly Met Ser Ser Pro His Val Leu
    1040            1045            1050

Arg Asn Arg Ala Gln Ser Gly Ser Val Pro Gln Phe Lys Lys Val
    1055            1060            1065

Val Phe Gln Glu Phe Thr Asp Gly Ser Phe Thr Gln Pro Leu Tyr
    1070            1075            1080

Arg Gly Glu Leu Asn Glu His Leu Gly Leu Leu Gly Pro Tyr Ile
    1085            1090            1095

Arg Ala Glu Val Glu Asp Asn Ile Met Val Thr Phe Arg Asn Gln
    1100            1105            1110

Ala Ser Arg Pro Tyr Ser Phe Tyr Ser Ser Leu Ile Ser Tyr Glu
    1115            1120            1125

Glu Asp Gln Arg Gln Gly Ala Glu Pro Arg Lys Asn Phe Val Lys
    1130            1135            1140

Pro Asn Glu Thr Lys Thr Tyr Phe Trp Lys Val Gln His His Met
    1145            1150            1155

Ala Pro Thr Lys Asp Glu Phe Asp Cys Lys Ala Trp Ala Tyr Phe
    1160            1165            1170

Ser Asp Val Asp Leu Glu Lys Asp Val His Ser Gly Leu Ile Gly
    1175            1180            1185

Pro Leu Leu Val Cys His Thr Asn Thr Leu Asn Pro Ala His Gly
    1190            1195            1200

Arg Gln Val Thr Val Gln Glu Phe Ala Leu Phe Phe Thr Ile Phe
    1205            1210            1215

Asp Glu Thr Lys Ser Trp Tyr Phe Thr Glu Asn Met Glu Arg Asn
    1220            1225            1230

Cys Arg Ala Pro Cys Asn Ile Gln Met Glu Asp Pro Thr Phe Lys
    1235            1240            1245

Glu Asn Tyr Arg Phe His Ala Ile Asn Gly Tyr Ile Met Asp Thr
    1250            1255            1260

Leu Pro Gly Leu Val Met Ala Gln Asp Gln Arg Ile Arg Trp Tyr
    1265            1270            1275

Leu Leu Ser Met Gly Ser Asn Glu Asn Ile His Ser Ile His Phe
    1280            1285            1290

Ser Gly His Val Phe Thr Val Arg Lys Lys Glu Glu Tyr Lys Met
    1295            1300            1305

Ala Leu Tyr Asn Leu Tyr Pro Gly Val Phe Glu Thr Val Glu Met
    1310            1315            1320

Leu Pro Ser Lys Ala Gly Ile Trp Arg Val Glu Cys Leu Ile Gly
    1325            1330            1335

Glu His Leu His Ala Gly Met Ser Thr Leu Phe Leu Val Tyr Ser
    1340            1345            1350

Asn Lys Cys Gln Thr Pro Leu Gly Met Ala Ser Gly His Ile Arg
    1355            1360            1365

Asp Phe Gln Ile Thr Ala Ser Gly Gln Tyr Gly Gln Trp Ala Pro
    1370            1375            1380

Lys Leu Ala Arg Leu His Tyr Ser Gly Ser Ile Asn Ala Trp Ser
    1385            1390            1395
```

```
Thr Lys Glu Pro Phe Ser Trp Ile Lys Val Asp Leu Leu Ala Pro
1400                1405                1410

Met Ile Ile His Gly Ile Lys Thr Gln Gly Ala Arg Gln Lys Phe
1415                1420                1425

Ser Ser Leu Tyr Ile Ser Gln Phe Ile Ile Met Tyr Ser Leu Asp
1430                1435                1440

Gly Lys Lys Trp Gln Thr Tyr Arg Gly Asn Ser Thr Gly Thr Leu
1445                1450                1455

Met Val Phe Phe Gly Asn Val Asp Ser Ser Gly Ile Lys His Asn
1460                1465                1470

Ile Phe Asn Pro Pro Ile Ile Ala Arg Tyr Ile Arg Leu His Pro
1475                1480                1485

Thr His Tyr Ser Ile Arg Ser Thr Leu Arg Met Glu Leu Met Gly
1490                1495                1500

Cys Asp Leu Asn Ser Cys Ser Met Pro Leu Gly Met Glu Ser Lys
1505                1510                1515

Ala Ile Ser Asp Ala Gln Ile Thr Ala Ser Ser Tyr Phe Thr Asn
1520                1525                1530

Met Phe Ala Thr Trp Ser Pro Ser Lys Ala Arg Leu His Leu Gln
1535                1540                1545

Gly Arg Ser Asn Ala Trp Arg Pro Gln Val Asn Asn Pro Lys Glu
1550                1555                1560

Trp Leu Gln Val Asp Phe Gln Lys Thr Met Lys Val Thr Gly Val
1565                1570                1575

Thr Thr Gln Gly Val Lys Ser Leu Leu Thr Ser Met Tyr Val Lys
1580                1585                1590

Glu Phe Leu Ile Ser Ser Ser Gln Asp Gly His Gln Trp Thr Leu
1595                1600                1605

Phe Phe Gln Asn Gly Lys Val Lys Val Phe Gln Gly Asn Gln Asp
1610                1615                1620

Ser Phe Thr Pro Val Val Asn Ser Leu Asp Pro Pro Leu Leu Thr
1625                1630                1635

Arg Tyr Leu Arg Ile His Pro Gln Ser Trp Val His Gln Ile Ala
1640                1645                1650

Leu Arg Met Glu Val Leu Gly Cys Glu Ala Gln Asp Leu Tyr
1655                1660                1665

<210> SEQ ID NO 4
<211> LENGTH: 65
<212> TYPE: PRT
<213> ORGANISM: Artificial Sequence
<220> FEATURE:
<223> OTHER INFORMATION: vWF fragment: amino acids 764-828 (TIL')

<400> SEQUENCE: 4

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro
65
```

<210> SEQ ID NO 5
<211> LENGTH: 102
<212> TYPE: PRT
<213> ORGANISM: Artificial Sequence
<220> FEATURE:
<223> OTHER INFORMATION: vWF fragment: amino acids 764-865 (TIL'/E')

<400> SEQUENCE: 5

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala
            100
```

<210> SEQ ID NO 6
<211> LENGTH: 272
<212> TYPE: PRT
<213> ORGANISM: Artificial Sequence
<220> FEATURE:
<223> OTHER INFORMATION: vWF fragment: amino acids 764-1035
      (TIL'/E'/VWD3 I)

<400> SEQUENCE: 6

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
```

```
            195                 200                 205
Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

<210> SEQ ID NO 7
<211> LENGTH: 278
<212> TYPE: PRT
<213> ORGANISM: Artificial Sequence
<220> FEATURE:
<223> OTHER INFORMATION: vWF fragment: amino acids 764-1041
      (TIL'/E'/VWD3 II)

<400> SEQUENCE: 7

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser
                275
```

<210> SEQ ID NO 8
<211> LENGTH: 282
<212> TYPE: PRT
<213> ORGANISM: Artificial Sequence
<220> FEATURE:
<223> OTHER INFORMATION: vWF fragment: amino acids 764-1045
(TIL'/E'/VWD3 III)

<400> SEQUENCE: 8

```
Ser Leu Ser Cys Arg Pro Pro Met Val Lys Leu Val Cys Pro Ala Asp
  1               5                  10                  15

Asn Leu Arg Ala Glu Gly Leu Glu Cys Thr Lys Thr Cys Gln Asn Tyr
             20                  25                  30

Asp Leu Glu Cys Met Ser Met Gly Cys Val Ser Gly Cys Leu Cys Pro
         35                  40                  45

Pro Gly Met Val Arg His Glu Asn Arg Cys Val Ala Leu Glu Arg Cys
     50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Gln Asp Arg Lys Trp Asn Cys Thr
                 85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr
        275                 280
```

<210> SEQ ID NO 9
<211> LENGTH: 365
<212> TYPE: PRT
<213> ORGANISM: Artificial Sequence
<220> FEATURE:
<223> OTHER INFORMATION: vWF fragment: amino acids 764-1128
(TIL'/E'/VWD3/C8-3)

<400> SEQUENCE: 9

```
Ser Leu Ser Cys Arg Pro Pro Met Val Lys Leu Val Cys Pro Ala Asp
  1               5                  10                  15
```

```
Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
            130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
            210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln
            355                 360                 365

<210> SEQ ID NO 10
<211> LENGTH: 435
<212> TYPE: PRT
<213> ORGANISM: Artificial Sequence
<220> FEATURE:
<223> OTHER INFORMATION: vWF fragment: amino acids 764-1198
      (TIL'/E'/VWD3/C8-3/TIL-3)

<400> SEQUENCE: 10

Ser Leu Ser Cys Arg Pro Pro Met Val Lys Leu Val Cys Pro Ala Asp
1               5                   10                  15
```

```
Asn Leu Arg Ala Glu Gly Leu Glu Cys Thr Lys Thr Cys Gln Asn Tyr
             20                  25                  30

Asp Leu Glu Cys Met Ser Met Gly Cys Val Ser Gly Cys Leu Cys Pro
         35                  40                  45

Pro Gly Met Val Arg His Glu Asn Arg Cys Val Ala Leu Glu Arg Cys
 50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Gln Asp Arg Lys Trp Asn Cys Thr
                 85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
        130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
        210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430
```

```
Cys Pro Val
        435

<210> SEQ ID NO 11
<211> LENGTH: 487
<212> TYPE: PRT
<213> ORGANISM: Artificial Sequence
<220> FEATURE:
<223> OTHER INFORMATION: vWF fragment: amino acids 764-1250
      (TIL'/E'/D3 I

<400> SEQUENCE: 11

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350
```

```
Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
        370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
        450                 455                 460

Asp Val Val Asn Leu Thr Cys Glu Ala Cys Gln Glu Pro Gly Gly Leu
465                 470                 475                 480

Val Val Pro Pro Thr Asp Ala
            485

<210> SEQ ID NO 12
<211> LENGTH: 386
<212> TYPE: PRT
<213> ORGANISM: Artificial Sequence
<220> FEATURE:
<223> OTHER INFORMATION: vWF fragment: amino acids 864-1250 (D3 I)

<400> SEQUENCE: 12

Ala Thr Cys Ser Thr Ile Gly Met Ala His Tyr Leu Thr Phe Asp Gly
1               5                   10                  15

Leu Lys Tyr Leu Phe Pro Gly Glu Cys Gln Tyr Val Leu Val Gln Asp
            20                  25                  30

Tyr Cys Gly Ser Asn Pro Gly Thr Phe Arg Ile Leu Val Gly Asn Lys
        35                  40                  45

Gly Cys Ser His Pro Ser Val Lys Cys Lys Lys Arg Val Thr Ile Leu
    50                  55                  60

Val Glu Gly Gly Glu Ile Glu Leu Phe Asp Gly Glu Val Asn Val Lys
65                  70                  75                  80

Arg Pro Met Lys Asp Glu Thr His Phe Glu Val Val Glu Ser Gly Arg
            85                  90                  95

Tyr Ile Ile Leu Leu Leu Gly Lys Ala Leu Ser Val Val Trp Asp Arg
        100                 105                 110

His Leu Ser Ile Ser Val Val Leu Lys Gln Thr Tyr Gln Glu Lys Val
    115                 120                 125

Cys Gly Leu Cys Gly Asn Phe Asp Gly Ile Gln Asn Asn Asp Leu Thr
        130                 135                 140

Ser Ser Asn Leu Gln Val Glu Glu Asp Pro Val Asp Phe Gly Asn Ser
145                 150                 155                 160

Trp Lys Val Ser Ser Gln Cys Ala Asp Thr Arg Lys Val Pro Leu Asp
            165                 170                 175

Ser Ser Pro Ala Thr Cys His Asn Asn Ile Met Lys Gln Thr Met Val
            180                 185                 190

Asp Ser Ser Cys Arg Ile Leu Thr Ser Asp Val Phe Gln Asp Cys Asn
        195                 200                 205

Lys Leu Val Asp Pro Glu Pro Tyr Leu Asp Val Cys Ile Tyr Asp Thr
    210                 215                 220
```

```
Cys Ser Cys Glu Ser Ile Gly Asp Cys Ala Cys Phe Cys Asp Thr Ile
225                 230                 235                 240

Ala Ala Tyr Ala His Val Cys Ala Gln His Gly Lys Val Val Thr Trp
                245                 250                 255

Arg Thr Ala Thr Leu Cys Pro Gln Ser Cys Glu Glu Arg Asn Leu Arg
            260                 265                 270

Glu Asn Gly Tyr Glu Cys Glu Trp Arg Tyr Asn Ser Cys Ala Pro Ala
        275                 280                 285

Cys Gln Val Thr Cys Gln His Pro Glu Pro Leu Ala Cys Pro Val Gln
    290                 295                 300

Cys Val Glu Gly Cys His Ala His Cys Pro Pro Gly Lys Ile Leu Asp
305                 310                 315                 320

Glu Leu Leu Gln Thr Cys Val Asp Pro Glu Asp Cys Pro Val Cys Glu
                325                 330                 335

Val Ala Gly Arg Arg Phe Ala Ser Gly Lys Lys Val Thr Leu Asn Pro
                340                 345                 350

Ser Asp Pro Glu His Cys Gln Ile Cys His Cys Asp Val Val Asn Leu
            355                 360                 365

Thr Cys Glu Ala Cys Gln Glu Pro Gly Gly Leu Val Val Pro Pro Thr
    370                 375                 380

Asp Ala
385

<210> SEQ ID NO 13
<211> LENGTH: 405
<212> TYPE: PRT
<213> ORGANISM: Artificial Sequence
<220> FEATURE:
<223> OTHER INFORMATION: vWF fragment: amino acids 864-1268 (D3 II)

<400> SEQUENCE: 13

Ala Thr Cys Ser Thr Ile Gly Met Ala His Tyr Leu Thr Phe Asp Gly
1               5                   10                  15

Leu Lys Tyr Leu Phe Pro Gly Glu Cys Gln Tyr Val Leu Val Gln Asp
                20                  25                  30

Tyr Cys Gly Ser Asn Pro Gly Thr Phe Arg Ile Leu Val Gly Asn Lys
            35                  40                  45

Gly Cys Ser His Pro Ser Val Lys Cys Lys Arg Val Thr Ile Leu
        50                  55                  60

Val Glu Gly Gly Glu Ile Glu Leu Phe Asp Gly Glu Val Asn Val Lys
65                  70                  75                  80

Arg Pro Met Lys Asp Glu Thr His Phe Glu Val Val Glu Ser Gly Arg
                85                  90                  95

Tyr Ile Ile Leu Leu Leu Gly Lys Ala Leu Ser Val Val Trp Asp Arg
            100                 105                 110

His Leu Ser Ile Ser Val Val Leu Lys Gln Thr Tyr Gln Glu Lys Val
        115                 120                 125

Cys Gly Leu Cys Gly Asn Phe Asp Gly Ile Gln Asn Asn Asp Leu Thr
    130                 135                 140

Ser Ser Asn Leu Gln Val Glu Glu Asp Pro Val Asp Phe Gly Asn Ser
145                 150                 155                 160

Trp Lys Val Ser Ser Gln Cys Ala Asp Thr Arg Lys Val Pro Leu Asp
                165                 170                 175

Ser Ser Pro Ala Thr Cys His Asn Asn Ile Met Lys Gln Thr Met Val
            180                 185                 190
```

-continued

```
Asp Ser Ser Cys Arg Ile Leu Thr Ser Asp Val Phe Gln Asp Cys Asn
            195                 200                 205

Lys Leu Val Asp Pro Glu Pro Tyr Leu Asp Val Cys Ile Tyr Asp Thr
    210                 215                 220

Cys Ser Cys Glu Ser Ile Gly Asp Cys Ala Cys Phe Cys Asp Thr Ile
225                 230                 235                 240

Ala Ala Tyr Ala His Val Cys Ala Gln His Gly Lys Val Val Thr Trp
                245                 250                 255

Arg Thr Ala Thr Leu Cys Pro Gln Ser Cys Glu Glu Arg Asn Leu Arg
            260                 265                 270

Glu Asn Gly Tyr Glu Cys Glu Trp Arg Tyr Asn Ser Cys Ala Pro Ala
        275                 280                 285

Cys Gln Val Thr Cys Gln His Pro Glu Pro Leu Ala Cys Pro Val Gln
    290                 295                 300

Cys Val Glu Gly Cys His Ala His Cys Pro Gly Lys Ile Leu Asp
305                 310                 315                 320

Glu Leu Leu Gln Thr Cys Val Asp Pro Glu Asp Cys Pro Val Cys Glu
                325                 330                 335

Val Ala Gly Arg Arg Phe Ala Ser Gly Lys Lys Val Thr Leu Asn Pro
            340                 345                 350

Ser Asp Pro Glu His Cys Gln Ile Cys His Cys Asp Val Val Asn Leu
        355                 360                 365

Thr Cys Glu Ala Cys Gln Glu Pro Gly Gly Leu Val Val Pro Pro Thr
    370                 375                 380

Asp Ala Pro Val Ser Pro Thr Thr Leu Tyr Val Glu Asp Ile Ser Glu
385                 390                 395                 400

Pro Pro Leu His Asp
            405

<210> SEQ ID NO 14
<211> LENGTH: 498
<212> TYPE: PRT
<213> ORGANISM: Artificial Sequence
<220> FEATURE:
<223> OTHER INFORMATION: vWF fragment: amino acids 764-1261
      (TIL'/E'/D3 II)

<400> SEQUENCE: 14

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
```

```
                130               135               140
Leu Val Gly Asn Lys Gly Cys Ser His Pro Ser Val Lys Cys Lys Lys
145                 150                 155                 160

Arg Val Thr Ile Leu Val Glu Gly Glu Ile Glu Leu Phe Asp Gly
                165                 170                 175

Glu Val Asn Val Lys Arg Pro Met Lys Asp Thr His Phe Glu Val
                180                 185                 190

Val Glu Ser Gly Arg Tyr Ile Ile Leu Leu Gly Lys Ala Leu Ser
                195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
                275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp

<210> SEQ ID NO 15
<211> LENGTH: 502
<212> TYPE: PRT
<213> ORGANISM: Artificial Sequence
<220> FEATURE:
<223> OTHER INFORMATION: vWF fragment: amino acids 764-1264
      (TIL'/E'/D3 III)
```

```
<400> SEQUENCE: 15

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415
```

```
Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
            485                 490                 495

Glu Asp Ile Ser Glu Pro
            500

<210> SEQ ID NO 16
<211> LENGTH: 506
<212> TYPE: PRT
<213> ORGANISM: Artificial Sequence
<220> FEATURE:
<223> OTHER INFORMATION: vWF fragment: amino acids 764-1268
      (TIL'/E'/D3 IV)

<400> SEQUENCE: 16

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
```

260                 265                 270
Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
        290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp
            500                 505

<210> SEQ ID NO 17
<211> LENGTH: 696
<212> TYPE: PRT
<213> ORGANISM: Artificial Sequence
<220> FEATURE:
<223> OTHER INFORMATION: vWF fragment: amino acids 764-1459
      (TIL'/E'/D3/A1 I)

<400> SEQUENCE: 17

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

-continued

```
Leu Thr Phe Asp Gly Leu Lys Tyr Leu Phe Pro Gly Glu Cys Gln Tyr
        115                 120                 125
Val Leu Val Gln Asp Tyr Cys Gly Ser Asn Pro Gly Thr Phe Arg Ile
    130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                165                 170                 175
Glu Val Asn Val Lys Arg Pro Met Lys Asp Glu Thr His Phe Glu Val
            180                 185                 190
Val Glu Ser Gly Arg Tyr Ile Ile Leu Leu Gly Lys Ala Leu Ser
        195                 200                 205
Val Val Trp Asp Arg His Leu Ser Ile Ser Val Val Leu Lys Gln Thr
    210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
Asp Phe Gly Asn Ser Trp Lys Val Ser Ser Gln Cys Ala Asp Thr Arg
            260                 265                 270
Lys Val Pro Leu Asp Ser Ser Pro Ala Thr Cys His Asn Asn Ile Met
        275                 280                 285
Lys Gln Thr Met Val Asp Ser Ser Cys Arg Ile Leu Thr Ser Asp Val
    290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
            340                 345                 350
Lys Val Val Thr Trp Arg Thr Ala Thr Leu Cys Pro Gln Ser Cys Glu
        355                 360                 365
Glu Arg Asn Leu Arg Glu Asn Gly Tyr Glu Cys Glu Trp Arg Tyr Asn
    370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
        435                 440                 445
Val Thr Leu Asn Pro Ser Asp Pro Glu His Cys Gln Ile Cys His Cys
    450                 455                 460
Asp Val Val Asn Leu Thr Cys Glu Ala Cys Gln Glu Pro Gly Gly Leu
465                 470                 475                 480
Val Val Pro Pro Thr Asp Ala Pro Val Ser Pro Thr Thr Leu Tyr Val
                485                 490                 495
Glu Asp Ile Ser Glu Pro Pro Leu His Asp Phe Tyr Cys Ser Arg Leu
            500                 505                 510
Leu Asp Leu Val Phe Leu Leu Asp Gly Ser Ser Arg Leu Ser Glu Ala
        515                 520                 525
Glu Phe Glu Val Leu Lys Ala Phe Val Val Asp Met Met Glu Arg Leu
```

```
               530                 535                 540
Arg Ile Ser Gln Lys Trp Val Arg Val Ala Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
                580                 585                 590

Ser Thr Ser Glu Val Leu Lys Tyr Thr Leu Phe Gln Ile Phe Ser Lys
                595                 600                 605

Ile Asp Arg Pro Glu Ala Ser Arg Ile Thr Leu Leu Leu Met Ala Ser
610                 615                 620

Gln Glu Pro Gln Arg Met Ser Arg Asn Phe Val Arg Tyr Val Gln Gly
625                 630                 635                 640

Leu Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
                660                 665                 670

Lys Ala Phe Val Leu Ser Ser Val Asp Glu Leu Glu Gln Gln Arg Asp
                675                 680                 685

Glu Ile Val Ser Tyr Leu Cys Asp
                690                 695

<210> SEQ ID NO 18
<211> LENGTH: 700
<212> TYPE: PRT
<213> ORGANISM: Artificial Sequence
<220> FEATURE:
<223> OTHER INFORMATION: vWF fragment: amino acids 764-1463
      (TIL'/E'/D3/A1 II)

<400> SEQUENCE: 18

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
                35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
                115                 120                 125

Val Leu Val Gln Asp Tyr Cys Gly Ser Asn Pro Gly Thr Phe Arg Ile
                130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190
```

-continued

```
Val Glu Ser Gly Arg Tyr Ile Ile Leu Leu Gly Lys Ala Leu Ser
            195                 200                 205

Val Val Trp Asp Arg His Leu Ser Ile Ser Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
```

```
                     610                 615                 620
Gln Glu Pro Gln Arg Met Ser Arg Asn Phe Val Arg Tyr Val Gln Gly
625                 630                 635                 640

Leu Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
                660                 665                 670

Lys Ala Phe Val Leu Ser Ser Val Asp Glu Leu Glu Gln Gln Arg Asp
                675                 680                 685

Glu Ile Val Ser Tyr Leu Cys Asp Leu Ala Pro Glu
690                 695                 700

<210> SEQ ID NO 19
<211> LENGTH: 701
<212> TYPE: PRT
<213> ORGANISM: Artificial Sequence
<220> FEATURE:
<223> OTHER INFORMATION: vWF fragment: amino acids 764-1464
      (TIL'/E'/D3/A1 III)

<400> SEQUENCE: 19

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
                35                  40                  45

Pro Gly Met Val Arg His Glu Asn Arg Cys Val Ala Leu Glu Arg Cys
            50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
                115                 120                 125

Val Leu Val Gln Asp Tyr Cys Gly Ser Asn Pro Gly Thr Phe Arg Ile
                130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Leu Gly Lys Ala Leu Ser
                195                 200                 205

Val Val Trp Asp Arg His Leu Ser Ile Ser Val Val Leu Lys Gln Thr
                210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270
```

```
                    -continued

Lys Val Pro Leu Asp Ser Ser Pro Ala Thr Cys His Asn Asn Ile Met
                275                 280                 285
Lys Gln Thr Met Val Asp Ser Ser Cys Arg Ile Leu Thr Ser Asp Val
        290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
                340                 345                 350
Lys Val Val Thr Trp Arg Thr Ala Thr Leu Cys Pro Gln Ser Cys Glu
        355                 360                 365
Glu Arg Asn Leu Arg Glu Asn Gly Tyr Glu Cys Glu Trp Arg Tyr Asn
370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
                420                 425                 430
Cys Pro Val Cys Glu Val Ala Gly Arg Arg Phe Ala Ser Gly Lys Lys
        435                 440                 445
Val Thr Leu Asn Pro Ser Asp Pro Glu His Cys Gln Ile Cys His Cys
        450                 455                 460
Asp Val Val Asn Leu Thr Cys Glu Ala Cys Gln Glu Pro Gly Gly Leu
465                 470                 475                 480
Val Val Pro Pro Thr Asp Ala Pro Val Ser Pro Thr Thr Leu Tyr Val
                485                 490                 495
Glu Asp Ile Ser Glu Pro Pro Leu His Asp Phe Tyr Cys Ser Arg Leu
                500                 505                 510
Leu Asp Leu Val Phe Leu Leu Asp Gly Ser Ser Arg Leu Ser Glu Ala
        515                 520                 525
Glu Phe Glu Val Leu Lys Ala Phe Val Val Asp Met Met Glu Arg Leu
530                 535                 540
Arg Ile Ser Gln Lys Trp Val Arg Val Ala Val Val Glu Tyr His Asp
545                 550                 555                 560
Gly Ser His Ala Tyr Ile Gly Leu Lys Asp Arg Lys Arg Pro Ser Glu
                565                 570                 575
Leu Arg Arg Ile Ala Ser Gln Val Lys Tyr Ala Gly Ser Gln Val Ala
                580                 585                 590
Ser Thr Ser Glu Val Leu Lys Tyr Thr Leu Phe Gln Ile Phe Ser Lys
        595                 600                 605
Ile Asp Arg Pro Glu Ala Ser Arg Ile Thr Leu Leu Leu Met Ala Ser
        610                 615                 620
Gln Glu Pro Gln Arg Met Ser Arg Asn Phe Val Arg Tyr Val Gln Gly
625                 630                 635                 640
Leu Lys Lys Lys Lys Val Ile Val Ile Pro Val Gly Ile Gly Pro His
                645                 650                 655
Ala Asn Leu Lys Gln Ile Arg Leu Ile Glu Lys Gln Ala Pro Glu Asn
                660                 665                 670
Lys Ala Phe Val Leu Ser Ser Val Asp Glu Leu Glu Gln Gln Arg Asp
                675                 680                 685
Glu Ile Val Ser Tyr Leu Cys Asp Leu Ala Pro Glu Ala
```

<210> SEQ ID NO 20
<211> LENGTH: 920
<212> TYPE: PRT
<213> ORGANISM: Artificial Sequence
<220> FEATURE:
<223> OTHER INFORMATION: vWF fragment: amino acids 764-1683
(TIL'/E'/D3/A1/A2)

<400> SEQUENCE: 20

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350
```

```
Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
        370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
    690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
                725                 730                 735

Ala Phe Val Leu Glu Gly Ser Asp Lys Ile Gly Glu Ala Asp Phe Asn
            740                 745                 750

Arg Ser Lys Glu Phe Met Glu Glu Val Ile Gln Arg Met Asp Val Gly
        755                 760                 765

Gln Asp Ser Ile His Val Thr Val Leu Gln Tyr Ser Tyr Met Val Thr
```

```
                   770                 775                 780
Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                    805                 810                 815

Leu Ala Leu Arg Tyr Leu Ser Asp His Ser Phe Leu Val Ser Gln Gly
                820                 825                 830

Asp Arg Glu Gln Ala Pro Asn Leu Val Tyr Met Val Thr Gly Asn Pro
            835                 840                 845

Ala Ser Asp Glu Ile Lys Arg Leu Pro Gly Asp Ile Gln Val Val Pro
        850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                    885                 890                 895

Glu Ala Pro Asp Leu Val Leu Gln Arg Cys Cys Ser Gly Glu Gly Leu
                900                 905                 910

Gln Ile Pro Thr Leu Ser Pro Ala
            915                 920

<210> SEQ ID NO 21
<211> LENGTH: 1110
<212> TYPE: PRT
<213> ORGANISM: Artificial Sequence
<220> FEATURE:
<223> OTHER INFORMATION: vWF fragment: amino acids 764-1873
      (TIL'/E'/D3/A1/A2/A3)

<400> SEQUENCE: 21

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205
```

Val Val Trp Asp Arg His Leu Ser Ile Ser Val Val Leu Lys Gln Thr
210                     215                     220

Tyr Gln Glu Lys Val Cys Gly Leu Cys Gly Asn Phe Asp Gly Ile Gln
225                     230                     235                     240

Asn Asn Asp Leu Thr Ser Ser Asn Leu Gln Val Glu Glu Asp Pro Val
                245                     250                     255

Asp Phe Gly Asn Ser Trp Lys Val Ser Ser Gln Cys Ala Asp Thr Arg
            260                     265                     270

Lys Val Pro Leu Asp Ser Ser Pro Ala Thr Cys His Asn Asn Ile Met
            275                     280                     285

Lys Gln Thr Met Val Asp Ser Ser Cys Arg Ile Leu Thr Ser Asp Val
290                     295                     300

Phe Gln Asp Cys Asn Lys Leu Val Asp Pro Glu Pro Tyr Leu Asp Val
305                     310                     315                     320

Cys Ile Tyr Asp Thr Cys Ser Cys Glu Ser Ile Gly Asp Cys Ala Cys
                325                     330                     335

Phe Cys Asp Thr Ile Ala Ala Tyr Ala His Val Cys Ala Gln His Gly
            340                     345                     350

Lys Val Val Thr Trp Arg Thr Ala Thr Leu Cys Pro Gln Ser Cys Glu
            355                     360                     365

Glu Arg Asn Leu Arg Glu Asn Gly Tyr Glu Cys Glu Trp Arg Tyr Asn
370                     375                     380

Ser Cys Ala Pro Ala Cys Gln Val Thr Cys Gln His Pro Glu Pro Leu
385                     390                     395                     400

Ala Cys Pro Val Gln Cys Val Glu Gly Cys His Ala His Cys Pro Pro
                405                     410                     415

Gly Lys Ile Leu Asp Glu Leu Leu Gln Thr Cys Val Asp Pro Glu Asp
            420                     425                     430

Cys Pro Val Cys Glu Val Ala Gly Arg Arg Phe Ala Ser Gly Lys Lys
            435                     440                     445

Val Thr Leu Asn Pro Ser Asp Pro Glu His Cys Gln Ile Cys His Cys
450                     455                     460

Asp Val Val Asn Leu Thr Cys Glu Ala Cys Gln Glu Pro Gly Gly Leu
465                     470                     475                     480

Val Val Pro Pro Thr Asp Ala Pro Val Ser Pro Thr Thr Leu Tyr Val
                485                     490                     495

Glu Asp Ile Ser Glu Pro Pro Leu His Asp Phe Tyr Cys Ser Arg Leu
            500                     505                     510

Leu Asp Leu Val Phe Leu Leu Asp Gly Ser Ser Arg Leu Ser Glu Ala
            515                     520                     525

Glu Phe Glu Val Leu Lys Ala Phe Val Val Asp Met Met Glu Arg Leu
530                     535                     540

Arg Ile Ser Gln Lys Trp Val Arg Val Ala Val Val Glu Tyr His Asp
545                     550                     555                     560

Gly Ser His Ala Tyr Ile Gly Leu Lys Asp Arg Lys Arg Pro Ser Glu
                565                     570                     575

Leu Arg Arg Ile Ala Ser Gln Val Lys Tyr Ala Gly Ser Gln Val Ala
            580                     585                     590

Ser Thr Ser Glu Val Leu Lys Tyr Thr Leu Phe Gln Ile Phe Ser Lys
            595                     600                     605

Ile Asp Arg Pro Glu Ala Ser Arg Ile Thr Leu Leu Leu Met Ala Ser
610                     615                     620

Gln Glu Pro Gln Arg Met Ser Arg Asn Phe Val Arg Tyr Val Gln Gly

```
            625                 630                 635                 640
Leu Lys Lys Lys Val Ile Val Ile Pro Val Gly Ile Gly Pro His
                645                 650                 655
Ala Asn Leu Lys Gln Ile Arg Leu Ile Glu Lys Gln Ala Pro Glu Asn
                660                 665                 670
Lys Ala Phe Val Leu Ser Ser Val Asp Glu Leu Glu Gln Arg Asp
                675                 680                 685
Glu Ile Val Ser Tyr Leu Cys Asp Leu Ala Pro Glu Ala Pro Pro
        690                 695                 700
Thr Leu Pro Pro Asp Met Ala Gln Val Thr Val Gly Pro Gly Leu Leu
705                 710                 715                 720
Gly Val Ser Thr Leu Gly Pro Lys Arg Asn Ser Met Val Leu Asp Val
                    725                 730                 735
Ala Phe Val Leu Glu Gly Ser Asp Lys Ile Gly Glu Ala Asp Phe Asn
                740                 745                 750
Arg Ser Lys Glu Phe Met Glu Glu Val Ile Gln Arg Met Asp Val Gly
        755                 760                 765
Gln Asp Ser Ile His Val Thr Val Leu Gln Tyr Ser Tyr Met Val Thr
    770                 775                 780
Val Glu Tyr Pro Phe Ser Glu Ala Gln Ser Lys Gly Asp Ile Leu Gln
785                 790                 795                 800
Arg Val Arg Glu Ile Arg Tyr Gln Gly Gly Asn Arg Thr Asn Thr Gly
                    805                 810                 815
Leu Ala Leu Arg Tyr Leu Ser Asp His Ser Phe Leu Val Ser Gln Gly
                820                 825                 830
Asp Arg Glu Gln Ala Pro Asn Leu Val Tyr Met Val Thr Gly Asn Pro
        835                 840                 845
Ala Ser Asp Glu Ile Lys Arg Leu Pro Gly Asp Ile Gln Val Val Pro
    850                 855                 860
Ile Gly Val Gly Pro Asn Ala Asn Val Gln Glu Leu Glu Arg Ile Gly
865                 870                 875                 880
Trp Pro Asn Ala Pro Ile Leu Ile Gln Asp Phe Glu Thr Leu Pro Arg
                    885                 890                 895
Glu Ala Pro Asp Leu Val Leu Gln Arg Cys Cys Ser Gly Glu Gly Leu
                900                 905                 910
Gln Ile Pro Thr Leu Ser Pro Ala Pro Asp Cys Ser Gln Pro Leu Asp
        915                 920                 925
Val Ile Leu Leu Leu Asp Gly Ser Ser Ser Phe Pro Ala Ser Tyr Phe
    930                 935                 940
Asp Glu Met Lys Ser Phe Ala Lys Ala Phe Ile Ser Lys Ala Asn Ile
945                 950                 955                 960
Gly Pro Arg Leu Thr Gln Val Ser Val Leu Gln Tyr Gly Ser Ile Thr
                    965                 970                 975
Thr Ile Asp Val Pro Trp Asn Val Val Pro Glu Lys Ala His Leu Leu
                980                 985                 990
Ser Leu Val Asp Val Met Gln Arg Glu Gly Gly Pro Ser Gln Ile Gly
            995                 1000                1005
Asp Ala Leu Gly Phe Ala Val Arg Tyr Leu Thr Ser Glu Met His
    1010                1015                1020
Gly Ala Arg Pro Gly Ala Ser Lys Ala Val Val Ile Leu Val Thr
    1025                1030                1035
Asp Val Ser Val Asp Ser Val Asp Ala Ala Ala Asp Ala Ala Arg
    1040                1045                1050
```

```
Ser Asn Arg Val Thr Val Phe Pro Ile Gly Ile Gly Asp Arg Tyr
    1055            1060            1065

Asp Ala Ala Gln Leu Arg Ile Leu Ala Gly Pro Ala Gly Asp Ser
    1070            1075            1080

Asn Val Val Lys Leu Gln Arg Ile Glu Asp Leu Pro Thr Met Val
    1085            1090            1095

Thr Leu Gly Asn Ser Phe Leu His Lys Leu Cys Ser
    1100            1105            1110

<210> SEQ ID NO 22
<211> LENGTH: 2813
<212> TYPE: PRT
<213> ORGANISM: Homo sapiens

<400> SEQUENCE: 22

Met Ile Pro Ala Arg Phe Ala Gly Val Leu Ala Leu Ala Leu Ile
1               5                   10                  15

Leu Pro Gly Thr Leu Cys Ala Glu Gly Thr Arg Gly Arg Ser Ser
                20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
```

```
        305                 310                 315                 320
Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
                355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Glu Thr Val Gln Cys
                420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
                450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
                515                 520                 525

Gly Asn Gln Gly Asp Asp Phe Leu Thr Pro Ser Gly Leu Ala Glu Pro
                530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
                610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
                675                 680                 685

Cys Pro Pro Gly Leu Tyr Met Asp Glu Arg Gly Asp Cys Val Pro Lys
                690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735
```

```
His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Gln Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
            930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
            965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140
```

```
Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Thr Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro Asp Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
```

-continued

```
             1535                1540                1545

Glu Tyr Pro Phe Ser Glu Ala Gln Ser Lys Gly Asp Ile Leu Gln
        1550                1555                1560

Arg Val Arg Glu Ile Arg Tyr Gln Gly Gly Asn Arg Thr Asn Thr
        1565                1570                1575

Gly Leu Ala Leu Arg Tyr Leu Ser Asp His Ser Phe Leu Val Ser
        1580                1585                1590

Gln Gly Asp Arg Glu Gln Ala Pro Asn Leu Val Tyr Met Val Thr
        1595                1600                1605

Gly Asn Pro Ala Ser Asp Glu Ile Lys Arg Leu Pro Gly Asp Ile
        1610                1615                1620

Gln Val Val Pro Ile Gly Val Gly Pro Asn Ala Asn Val Gln Glu
        1625                1630                1635

Leu Glu Arg Ile Gly Trp Pro Asn Ala Pro Ile Leu Ile Gln Asp
        1640                1645                1650

Phe Glu Thr Leu Pro Arg Glu Ala Pro Asp Leu Val Leu Gln Arg
        1655                1660                1665

Cys Cys Ser Gly Glu Gly Leu Gln Ile Pro Thr Leu Ser Pro Ala
        1670                1675                1680

Pro Asp Cys Ser Gln Pro Leu Asp Val Ile Leu Leu Leu Asp Gly
        1685                1690                1695

Ser Ser Ser Phe Pro Ala Ser Tyr Phe Asp Glu Met Lys Ser Phe
        1700                1705                1710

Ala Lys Ala Phe Ile Ser Lys Ala Asn Ile Gly Pro Arg Leu Thr
        1715                1720                1725

Gln Val Ser Val Leu Gln Tyr Gly Ser Ile Thr Thr Ile Asp Val
        1730                1735                1740

Pro Trp Asn Val Val Pro Glu Lys Ala His Leu Leu Ser Leu Val
        1745                1750                1755

Asp Val Met Gln Arg Glu Gly Gly Pro Ser Gln Ile Gly Asp Ala
        1760                1765                1770

Leu Gly Phe Ala Val Arg Tyr Leu Thr Ser Glu Met His Gly Ala
        1775                1780                1785

Arg Pro Gly Ala Ser Lys Ala Val Val Ile Leu Val Thr Asp Val
        1790                1795                1800

Ser Val Asp Ser Val Asp Ala Ala Asp Ala Ala Arg Ser Asn
        1805                1810                1815

Arg Val Thr Val Phe Pro Ile Gly Ile Gly Asp Arg Tyr Asp Ala
        1820                1825                1830

Ala Gln Leu Arg Ile Leu Ala Gly Pro Ala Gly Asp Ser Asn Val
        1835                1840                1845

Val Lys Leu Gln Arg Ile Glu Asp Leu Pro Thr Met Val Thr Leu
        1850                1855                1860

Gly Asn Ser Phe Leu His Lys Leu Cys Ser Gly Phe Val Arg Ile
        1865                1870                1875

Cys Met Asp Glu Asp Gly Asn Glu Lys Arg Pro Gly Asp Val Trp
        1880                1885                1890

Thr Leu Pro Asp Gln Cys His Thr Val Thr Cys Gln Pro Asp Gly
        1895                1900                1905

Gln Thr Leu Leu Lys Ser His Arg Val Asn Cys Asp Arg Gly Leu
        1910                1915                1920

Arg Pro Ser Cys Pro Asn Ser Gln Ser Pro Val Lys Val Glu Glu
        1925                1930                1935
```

```
Thr Cys Gly Cys Arg Trp Thr Cys Pro Cys Val Cys Thr Gly Ser
    1940            1945            1950

Ser Thr Arg His Ile Val Thr Phe Asp Gly Gln Asn Phe Lys Leu
    1955            1960            1965

Thr Gly Ser Cys Ser Tyr Val Leu Phe Gln Asn Lys Glu Gln Asp
    1970            1975            1980

Leu Glu Val Ile Leu His Asn Gly Ala Cys Ser Pro Gly Ala Arg
    1985            1990            1995

Gln Gly Cys Met Lys Ser Ile Glu Val Lys His Ser Ala Leu Ser
    2000            2005            2010

Val Glu Leu His Ser Asp Met Glu Val Thr Val Asn Gly Arg Leu
    2015            2020            2025

Val Ser Val Pro Tyr Val Gly Gly Asn Met Glu Val Asn Val Tyr
    2030            2035            2040

Gly Ala Ile Met His Glu Val Arg Phe Asn His Leu Gly His Ile
    2045            2050            2055

Phe Thr Phe Thr Pro Gln Asn Asn Glu Phe Gln Leu Gln Leu Ser
    2060            2065            2070

Pro Lys Thr Phe Ala Ser Lys Thr Tyr Gly Leu Cys Gly Ile Cys
    2075            2080            2085

Asp Glu Asn Gly Ala Asn Asp Phe Met Leu Arg Asp Gly Thr Val
    2090            2095            2100

Thr Thr Asp Trp Lys Thr Leu Val Gln Glu Trp Thr Val Gln Arg
    2105            2110            2115

Pro Gly Gln Thr Cys Gln Pro Ile Leu Glu Glu Gln Cys Leu Val
    2120            2125            2130

Pro Asp Ser Ser His Cys Gln Val Leu Leu Leu Pro Leu Phe Ala
    2135            2140            2145

Glu Cys His Lys Val Leu Ala Pro Ala Thr Phe Tyr Ala Ile Cys
    2150            2155            2160

Gln Gln Asp Ser Cys His Gln Glu Gln Val Cys Glu Val Ile Ala
    2165            2170            2175

Ser Tyr Ala His Leu Cys Arg Thr Asn Gly Val Cys Val Asp Trp
    2180            2185            2190

Arg Thr Pro Asp Phe Cys Ala Met Ser Cys Pro Pro Ser Leu Val
    2195            2200            2205

Tyr Asn His Cys Glu His Gly Cys Pro Arg His Cys Asp Gly Asn
    2210            2215            2220

Val Ser Ser Cys Gly Asp His Pro Ser Glu Gly Cys Phe Cys Pro
    2225            2230            2235

Pro Asp Lys Val Met Leu Glu Gly Ser Cys Val Pro Glu Glu Ala
    2240            2245            2250

Cys Thr Gln Cys Ile Gly Glu Asp Gly Val Gln His Gln Phe Leu
    2255            2260            2265

Glu Ala Trp Val Pro Asp His Gln Pro Cys Gln Ile Cys Thr Cys
    2270            2275            2280

Leu Ser Gly Arg Lys Val Asn Cys Thr Thr Gln Pro Cys Pro Thr
    2285            2290            2295

Ala Lys Ala Pro Thr Cys Gly Leu Cys Glu Val Ala Arg Leu Arg
    2300            2305            2310

Gln Asn Ala Asp Gln Cys Cys Pro Glu Tyr Glu Cys Val Cys Asp
    2315            2320            2325
```

-continued

```
Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
```

```
                  2720            2725            2730
Val Lys Val Gly Ser Cys Lys Ser Glu Val Glu Val Asp Ile His
            2735            2740            2745

Tyr Cys Gln Gly Lys Cys Ala Ser Lys Ala Met Tyr Ser Ile Asp
            2750            2755            2760

Ile Asn Asp Val Gln Asp Gln Cys Ser Cys Ser Pro Thr Arg
        2765            2770            2775

Thr Glu Pro Met Gln Val Ala Leu His Cys Thr Asn Gly Ser Val
        2780            2785            2790

Val Tyr His Glu Val Leu Asn Ala Met Glu Cys Lys Cys Ser Pro
        2795            2800            2805

Arg Lys Cys Ser Lys
        2810

<210> SEQ ID NO 23
<211> LENGTH: 43
<212> TYPE: DNA
<213> ORGANISM: Artificial Sequence
<220> FEATURE:
<223> OTHER INFORMATION: forward primer JP1000 VWF-HindIII S

<400> SEQUENCE: 23
ctaagcgtaa gcttgccacc atgattcctg ccagatttgc cgg                    43

<210> SEQ ID NO 24
<211> LENGTH: 40
<212> TYPE: DNA
<213> ORGANISM: Artificial Sequence
<220> FEATURE:
<223> OTHER INFORMATION: Reverse primer JP1001 VWF 764-828

<400> SEQUENCE: 24
tggtcctcag ctagcgcggg acacctttcc agggccacac                        40

<210> SEQ ID NO 25
<211> LENGTH: 40
<212> TYPE: DNA
<213> ORGANISM: Artificial Sequence
<220> FEATURE:
<223> OTHER INFORMATION: Reverse primer JP1002 VWF 764-865

<400> SEQUENCE: 25
tggtcctcag ctagcgcggc atcacacaca tggtctgtgc                        40

<210> SEQ ID NO 26
<211> LENGTH: 42
<212> TYPE: DNA
<213> ORGANISM: Artificial Sequence
<220> FEATURE:
<223> OTHER INFORMATION: Reverse primer JP1003 VWF 764-1035

<400> SEQUENCE: 26
tggtcctcag ctagcgctct ggtgtcagca cactgcgagc tc                     42

<210> SEQ ID NO 27
<211> LENGTH: 40
<212> TYPE: DNA
<213> ORGANISM: Artificial Sequence
<220> FEATURE:
<223> OTHER INFORMATION: Reverse primer JP1004 VWF 764-1041

<400> SEQUENCE: 27
tggtcctcag ctagcgctga gtccagaggc actttctgg                         40
```

<210> SEQ ID NO 28
<211> LENGTH: 40
<212> TYPE: DNA
<213> ORGANISM: Artificial Sequence
<220> FEATURE:
<223> OTHER INFORMATION: Reverse primer JP1005 VWF 764-1045

<400> SEQUENCE: 28
tggtcctcag ctagcgcggt ggcaggggat gagtccagag                                40

<210> SEQ ID NO 29
<211> LENGTH: 39
<212> TYPE: DNA
<213> ORGANISM: Artificial Sequence
<220> FEATURE:
<223> OTHER INFORMATION: Reverse primer JP1006 VWF 764-1250

<400> SEQUENCE: 29
tggtcctcag ctagcgcggc atctgtggga ggcaccacc                                 39

<210> SEQ ID NO 30
<211> LENGTH: 39
<212> TYPE: DNA
<213> ORGANISM: Artificial Sequence
<220> FEATURE:
<223> OTHER INFORMATION: Reverse primer JP1007 VWF 764-1261

<400> SEQUENCE: 30
tggtcctcag ctagcgcgtc ctccacatac agagtggtg                                 39

<210> SEQ ID NO 31
<211> LENGTH: 39
<212> TYPE: DNA
<213> ORGANISM: Artificial Sequence
<220> FEATURE:
<223> OTHER INFORMATION: Reverse primer JP1008 VWF 764-1268

<400> SEQUENCE: 31
tggtcctcag ctagcgcatc gtgcaacggc ggttccgag                                 39

<210> SEQ ID NO 32
<211> LENGTH: 35
<212> TYPE: DNA
<213> ORGANISM: Artificial Sequence
<220> FEATURE:
<223> OTHER INFORMATION: VWF(864-1250)-HPC4 S

<400> SEQUENCE: 32
gggacccttt gtgatgccac gtgctccacg atcgg                                    35

<210> SEQ ID NO 33
<211> LENGTH: 36
<212> TYPE: DNA
<213> ORGANISM: Artificial Sequence
<220> FEATURE:
<223> OTHER INFORMATION: VWF(864-1250)-HPC4 AS

<400> SEQUENCE: 33
gcacgtggca tcacaaaggg tccctggcaa aatgag                                   36

<210> SEQ ID NO 34
<211> LENGTH: 36
<212> TYPE: DNA
<213> ORGANISM: Artificial Sequence
<220> FEATURE:

-continued

<223> OTHER INFORMATION: VWF(764-1128)-HPC4 S

<400> SEQUENCE: 34
ttgtgccccc aggaggacca agtagatccg cggctc                                36

<210> SEQ ID NO 35
<211> LENGTH: 34
<212> TYPE: DNA
<213> ORGANISM: Artificial Sequence
<220> FEATURE:
<223> OTHER INFORMATION: VWF(764-1129)-HPC4 AS

<400> SEQUENCE: 35
tacttggtcc tcctgggggc acaatgtggc cgtc                                  34

<210> SEQ ID NO 36
<211> LENGTH: 33
<212> TYPE: DNA
<213> ORGANISM: Artificial Sequence
<220> FEATURE:
<223> OTHER INFORMATION: VWF(764-1198)-HPC4 S

<400> SEQUENCE: 36
gactgtccag tggaggacca agtagatccg cgg                                   33

<210> SEQ ID NO 37
<211> LENGTH: 32
<212> TYPE: DNA
<213> ORGANISM: Artificial Sequence
<220> FEATURE:
<223> OTHER INFORMATION: VWF(764-1198)-HPC4 AS

<400> SEQUENCE: 37
ttggtcctcc actggacagt cttcagggtc aa                                    32

<210> SEQ ID NO 38
<211> LENGTH: 12
<212> TYPE: PRT
<213> ORGANISM: Artificial Sequence
<220> FEATURE:
<223> OTHER INFORMATION: HPC4 tag

<400> SEQUENCE: 38

Glu Asp Gln Val Asp Pro Arg Leu Ile Asp Gly Lys
1               5                   10

<210> SEQ ID NO 39
<211> LENGTH: 100
<212> TYPE: DNA
<213> ORGANISM: Artificial Sequence
<220> FEATURE:
<223> OTHER INFORMATION: oLLC089 VWF forward

<400> SEQUENCE: 39
ccgctagccc atgattcctg ccagatttgc cggggtgctg cttgctctgg ccctcatttt      60
gccagggacc ctttgtagcc tatcctgtcg gccccccatg                           100

<210> SEQ ID NO 40
<211> LENGTH: 85
<212> TYPE: DNA
<213> ORGANISM: Artificial Sequence
<220> FEATURE:
<223> OTHER INFORMATION: oLLC092 VWF A1 HPC4 reverse

<400> SEQUENCE: 40

```
gatgcggccg cctactacta tttgccatca atcagacgcg gatccacctg atcttcggct      60 tcagggggcaa ggtcacagag gtagc                                           85
```

<210> SEQ ID NO 41
<211> LENGTH: 40
<212> TYPE: DNA
<213> ORGANISM: Artificial Sequence
<220> FEATURE:
<223> OTHER INFORMATION: oLLC101-f

<400> SEQUENCE: 41

```
cattggggac tgcgcctcct tctgcgacac cattgctgcc                            40
```

<210> SEQ ID NO 42
<211> LENGTH: 40
<212> TYPE: DNA
<213> ORGANISM: Artificial Sequence
<220> FEATURE:
<223> OTHER INFORMATION: oLLC102-r

<400> SEQUENCE: 42

```
ggcagcaatg gtgtcgcaga aggaggcgca gtccccaatg                            40
```

<210> SEQ ID NO 43
<211> LENGTH: 44
<212> TYPE: DNA
<213> ORGANISM: Artificial Sequence
<220> FEATURE:
<223> OTHER INFORMATION: oLLC103-f

<400> SEQUENCE: 43

```
cgggagaacg ggtatgagtc tgagtggcgc tataacagct gtgc                       44
```

<210> SEQ ID NO 44
<211> LENGTH: 44
<212> TYPE: DNA
<213> ORGANISM: Artificial Sequence
<220> FEATURE:
<223> OTHER INFORMATION: oLLC104-r

<400> SEQUENCE: 44

```
gcacagctgt tatagcgcca ctcagactca tacccgttct cccg                       44
```

<210> SEQ ID NO 45
<211> LENGTH: 27
<212> TYPE: DNA
<213> ORGANISM: Artificial Sequence
<220> FEATURE:
<223> OTHER INFORMATION: VWF 1099C S

<400> SEQUENCE: 45

```
ggggactgcg cctgcttctg cgacacc                                          27
```

<210> SEQ ID NO 46
<211> LENGTH: 27
<212> TYPE: DNA
<213> ORGANISM: Artificial Sequence
<220> FEATURE:
<223> OTHER INFORMATION: VWF 1099C AS

<400> SEQUENCE: 46

```
ggtgtcgcag aagcaggcgc agtcccc                                          27
```

```
<210> SEQ ID NO 47
<211> LENGTH: 29
<212> TYPE: DNA
<213> ORGANISM: Artificial Sequence
<220> FEATURE:
<223> OTHER INFORMATION: VWF 1142C S

<400> SEQUENCE: 47
gaacgggtat gagtgtgagt ggcgctata                              29

<210> SEQ ID NO 48
<211> LENGTH: 29
<212> TYPE: DNA
<213> ORGANISM: Artificial Sequence
<220> FEATURE:
<223> OTHER INFORMATION: VWF 1142C AS

<400> SEQUENCE: 48
tatagcgcca ctcacactca tacccgttc                              29

<210> SEQ ID NO 49
<211> LENGTH: 42
<212> TYPE: DNA
<213> ORGANISM: Artificial Sequence
<220> FEATURE:
<223> OTHER INFORMATION: 2764pJSV348F

<400> SEQUENCE: 49
gcgctagctg aggaccaagt agatccgcgg ctcattgatg gg               42

<210> SEQ ID NO 50
<211> LENGTH: 37
<212> TYPE: DNA
<213> ORGANISM: Artificial Sequence
<220> FEATURE:
<223> OTHER INFORMATION: 1202pJSV348R

<400> SEQUENCE: 50
gggccagagc aagcagcacc ccggcaaatc tggcagg                     37

<210> SEQ ID NO 51
<211> LENGTH: 37
<212> TYPE: DNA
<213> ORGANISM: Artificial Sequence
<220> FEATURE:
<223> OTHER INFORMATION: 221 796F

<400> SEQUENCE: 51
cctgccagat ttgccggggt gctgcttgct ctggccc                     37

<210> SEQ ID NO 52
<211> LENGTH: 47
<212> TYPE: DNA
<213> ORGANISM: Artificial Sequence
<220> FEATURE:
<223> OTHER INFORMATION: 3537 796R

<400> SEQUENCE: 52
tacttggtcc tcagctagcg cctgggggca caatgtggcc gtcctcc          47

<210> SEQ ID NO 53
<211> LENGTH: 47
<212> TYPE: DNA
<213> ORGANISM: Artificial Sequence
<220> FEATURE:
<223> OTHER INFORMATION: 3747 796R
```

```
<400> SEQUENCE: 53
tacttggtcc tcagctagcg ccactggaca gtcttcaggg tcaacgc                47

<210> SEQ ID NO 54
<211> LENGTH: 38
<212> TYPE: DNA
<213> ORGANISM: Artificial Sequence
<220> FEATURE:
<223> OTHER INFORMATION: 2420pJSV348R

<400> SEQUENCE: 54
ggctcagggt gctgacacgt gacttgacag gcaggtgc                          38

<210> SEQ ID NO 55
<211> LENGTH: 38
<212> TYPE: DNA
<213> ORGANISM: Artificial Sequence
<220> FEATURE:
<223> OTHER INFORMATION: 3666 796F

<400> SEQUENCE: 55
gcacctgcct gtcaagtcac gtgtcagcac cctgagcc                          38

<210> SEQ ID NO 56
<211> LENGTH: 46
<212> TYPE: DNA
<213> ORGANISM: Artificial Sequence
<220> FEATURE:
<223> OTHER INFORMATION: 5203 796R

<400> SEQUENCE: 56
tacttggtcc tcagctagcg ctgcagggga gagggtgggg atctgc                 46

<210> SEQ ID NO 57
<211> LENGTH: 479
<212> TYPE: PRT
<213> ORGANISM: Artificial Sequence
<220> FEATURE:
<223> OTHER INFORMATION: VWF fragment: amino acids 764-1242

<400> SEQUENCE: 57
```

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Ile Glu Leu Phe Asp Gly
            165                 170                 175

Glu Val Asn Val Lys Arg Pro Met Lys Asp Glu Thr His Phe Glu Val
        180                 185                 190

Val Glu Ser Gly Arg Tyr Ile Ile Leu Leu Leu Gly Lys Ala Leu Ser
    195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
465                 470                 475

<210> SEQ ID NO 58
<211> LENGTH: 719
<212> TYPE: PRT
<213> ORGANISM: Artificial Sequence
<220> FEATURE:
<223> OTHER INFORMATION: vWF fragment: amino acids 764-1482

<400> SEQUENCE: 58

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

```
Pro Gly Met Val Arg His Glu Asn Arg Cys Val Ala Leu Glu Arg Cys
 50                  55                  60
Pro Cys Phe His Gln Gly Lys Glu Tyr Ala Pro Gly Glu Thr Val Lys
 65                  70                  75                  80
Ile Gly Cys Asn Thr Cys Val Cys Gln Asp Arg Lys Trp Asn Cys Thr
                 85                  90                  95
Asp His Val Cys Asp Ala Thr Cys Ser Thr Ile Gly Met Ala His Tyr
                100                 105                 110
Leu Thr Phe Asp Gly Leu Lys Tyr Leu Phe Pro Gly Glu Cys Gln Tyr
            115                 120                 125
Val Leu Val Gln Asp Tyr Cys Gly Ser Asn Pro Gly Thr Phe Arg Ile
130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                165                 170                 175
Glu Val Asn Val Lys Arg Pro Met Lys Asp Glu Thr His Phe Glu Val
                180                 185                 190
Val Glu Ser Gly Arg Tyr Ile Ile Leu Leu Leu Gly Lys Ala Leu Ser
            195                 200                 205
Val Val Trp Asp Arg His Leu Ser Ile Ser Val Val Leu Lys Gln Thr
210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
Asp Phe Gly Asn Ser Trp Lys Val Ser Ser Gln Cys Ala Asp Thr Arg
                260                 265                 270
Lys Val Pro Leu Asp Ser Ser Pro Ala Thr Cys His Asn Asn Ile Met
            275                 280                 285
Lys Gln Thr Met Val Asp Ser Ser Cys Arg Ile Leu Thr Ser Asp Val
290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
                340                 345                 350
Lys Val Val Thr Trp Arg Thr Ala Thr Leu Cys Pro Gln Ser Cys Glu
            355                 360                 365
Glu Arg Asn Leu Arg Glu Asn Gly Tyr Glu Cys Glu Trp Arg Tyr Asn
370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
                420                 425                 430
Cys Pro Val Cys Glu Val Ala Gly Arg Arg Phe Ala Ser Gly Lys Lys
            435                 440                 445
Val Thr Leu Asn Pro Ser Asp Pro Glu His Cys Gln Ile Cys His Cys
450                 455                 460
```

-continued

```
Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
    610                 615                 620

Gln Glu Pro Gln Arg Met Ser Arg Asn Phe Val Arg Tyr Val Gln Gly
625                 630                 635                 640

Leu Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
    690                 695                 700

Thr Leu Pro Pro Asp Met Ala Gln Val Thr Val Gly Pro Gly Leu
705                 710                 715
```

The invention claimed is:

1. A pharmaceutical composition comprising: (i) a Von Willebrand Factor (VWF) fragment comprising up to 800 amino acids and one or more domains selected from the group consisting of trypsin-inhibitor-like (TIL'), E', and D3 and (ii) a B domain-truncated Factor VIII molecule with an amino acid sequence comprising SEQ ID NO:2, wherein SEQ ID NO:2 is modified by a deletion of its C-terminal R.

2. The pharmaceutical composition according to claim 1, wherein the amino acid sequence of the B domain-truncated Factor VIII from N-terminal to C-terminal consists of amino acid residues 1-750, 1638-1647, and 1649-2332 of SEQ ID NO: 1 and, wherein an O-glycan is linked to the Ser 750 amino acid residue.

3. The pharmaceutical composition according to claim 1, wherein the B domain-truncated Factor VIII molecule is conjugated with at least one half-life extending moiety.

4. The pharmaceutical composition according to claim 3, wherein the at least one half-life extending moiety is covalently attached to an O-glycan linked to the B domain-truncated Factor VIII molecule at an amino acid residue within the amino acid sequence represented by SEQ ID NO:2, wherein SEQ ID NO:2 is modified by the deletion of the C-terminal R.

5. The pharmaceutical composition according to claim 1, wherein the bioavailability of the B domain-truncated Factor VIII molecule is at least 5% following subcutaneous administration.

6. The pharmaceutical composition according to claim 1, wherein the molar ratio between the B domain-truncated Factor VIII molecule and VWF is 1:1.

7. The pharmaceutical composition according to claim 1, wherein the concentration of the B domain-truncated Factor VIII molecule is at least 500 IU/ml.

8. The pharmaceutical composition according to claim 1, wherein the amount of the B domain-truncated Factor VIII molecule bound to the VWF fragment is at least 70% of the total amount of B domain-truncated the Factor VIII molecule in said composition.

9. The pharmaceutical composition according to claim 1 for use in treating haemophilia, wherein said pharmaceutical composition is for subcutaneous administration.

10. The pharmaceutical composition according to claim 1 for use in treating haemophilia, wherein said pharmaceutical composition is for intravenous administration.

11. The pharmaceutical composition according to claim 1 for use in treating haemophilia, wherein said pharmaceutical composition is a freeze-dried composition.

12. The pharmaceutical composition according to claim 1 for use in treating haemophilia, wherein said pharmaceutical composition is a liquid composition.

13. The pharmaceutical composition according to claim 1, wherein the amino acid sequence of the VWF fragment is selected from the group consisting of: SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 58.

14. The pharmaceutical composition according to claim 1 for use in treatment of von willebrand disease by intravenous or subcutaneous administration.

15. The pharmaceutical composition according to one of claims 3 and 4, wherein the half-life extending moiety is poly(ethylene glycol).

16. A pharmaceutical composition comprising: (i) a Von Willebrand Factor (VWF) fragment comprising up to 800 amino acids and one or more domains selected from the group consisting of trypsin-inhibitor-like (TIL'), E', and D3; (ii) a B domain-truncated Factor VIII molecule with an amino acid sequence from N-terminal to C-terminal consisting of amino acid residues 1-750, 1638-1647, and 1649-2332 of SEQ ID NO: 1 and (iii) a poly(ethylene glycol) moiety attached to the B domain-truncated Factor VIII molecule via an O-glycan linked to the Ser 750 amino acid residue.

17. The pharmaceutical composition according to claim 16, wherein the VWF fragment is selected from the group consisting of: SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 58.

18. The pharmaceutical composition according to claim 17, wherein the VWF fragment is SEQ ID NO: 19.

19. The pharmaceutical composition according to claim 16, wherein the molar ratio between the Factor VIII molecule and VWF is from 1:1 to 1:7.7.

20. The pharmaceutical composition according to claim 19, wherein the molar ratio is 1:1.

* * * * *